US008815511B2

(12) United States Patent
Tchelet et al.

(10) Patent No.: US 8,815,511 B2
(45) Date of Patent: Aug. 26, 2014

(54) DETERMINATION OF SINGLE NUCLEOTIDE POLYMORPHISMS USEFUL TO PREDICT RESPONSE FOR GLATIRAMER ACETATE

(71) Applicant: Teva Pharmaceutical Industries, Ltd., Petach-Tikva (IL)

(72) Inventors: Amir Tchelet, Hod-Hasharon (IL); Fabio Mucciardi, Irvine, CA (US); Joseph Levy, Kfar-Sava (IL)

(73) Assignee: Teva Pharmaceutical Industries, Ltd., Petach-Tikva (IL)

(*) Notice: Subject to any disclaimer, the term of this patent is extended or adjusted under 35 U.S.C. 154(b) by 0 days.

(21) Appl. No.: 13/648,135

(22) Filed: Oct. 9, 2012

(65) Prior Publication Data
US 2013/0123189 A1 May 16, 2013

Related U.S. Application Data

(60) Provisional application No. 61/636,560, filed on Apr. 20, 2012, provisional application No. 61/545,282, filed on Oct. 10, 2011.

(51) Int. Cl.
*A61K 38/16* (2006.01)
*C12Q 1/68* (2006.01)

(52) U.S. Cl.
USPC ........................ 435/6.11; 514/17.9

(58) Field of Classification Search
None
See application file for complete search history.

(56) References Cited

U.S. PATENT DOCUMENTS

| | | | |
|---|---|---|---|
| 5,800,808 A | 9/1998 | Konfino et al. | |
| 5,981,589 A | 11/1999 | Konfino et al. | |
| 6,048,898 A | 4/2000 | Konfino et al. | |
| 6,054,430 A | 4/2000 | Konfino et al. | |
| 6,214,791 B1 | 4/2001 | Arnon et al. | |
| 6,342,476 B1 | 1/2002 | Konfino et al. | |
| 6,362,161 B1 | 3/2002 | Konfino et al. | |
| 6,514,938 B1 | 2/2003 | Gad et al. | |
| 6,620,847 B2 | 9/2003 | Konfino et al. | |
| 6,800,285 B2 | 10/2004 | Rodriguez et al. | |
| 6,800,287 B2 | 10/2004 | Gad et al. | |
| 6,844,314 B2 | 1/2005 | Eisenbach-Schwartz et al. | |
| 6,939,539 B2 | 9/2005 | Konfino et al. | |
| 7,022,663 B2 | 4/2006 | Gilbert et al. | |
| 7,033,582 B2 | 4/2006 | Yong et al. | |
| 7,074,580 B2 | 7/2006 | Gad et al. | |
| 7,163,802 B2 | 1/2007 | Gad et al. | |
| 7,199,098 B2 | 4/2007 | Konfino et al. | |
| 7,279,172 B2 | 10/2007 | Aharoni | |
| 7,351,686 B2 | 4/2008 | Eisenbach-Schwartz et al. | |
| 7,407,936 B2 | 8/2008 | Eisenbach-Schwartz et al. | |
| 7,425,332 B2 | 9/2008 | Aharoni et al. | |
| 7,429,374 B2 | 9/2008 | Klinger | |
| 7,495,072 B2 | 2/2009 | Dolitzky et al. | |
| 7,560,100 B2 | 7/2009 | Pinchasi et al. | |
| 7,615,359 B2 | 11/2009 | Gad et al. | |
| 7,855,176 B1 | 12/2010 | Altman et al. | |
| 7,923,215 B2 | 4/2011 | Klinger | |
| 2002/0037848 A1 | 3/2002 | Eisenbach-Schwartz | |
| 2003/0170729 A1 | 9/2003 | Klinger | |
| 2005/0064483 A1 | 3/2005 | Zang et al. | |
| 2005/0170004 A1 | 8/2005 | Rosenberger | |
| 2006/0052586 A1 | 3/2006 | Dolitzky | |
| 2006/0172942 A1 | 8/2006 | Dolitzky | |
| 2006/0229233 A1 | 10/2006 | Frenkel et al. | |
| 2006/0240463 A1 | 10/2006 | Lancet | |
| 2006/0264354 A1 | 11/2006 | Aharoni et al. | |
| 2007/0021324 A1 | 1/2007 | Dolitzky | |
| 2007/0021341 A1 | 1/2007 | Sela et al. | |
| 2007/0037740 A1 | 2/2007 | Pinchasi et al. | |
| 2007/0048794 A1 | 3/2007 | Gad et al. | |
| 2007/0054857 A1 | 3/2007 | Pinchasi et al. | |
| 2007/0059798 A1 | 3/2007 | Gad | |
| 2007/0161566 A1 | 7/2007 | Pinchasi | |
| 2007/0173442 A1 | 7/2007 | Vollmer | |
| 2007/0248569 A1 | 10/2007 | Eisenbach-Schwartz | |
| 2008/0085269 A1 | 4/2008 | Eisenbach-Schwartz | |
| 2008/0131887 A1* | 6/2008 | Stephan et al. | ........... 435/6 |

(Continued)

FOREIGN PATENT DOCUMENTS

| | | |
|---|---|---|
| WO | WO 98/30227 | 7/1998 |
| WO | WO 00/05250 | 2/2000 |
| WO | WO 00/18794 | 4/2000 |
| WO | WO 00/27417 | 5/2000 |
| WO | WO 01/60392 | 8/2001 |
| WO | WO 01/93828 | 12/2001 |
| WO | WO 01/97846 | 12/2001 |
| WO | WO 03/048735 | 6/2003 |
| WO | WO 2004/103297 | 2/2004 |
| WO | WO 2004/043995 | 5/2004 |

(Continued)

OTHER PUBLICATIONS

Byun et al., Genome-Wide Pharmacogenomic Analysis of the Response to Interferon Beta Therapy in Multiple Sclerosis, Mar. 2008, Arch. Neurol. 65 (3):337-344.*

(Continued)

*Primary Examiner* — John Ulm
(74) *Attorney, Agent, or Firm* — John P. White; Gary J. Gershik; Cooper & Dunham LLP

(57) ABSTRACT

This invention provides a method for treating a human subject afflicted with multiple sclerosis or a single clinical attack consistent with multiple sclerosis with a pharmaceutical composition comprising glatiramer acetate and a pharmaceutically acceptable carrier, comprising the steps of 1) identifying whether the human subject is a predicted responder to glatiramer acetate by determining the genotype of the subject at one or more single nucleotide polymorphisms (SNPs) selected from the group consisting of the SNPs in Group 1; and 2) administering the pharmaceutical composition comprising glatiramer acetate and a pharmaceutically acceptable carrier to the subject only if the subject is identified as a predicted responder to glatiramer acetate.

23 Claims, 3 Drawing Sheets

(56) References Cited

U.S. PATENT DOCUMENTS

| | | |
|---|---|---|
| 2008/0207526 A1 | 8/2008 | Strominger |
| 2009/0053253 A1 | 2/2009 | Klinger |
| 2009/0149541 A1 | 6/2009 | Stark et al. |
| 2009/0214470 A1 | 8/2009 | Eisenbach-Schwartz et al. |
| 2010/0167983 A1 | 7/2010 | Kreitman et al. |
| 2010/0210817 A1 | 8/2010 | Gad et al. |
| 2010/0285600 A1 | 11/2010 | Lancet et al. |
| 2010/0298227 A1 | 11/2010 | Aharoni et al. |
| 2010/0305023 A1 | 12/2010 | Stark et al. |
| 2011/0046065 A1 | 2/2011 | Klinger |
| 2011/0060279 A1 | 3/2011 | Altman et al. |
| 2011/0066112 A1 | 3/2011 | Altman |
| 2011/0117115 A1 | 5/2011 | Eisenbach-Schwartz |
| 2011/0230413 A1 | 9/2011 | Dhib-Jalbutt |

FOREIGN PATENT DOCUMENTS

| | | |
|---|---|---|
| WO | WO 2005/041933 | 5/2005 |
| WO | WO 2006/050122 | 5/2006 |
| WO | WO 2006/083608 | 8/2006 |
| WO | WO 2006/116602 | 11/2006 |
| WO | WO 2008/006026 | 1/2008 |
| WO | WO 2009/070298 | 6/2009 |

OTHER PUBLICATIONS

Canadian Patent Application No. 2,606,194, flied Apr. 24, 2006 (Lancet et al.), Canadian counterpart of U.S. Appl. No. 11/409,590.
European Patent Application No. 06758673.5, filed Apr. 24, 2006 (European counterpart of U.S. Appl. No. 11/409,590).
PCT International Preliminary Report on Patentability issued Mar. 19, 2009 for International Application No. PCT/US2006/016036 (WO 2006/116602) (International counterpart of U.S. Appl. No. 11/409,509).
PCT International Search Report Issued Aug. 11, 2008 for International Application No. PCT/US2006/016036 (WO 2006/116602) (International counterpart of U.S. Appl. No. 11/409,509).
PCT Written Opinion issued Aug. 11, 2008 for International Application No. PCT/US2006/016036 (WO 2006/116602) (International counterpart of U.S. Appl. No. 11/409,509).
Feb. 18, 2010 Extended European Search Report in connection with European Patent Application No. 06758673.5.
Oct. 15, 2007 Office Action in connection with U.S. Appl. No. 11/409,590.
Jan. 15, 2008 Amendment in Response to Oct. 15, 2007 Office Action in connection with U.S. Appl. No. 11/409,590.
Mar. 14, 2008 Supplemental Response to Oct. 15, 2007 Office Action in connection with U.S. Appl. No. 11/409,590.
Jun. 18, 2008 Office Communication in connection with U.S. Appl. No. 11/409,590.
Jul. 18, 2008 Response to Jun. 18, 2008 Office Communication in connection with U.S. Appl. No. 11/409,590.
Oct. 24, 2008 Office Action in connection with U.S. Appl. No. 11/409,590.
Apr. 24, 2009 Amendment in Response to Oct. 24, 2008 Office Action in connection with U.S. Appl. No. 11/409,590.
Aug. 20, 2009 Final Office Action in connection with U.S. Appl. No. 11/409,590.
Opposition filed on Feb. 15, 2010 in connection with European Patent No. 1 459 065, granted Jul. 28, 2010 (European Application No. 02790028.1).
Opposition filed on Apr. 28, 2011 in connection with European Patent No. 1 115 743, granted May 26, 2009.
Opposition filed on Oct. 5, 2010 in connection with European Patent No. 1799703, granted Jan. 6, 2010.
Aharoni "Glatiramer acetate-specific T cells in the brain express T helper 2/3 cytokines and brain-derived neurotrophic factor in situ." PNAS Aug. 2003;100(24):14157-62.
Anderson, et al., (1992) "Revised estimate of the prevalence of multiple sclerosis in the United States." Ann Neurol., 31: 333-336.
Aranami et al. "Th17 Cells and autoimmune encephalomyelitis (EAE/MS)" Allergol Int. Jun. 2008; 57(2):115-20.
Beebe et al., "The role of IL-10 in autoimmune disease: systemic lupus erythematosus (SLE) and multiple sclerosis (MS)," Cytokine Growth factor rev. 12 (2002):403-412.
Begum-Haque et al., "Downregulation of IL-17 and IL-6 in the central nervous system by glatiramer acetate in experimental autoimmune encephalomyelitis." J Neuroimmunol. Nov. 15, 2008;204(1-2):58-65.
Bornstein, et al., "Treatments of Multiple Sclerosis with a Synthetic Polypeptide: Preliminary Results," Ann. Neurol., 1980, 8, 117 (Abstract).
Bornstein, et al., "Treatments of Multiple Sclerosis with a Synthetic Polypeptide: Preliminary Results," Trans. Am. Neurol. Assoc., 1980, 105, 348-350.
Bornstein, et al., "Multiple Sclerosis: Trial of a Synthetic Polypeptide," Ann. Neurol., 1982, 11, 317-319.
Bornstein, et al., "Clinical Trials of Copolymer 1 in Multiple Sclerosis," Ann. N.Y. Acad. Sci. (USA), 1984, 366-372.
Bornstein, et al., "Clinical Trials of a Synthetic Polypeptide (Copolymer 1) for the treatment of Mutliple Sclerosis" in Gonsett et al., Immunological and Clinical Aspects of Multiple Sclerosis (MTP Press, The Hague, 1984) 144-150.
Bornstein, et al., "Multiple Sclerosis: Clinical Trials of a Synthetic Polypeptide, Copolymer 1," Neurol., 1985, 35, (Suppl. 1), 103 (Abstract).
Bornstein, "Cop 1 may be Beneficial for Patients with Exacerbating-remitting Form of Multiple Sclerosis," Adv. Ther. (USA), 1987, 4, 206 (Abstract) (Exhibit 45).
Bornstein, et al., "A Pilot Trial of Cop 1 in Exacerbating-remitting Multiple Sclerosis," New Eng. J. Med., 1987, 317(7), 408-414.
Bornstein, et al., "Clinical Experience with COP-1 in Multiple Sclerosis," Neurol., 1988, 38(Suppl. 2) 66-69.
Bornstein et al., "Rationale for Immunomodulating Therapies of Multiple Sclerosis: Clinical Trial Design in Multiple Sclerosis Therapy," Neurol., 1988, vol. 38 (Suppl.2), pp. 80-81 [R].
Bornstein, et al., "Pilot Trial of COP-1 in Chronic Progressive Multiple Sclerosis: Preliminary Report," from The International Multiple Sclerosis Conference: An Update on Multiple Sclerosis, Roma (Italy), Sep. 15-17, 1988, in Elsevier Science Publisher, 1989, 225-232.
Bornstein, et. al., "Clinical Trials of Cop 1 in Multiple Sclerosis," in Handbook of Multiple Sclerosis (S.D. Cook Marcel ed., 1990) 469-480.
Bornstein , et al., "A Placebo-controlled, Double-blind, Randomized Two-center, Pilot Trial of Cop 1 in Chronic Prgressive Multiple Sclerosis," Neurol., 1991, 41, 533-539.
Bornstein, et al., "Treatment of Multiple Sclerosis with Copolymer 1" in Treatment of Multiple Sclerosis: Trial Design, Results and Future Perspectives (Rudick R.A. & Goodkin D.E., eds., Springer Lerlag, London, 1992) 173-198.
Bornstein, "Clincal Experience: Hopeful Prospects in Multiple Sclerosis," Hospital Practice (Off. Ed.), 1992, vol. 27, No. 5, pp. L135-L158, 141-142, 145-158.
Brex et al., (2002) "A longitudinal study of abnormalities on MRI and disability from multiple sclerosis" Engl. J. Med., 3: 158-64.
Burger, Daniella et al., "Glatiramer acetate increases IL-1 receptor antagonist but decreases T cell-induced IL-B in human monocytes and multiple sclerosis," PNAS PNAS 2009 106 (11) 4355-4359 (2009); Early Edition 0812183106.
Cagguila et al., "Neurotrophic factors and clinical recovery in RR-MS," Scand J Immunol 2005, 62: 176-82.
Chen et al., "Glatiramer acetate induces a Th-2 biased response and cross-reactivity with myelin basic protein in patients with MS." Multiple Sclerosis 2001; 7:209-219.
Cohen et al., Identifying and treating patients with suboptimal responses. Neurology Dec. 28, 2004;63(12 Suppl 6):S33-40.
Comi G. et al., (2001) "European/Canadian Multicenter, Double-Blind, Randomized, Placebo-controlled study of the effects of Glatiramer acetate on Magnetic resonance imaging-measured disease activity and burden in patients with relapsing multiple sclerosis" Ann. Neurol. 49:290-297.

(56) References Cited

OTHER PUBLICATIONS

Comi, et al. (2008) "Results from a phase III, one-year, randomized, double-blind, parallel-group, dose-comparison study with glatiramer acetate in relapsing-remitting multiple sclerosis". Mult Scler., 14(Suppl 1):S299.

Comi et al. Treatment with glatiramer acetate delays conversion to clinically definite multiple sclerosis (CDMS) in patients with clinically isolated syndromes (CIS). Neurology 2008; 71 (2): 153.

Cua et al., "Transgenic Interleukin-10 prevents induction of experimental autoimmune encephalomyelitis." J. Exp. Med. 189 (1999):1005-1010.

Dhib-Jalbut SS, Zhan M, Johnson KP, Martin R. Glatiramer acetate reactive blood mononuclear cells respond to myelin antigens with a Th-2 biased phenotype. J Neuroimmunology 2003; 140 :163-171.

Farina et al., "Treatment of multiple sclerosis with Copaxone (COP): Elispot assay detects COP-induced interleukin-4 and interferon-gamma response in blood cells." Brain. Apr. 2001;124(Pt 4):705-19.

Farina et al., "Immunological assay for assessing the efficacy of glatiramer acetate (Copaxone) in multiple sclerosis. A pilot study." J Neurol. Nov. 2002;249(11):1587-92.

Fridkis-Hareli, et al. "Direct binding of myelin basic protein and synthetic copolymer 1 to class II major histocompatibility complex molecules on living antigen-presenting cells-specificity and promiscuity," Proc. Natl. Acad. Sci. USA. 91: 4872-6 (1994).

Fridkis-Hareli, et al., "Binding Motifs of Copolymer 1 to Multiple Sclerosis- and Rheumatoid Arthritis-Associated HLA-DR Molecules" J. Immunol., 1999, 162: 4697-4704.

Fridkis-Hareli et al., "Binding of random copolymers of three amino acids to class II MCH molecules," Intl. Immunol., 1999, 11(5): 635-641.

Fridkis-Hareii et al., "Novel synthetic amino acid copolymers that inhibit autoantigen-specific T cell responses and suppress experimental autoimmune encephalomyelitis." J Clin Invest 109: 1635-1643 (2002).

Frohman et al., (2003) "The utility of MRI in suspected MS: report of Therapeutics and Technology Assessment Subcommittee of the American Academy of Neurology" Neurology Sep. 9, 61(5):602-11.

Gielen et al. "Increased brain-derived neurotrophic factor in white blood cells or RR MS patients" Scand J Immunol 2003, 57:493-97.

Gravel et al., "Adenoviral gene transfer of ciliary neurotrophic factor and brain-derived neurotrophic factor leads to long-term survival of axotomized motor neurons" Nat Med 1997; Jul. 3(7): 765-770.

Grossman et al., "Pharmacogenetics of glatiramer acetate therapy for multiple sclerosis reveals drug-response markers" PHarmacogenetics and Genomics, 2007, 17: 657-666.

Groux et al., "Interleukin-10 induces a long-term antigen specific anergic state in human CD4+ T cells." J. exp. Med. 184 (1996):19-29.

Hirschorn et al., "A comprehensive review of genetic association studies" Genetics in Medicine, Mar. 2002, 4(2): 45-61.

Hong et al. Induction of CD4+CD25+ regulatory T cells by copolymer-I through activation of transcription factor Foxp3. Proc Natl Acad Sci May 3, 2005;102(18):6449-54. Epub Apr. 25, 2005.

Hussein et al. "Glatiramer acetate and IFN-beta act on dendritic cells in multiple sclerosis." J Neuro Immunol (2001)121:102-110.

Imitola et al., "Cytokines in multiple sclerosis: from bench to bedside" PharmacoIoannidis, et al. "Replication validity of genetic association studies" Nature Genetics, Nov. 2001, 29: 306-3091. Ther. 106 (2005):163-177.

Ioannidis, et al. "Replication validity of genetic association studies" Nature Genetics, Nov. 2001, 29: 306-309.

Jee et al., "CD4(+)CD25(+) regulatory T cells contribute to the therapeutic effects of glatiramer acetate in experimental autoimmune encephalomyelitis." Clin Immunol Oct. 2007;125(1):34-42. Epub Jul. 16, 2007.

Johnson D, Hafler DA, Fallis RJ, Lees MB, Brady RO, Quarles RH, Weiner HL., "Cell-mediated immunity to myelin-associated glycoprotein, proteolipid protein, and myelin basic protein in multiple sclerosis.", J Neuroimmunol. Nov. 1986;13 (1):99-108.

Kim et al. "Type 2 monocytes and microglia differentiation mediated by glatiramer acetate therapy in patients with multiple sclerosis." J Immunol (2004) 172:7144-7153.

Lucentini, "Second RNAi pathway emerges" The Scientist, Aug. 2004, 24: 20.

Martinelli et al. "Effects of glatiramer acetate on relapse rate and accumulated disability in multiple sclerosis: meta-analysis of three double-blind, randomized, placebo-controlled clinical trials." Mult Scler. Aug. 2003; 9(4):349-55.

Martinez et al., "IL-10 suppressor activity and ex-vivo Trl cell function are impaired in multiple sclerosis." Eur J Immunol. Feb. 2008;38(2):576-86.

McDonald et al., "Recommended diagnostic criteria for multiple sclerosis: guidelines from the International Panel on the diagnosis of multiple sclerosis." Ann Neurol. Jul. 2001;50(1):121-7.

Mikol et al., Lancet Neurol. Oct. 2008;7(10):903-14. Epub Sep. 11, 2008.

Noseworthy, et al. (2000) "Multtple sclerosis". N Engl J Med., 343: 938-52.

Revel M., "Interferon-β in the treatment of relapsing-remitting multiple sclerosis" Pharmacol. Ther., 100(1):49-62 (2003).

Roncarlo "Type-1 regulatory cells." Immunol. Rev. 182(2001):68-80.

Rott et al., "Interleukin 10 prevents experimental allergic encephalomyelitis in rats." Eur. J. Immunol 24(1994):1434-1440.

Sarchielli et al. "Brain-derived neurotrophic factor in patients with multiple sclerosis". J Neuroimmunol Nov. 2002 132(1-2):180-88.

Sarchielli et al. "Production of brain-derived neurotrophic factor by mononuclear cells of patients with multiple sclerosis treated with glatiramer acetate, interferon-beta la, and high doses of immunoglobulins." Mult Scler Apr. 2007;13(3):313-31. Epub Jan. 29, 2007.

Stern et al., "Amino acid copolymer-specific IL-10 secreting regulatory T-cells that ameliorate autoimmune disease in mice," PNAS 2008, 105(13):5172-5176.

Tselis, et al., (2007) "Giatiramer acetate in the treatment of multiple sclerosis" Neuropsychiatric Dis Treat., 3(2): 259-67.

Valenzuela, et al., "Clinical response to glatiramer acetate correlates with modulation of IFN-gamma and IL-4 expression in multiple sclerosis." Mult Scler., Jul. 2007;13(6):754-62.

Valenzuela, et al. "Time course and functional capacity of glatiramer acetate-induced regulatory T-cells in multiple sclerosis patients." 23rd Congress of the European Committee for the Treatment and Research in Multiple Sclerosis (ECTRIMS), Oct. 12, 2007. (abstract).

Valenzuela "Predictive biomarkers of clinical response to Glatiramer Acetate (GA) therapy in Multiple Sclerosis" 2009, poster.

Vieira et al. "Glatiramer acetate (copolymer-1, copaxone) promotes Th2 cell development and increased IL-10 production through modulation of dendritic cells." J Immunol (2003) 170:4483-4488.

Weber et al. "Type II monocytes modulate T cell-mediated central nervous sytem autoimmune disease." Nat Med (2007) 13:935-943.

Wolinsky, et al. (2007) "Glatiramer acetate in primary progressive multiple sclerosis: Results of a multinational, multicenter, double-blind, placebo-controlled trial". Ann Neurol. 61: 14-24.

Copaxone (glatiramer acetate injection), prescribing information, [Feb. 27, 2009] www.copaxone.com/pdf/prescribingInformation.pdf.

Clinical Trial Protocol No. 9001, Teva Pharmaceutical Industries, Ltd., first patient enrolled Oct. 23, 1991.

Clinical Trial Protocol. No. 9002, Lemmon Co. and Teva Pharmaceutical Industries, Ltd., first patient enrolled Jun. 17, 1993.

U.S. Appl. No. 11/590,338, filed Oct. 30, 2006 (Pinchasi et al.).

Become Trial, Presented at the 23rd Congress of the European Committee for Treatment and Research in Multiple Sclerosis (ECTRIMS) in Prague, Czech Republic. (Oct. 11-14, 2007).

Bjartmaer et al. (2002) "Pathological mechanism and disease progression of multiple sclerosis: therapeutic implications" Drugs of Today 38(1):17-29.

Felderhoff-Mueser U. et al. (2005) "IL-18: A key playerin neuroinflammation and neurodegeneration" Trends in Neuroscience 28(9): 487-93.

(56) References Cited

OTHER PUBLICATIONS

NCBI Submitted SNP(ss) Details: ss23440768. RefSNP No. rs17087180. Aug. 20, 2004 [Retrieved from the internet on Mar. 7, 2013] url:http://www.ncbi.nlm.nih.gov/projects/SNP/snp_ss.cgi?ss=ss23440768.

NCBI Reference sequence NT-010274.17—*Homo sapiens* chromosome 15 genomic contig, GRCh37.p5 Primary Assembly (Jul. 29, 2011) url:http://www.ncbi.nlm.nih.gov/nuccore/224514936?sat=16&satkey=3691065.

Johnson et al. (1998) "Extended Use of glatiramer acetate (Copaxone) is well tolerated and maintains its clinical effect on multiple sclerosis . . . " Neurology 50:701-708.

Neurostatus, Slightly modified from J.F. Kurtzke, Neurology 1983:33, 1444-52, Ludwig Kappos, MD, Neurology, University Hospital 4031 Basel, Switzerland.

Wolinsky J.S. (2006) "The use of glatiramer acetate in the treatment of multiple sclerosis" Advances in Neurology 98:273-292.

Byun et al. "Genome-wide pharmacogenic analysis of the response to interferon beta therapy in multiple sclerosis" Arch Neurol. Mar. 2008; 65(3):337-44. Epub Jan. 14, 2008.

PCT International Search Report issued Mar. 22, 2013 in connection with PCT international Application No. PCT/US12/59352.

NCBI Submitted SNP(ss) Details: ss24494172. RefSNP No. rs17771939. Aug. 21, 2004 [Retrieved from the internet on Mar. 7, 2013] url:http://www.ncbi.nlm.nih.gov/projects/SNP/snp_ss.cgi?ss=ss24494172.

NCBI Submitted SNP(ss) Details: ss23143312. RefSNP No. rs9508834. Mar. 14, 2007 [Retrieved from the internet on Mar. 7, 2013] url:http://www.ncbi.nlm.nih.gov/projects/SNP/snp_ss.cgi?ss=ss23143312.

NCBI Submitted SNP(ss) Details: ss24400158 RefSNP No. rs17807327. Aug. 21, 2004 [Retrieved from the internet on Mar. 7, 2013] url:http://www.ncbi.nlm.nih.gov/projects/SNP/snp_ss.cgi?ss=ss24400158.

NCBI Submitted SNP(ss) Details: ss11216977. RefSNP No. rs4344916. Jul. 3, 2003 [Retrieved from the internet on Mar. 7, 2013] url:http://www.ncbi.nlm.nih.gov/projects/SNP/snp_ss.cgi?ss=ss11216977.

NCBI Submitted SNP(ss) Details: ss44410987. RefSNP No. rs12639443. Jul. 18, 2005 [Retrieved from the internet on Mar. 7, 2013] url:http://www.ncbi.nlm.nih.gov/projects/SNP/snp_ss.cgi?ss=ss44410987.

Comi G, Filippi M. Presented at: 60th Annual Meeting of the American Academy of Neurology: Apr. 12-19, 2008; Chicago, IL. Abstract LBS.003.

Guideline of Clinical investigation of medicinal products for the treatment of multiple sclerosis EMEA, London Nov. 16, 2006 CPMP/EWP/561/98 Rev.1, pp. 1-12.

NCBI Reference SNP (refSNP) Cluster Report: rs1007328. Sep. 7, 2000 [Retrieved from the Internet on Jul. 29, 2013] <url:http://www.ncbi.nlm.nih.gov/projects/SNP/snp_ref.cgi?rs=1007328> Note: Document entitled "GRCh.p2 Genome Reference Consortium Human Build 37 patch release 2" uploaded in support of priority date of rs1007328. http://www/ncbi.nlm.nih.gov/assembly/GCA_000001405.3/, 6 pages.

\* cited by examiner

DETERMINATION OF SINGLE NUCLEOTIDE POLYMORPHISMS USEFUL TO PREDICT RESPONSE FOR GLATIRAMER ACETATE

This application claims priority of U.S. Provisional Application Nos. 61/636,560, filed Apr. 20, 2012 and 61/545,282, filed Oct. 10, 2011, the contents of each of which are hereby incorporated by reference.

Throughout this application various publications are referenced by their full citations in parentheses. The disclosures of these publications in their entireties are hereby incorporated by reference into this application in order to more fully describe the state of the art to which this invention pertains.

BACKGROUND OF THE INVENTION

Multiple Sclerosis

Multiple sclerosis (MS) is a chronic, debilitating autoimmune disease of the central nervous system (CNS) with either relapsing-remitting (RR) or progressive course leading to neurologic deterioration and disability. At time of initial diagnosis, RRMS is the most common form of the disease (1) which is characterized by unpredictable acute episodes of neurological dysfunction (relapses), followed by variable recovery and periods of clinical stability. The vast majority of RRMS patients eventually develop secondary progressive (SP) disease with or without superimposed relapses. Around 15% of patients develop a sustained deterioration of their neurological function from the beginning; this form is called primary progressive (PP) MS. Patients who have experienced a single clinical event (Clinically Isolated Syndrome or "CIS") and who show lesion dissemination on subsequent magnetic resonance imaging (MRI) scans according to McDonald's criteria, are also considered as having relapsing MS. (2)

With a prevalence that varies considerably around the world, MS is the most common cause of chronic neurological disability in young adults. (3, 4) Anderson et al. estimated that there were about 350,000 physician-diagnosed patients with MS in the United States in 1990 (approx. 140 per 100,000 population). (5) It is estimated that about 2.5 million individuals are affected worldwide. (6) In general, there has been a trend toward an increasing prevalence and incidence of MS worldwide, but the reasons for this trend are not fully understood. (5)

Current therapeutic approaches consist of i) symptomatic treatment ii) treatment of acute relapses with corticosteroids and iii) treatment aimed to modify the course of the disease. Currently treatment aimed to modify the course of the disease. Currently approved therapies target the inflammatory processes of the disease. Most of them are considered to act as immunomodulators but their mechanisms of action have not been completely elucidated. Immunosuppressants or cytotoxic agents are also used in some patients after failure of conventional therapies. Several medications have been approved and clinically ascertained as efficacious for the treatment of RR-MS; including BETASERON®, AVONEX® and REBIF®, which are derivatives of the cytokine interferon beta (IFNB), whose mechanism of action in MS is generally attributed to its immunomodulatory effects, antagonizing pro-inflammatory reactions and inducing suppressor cells. (7) Other approved drugs for the treatment of MS include Mitoxantrone and Natalizumab.

Glatiramer Acetate

Glatiramer acetate (GA) is the active substance in Copaxone®, a marketed product indicated for reduction of the frequency of relapses in patients with RRMS. Its effectiveness in reducing relapse rate and disability accumulation in RR-MS is comparable to that of other available immunomodulating treatments. (8, 9, 10) Glatiramer acetate consists of the acetate salts of synthetic polypeptides containing four naturally occurring amino acids: L-glutamic acid, L-alanine, L-tyrosine and L-lysine. The average molecular weight of glatiramer acetate is between 5,000 and 9,000 Daltons. At a daily standard dose of 20 mg, GA is generally well tolerated, however response to the drug is variable. In various clinical trials, GA reduced relapse rates and progression of disability in patients with RR-MS. The therapeutic effect of GA is supported by the results of magnetic resonance imaging (MRI) findings from various clinical centers (11), however there are no validated predictive biomarkers of response to GA treatment.

A possible initial mode of action of GA is associated with binding to MHC molecules and consequent competition with various myelin antigens for their presentation to T cells. (12) A further aspect of its mode of action is the potent induction of T helper 2 (Th2) type cells that presumably can migrate to the brain and lead to in situ bystander suppression. (13) It has been shown that GA treatment in MS results in the induction of GA-specific T cells with predominant Th2 phenotype both in response to GA and cross-reactive myelin antigens. (13, 14) Furthermore, the ability of GA-specific infiltrating cells to express anti-inflammatory cytokines such as IL-10 and transforming growth factor-beta (TGF-β) together with brain-derived neurotrophic factor (BDNF) seem to correlate with the therapeutic activity of GA in EAE. (15, 16, 17)

Clinical experience with GA consists of information obtained from completed and ongoing clinical trials and from post-marketing experience. The clinical program includes three double-blind, placebo-controlled studies in RRMS subjects treated with GA 20 mg/day. (18, 19, 20) A significant reduction in the number of relapses, compared with placebo, was seen. In the largest controlled study, the relapse rate was reduced by 32% from 1.98 under placebo to 1.34 under GA 20 mg. GA 20 mg has also demonstrated beneficial effects over placebo on MRI parameters relevant to RRMS. A significant effect in median cumulative number of Gd-enhancing lesions over 9 months of treatment (11 lesions in the 20 mg group compared to 17 lesions under placebo) was demonstrated.

The clinical program with GA also includes one double-blind study in chronic-progressive MS subjects, (21) one double-blind placebo-controlled study in primary progressive patients, (22) one double-blind placebo-controlled study in CIS patients (23) and numerous open-label and compassionate use studies, mostly in RRMS. The clinical use of GA has been extensively reviewed and published in the current literature (24, 25, 26, 27).

U.S. Pat. No. 7,855,176 discloses administering glatiramer acetate to patients afflicted with relapsing-remitting multiple sclerosis (RRMS) by subcutaneous injection of 0.5 ml of an aqueous pharmaceutical solution which contains in solution 20 mg glatiramer acetate and 20 mg mannitol (34).

U.S. Patent Application Publication No. US 2011-0046065 A1 discloses administering glatiramer acetate to patients suffering from relapsing-remitting multiple sclerosis by three subcutaneous injections of a therapeutically effective dose of glatiramer acetate over a period of seven days with at least one day between every subcutaneous injection (35).

Pharmacogenomics

Pharmacogenomics is the methodology which associates genetic variability with physiological responses to drug. Pharmacogenetics is a subset of pharmacogenomics and is defined as "the study of variations in DNA sequence as related to drug response" (ICH E15; www.fda.gov/downloads/RegulatoryInformation/Guidances/ucm129296.pdf. Pharmacogenetics focuses on genetic polymorphism in genes related to drug metabolism, drug mechanism of action, disease type, and side effects. Pharmacogenetics is the cornerstone of Personalized Medicine which allows the development of more individualized drug therapies to obtain more effective and safe treatment.

Pharmacogenetics has become a core component of many drug development programs, being used to explain variability in drug response among subjects in clinical trials, to address unexpected emerging clinical issues, such as adverse events, to determine eligibility for a clinical trial (pre-screening) to optimize trial yield, to develop drug-linked diagnostic tests to identify patients who are more likely or less likely to benefit from treatment or who may be at risk of adverse events, to provide information in drug labels to guide physician treatment decisions, to better understand the mechanism of action or metabolism of new and existing drugs, and to provide better understanding of disease mechanisms.

Generally, Pharmacogenetics analyses are performed in either of two methodology approaches: Candidate genes research technique, and Genome Wide Association Study (GWAS). Candidate genes research technique is based on the detection of polymorphism in candidate genes pre-selected using the knowledge on the disease, the drug mode of action, toxicology or metabolism of drug. The Genome Wide Association Study (GWAS) enables the detection of more than 1 M (one million) polymorphisms across the genome. This approach is used when related genes are unknown. DNA arrays used for GWAS can be also analyzed per gene as in candidate gene approach.

Pharmacogenetic Studies

Various pharmacogenetic studies were done in MS patients. For example, a Genome-Wide Association study by Byun et al. (36) focused on extreme clinical phenotypes in order to maximize the ability to detect genetic differences between responders and non-responders to interferon-beta. A multianalytical approach detected significant associations between several SNPs and treatment response. Responders and nonresponders had significantly different genotype frequencies for SNPs located in many genes, including glypican 5, collagen type XXV α1, hyaluronan proteoglycan link protein, calpastatin, and neuronal PAS domain protein 3. Other studies used pharmacogenetic analyses in order to characterize the genomic profile and gene expression profile of IFN responders and non-responders.

Other pharmacogenetic studies analyzed the genetic background associated with response to Glatiramer Acetate. For examples, Fusco C et al (37) assessed a possible relationship between HLA alleles and response to GA (N=83 RRMS). DRB1*1501 allele frequency was increased in MS patients compared to healthy controls (10.8% vs 2.7%; p=0.001). In DRB1*1501 carriers the response rate was 81.8% compared to 39.4% in non-carriers of DRB1*1501 and to 50% in the whole study population. Grossman et al (38) genotyped HLA-DRB1*1501 and 61 SNPs within a total of 27 other candidate genes, on DNA from two clinical trial cohorts. The study revealed no association between HLA-DRB1*1501 and response to GA. The results of the study are disclosed in the international application published as 802006/116602 (39).

Pharmacogenetics is the cornerstone of personalized medicine which allows the development of more individualized drug therapies to obtain more effective and safe treatment. Multiple Sclerosis is a complex disease with clinical heterogeneity. In patients afflicted with multiple sclerosis or a single clinical attack consistent with multiple sclerosis, the ability to determine the likelihood of treatment success would be an important tool improving the therapeutic management of the patients. As the therapeutic options for MS and CIS increase, the importance of being able to determine who will respond favorably to therapy and specifically to GA, has become of increasing significance.

SUMMARY OF THE INVENTION

This invention provides a method for treating a human subject afflicted with multiple sclerosis or a single clinical attack consistent with multiple sclerosis with a pharmaceutical composition comprising glatiramer acetate and a pharmaceutically acceptable carrier, comprising the steps of:

i. determining a genotype of the subject at one or more single nucleotide polymorphisms (SNPs) selected from the group consisting of: rs1007328, rs10083547, rs10136012, rs10214633, rs10277267, rs1040194, rs1041897, rs10853605, rs10931091, rs10935015, rs10935016, rs10935019, rs10950359, rs10950371, rs10988087, rs11009827, rs11009835, rs11081859, rs11599624, rs11617134, rs11618546, rs11694344, rs11709339, rs11719825, rs11761457, rs11907046, rs12055694, rs12256889, rs1229542, rs1229553, rs1229555, rs1229558, rs1229562, rs1229563, rs1229564, rs1229568, rs12340584, rs1234567, rs1234947, rs1237625, rs12488259, rs12494606, rs12496278, rs12524041, rs12529764, rs12532459, rs12540494, rs12593600, rs12633010, rs12637073, rs12639443, rs1264423, rs1282540, rs1282546, rs12968586, rs1299325, rs13021482, rs13042992, rs1320648, rs13238613, rs13245980, rs1415557, rs1538123, rs1573706, rs1591661, rs1611185, rs1683691, rs16999008, rs17007730, rs17087180, rs17104665, rs17104742, rs17134651, rs17575455, rs17588454, rs17666347, rs17771939, rs17807327, rs17807445, rs1886308, rs1892974, rs1941973, rs2033471, rs2088713, rs214526, rs2155262, rs2177073, rs2187495, rs2277431, rs2305623, rs2374730, rs2461319, rs2487889, rs2487896, rs2508806, rs2511064, rs2521643, rs2521644, rs2530121, rs2530123, rs2685484, rs2722396, rs2722398, rs28861531, rs2895215, rs2937395, rs3135391, rs35831078, rs3742228, rs401618, rs4148871, rs4255033, rs4281882, rs4289164, rs4306478, rs4343256, rs4344916, rs4369324, rs4435429, rs4445746, rs4466940, rs4468448, rs4483642, rs4565951, rs4578835, rs4634524, rs4799760, rs4809955, rs4811492, rs496486, rs552994, rs6015147, rs6025923, rs6025927, rs6091820, rs6097782, rs6097790, rs6097793, rs6097797, rs6097801, rs6123749, rs6543934, rs6558102, rs656975, rs657302, rs6584894, rs660075, rs6713772, rs6909321, rs6971202, rs702355, rs7080507, rs7086707, rs7093143, rs7178587, rs7180867, rs7232734, rs7238006, rs7244801, rs7317000, rs751370, rs752979, rs7619350, rs7633210, rs7714122, rs7789703, rs7803164, rs7806265, rs7916897, rs7955917, rs7963693, rs8099595, rs8118441, rs844602, rs844608, rs844610, rs844612, rs844626, rs860722, rs873216, rs884266, rs894857, rs913882, rs9315048, rs9332420, rs933863, rs933864, rs9378319, rs9378684, rs9392358, rs9405541, rs9405546, rs947603, rs948029, rs948032, rs949298, rs9508834, rs9944913, rs9952995, and rs998051 (hereinafter Group 1), ii. identifying the subject as a predicted responder to glatiramer acetate if the genotype is AA at rs10214633, rs10277267, rs10935015, rs10935019, rs10988087, rs11081859, rs11694344, rs12256889, rs12340584, rs12494606, rs1415557, rs17007730, rs17087180, rs17104665, rs17104742, rs17588454, rs17807327, rs1892974, rs2088713, rs214526, rs2374730, rs4255033, rs4306478, rs4343256, rs4344916, rs4435429, rs4578835, rs4809955, rs496486, rs6015147, rs6097790, rs6584894, rs6713772, rs6909321, rs702355, rs7086707, rs7180867, rs7317000, rs844608, rs844610, rs933863, rs9392358, rs948029, or rs9508834 (hereinafter Group 2), AT at rs12524041 or rs7806265, AG at rs10277267, rs10950359, rs11599624, rs13245980, rs1415557, rs2521643, rs4255033, rs6584894, rs6909321, rs702355, or rs844626, AC at rs12256889, rs1229542, rs214526, rs6097793, rs7086707, rs7180867, rs844608, or rs844610, TT at rs1007328, rs10931091, rs11617134, rs11709339, rs11719825, rs11761457, rs1229553, rs1234567, rs1234947, rs12532459, rs12593600, rs1264423, rs13042992, rs1320648, rs1538123, rs1591661, rs17134651, rs17666347, rs17771939, rs2461319, rs2508806, rs2722396, rs2722398, rs2895215, rs401618, rs4369324, rs4483642, rs4565951, rs4811492, rs552994, rs6025923, rs6025927, rs6097797, rs657302, rs7232734, rs751370, rs7633210, rs7714122, rs7803164, rs7806265, rs7916897, rs8118441, rs844612, rs9378319, or rs9952995 (hereinafter Group 3), GT at rs12532459, rs2722398, rs4369324, or rs7093143, CT at rs10950371, rs11761457, rs1229562, rs12529764, rs13021482, rs13238613, rs1538123, rs1591661, rs1611185, rs17807445, rs1941973, rs2461319, rs2685484, rs2895215, rs4634524, rs4799760, rs6097797, rs7080507, rs7238006, rs7789703, rs7803164, rs844612, or rs947603, GG at rs10083547, rs10136012, rs10950359, rs11599624, rs12055694, rs1229558, rs1237625, rs12496278, rs12540494, rs12633010, rs12637073, rs1282540, rs1282546, rs12968586, rs1299325, rs13245980, rs16999008, rs17104665, rs17104742, rs2033471, rs2155262, rs2487889, rs2487896, rs2511064, rs2521643, rs2530121, rs2530123, rs28861531, rs3135391, rs4148871, rs4289164, rs4445746, rs6097801, rs6543934, rs6558102, rs656975, rs6971202, rs7093143, rs7244801, rs752979, rs7619350, rs7955917, rs844626, rs873216, rs894857, rs9315048, rs9332420, rs933864, rs948032, rs949298, or rs998051 (hereinafter Group 4), CG at rs11618546 or rs860722, or CC at rs1041897, rs10853605, rs10935016, rs10950371, rs11009827, rs11009835, rs11618546, rs11907046, rs1229542, rs1229555, rs1229562, rs1229563, rs1229564, rs1229568, rs12488259, rs12639443, rs13021482, rs13238613, rs1573706, rs1683691, rs17575455, rs17807445, rs2177073, rs2187495, rs2277431, rs2521644, rs2685484, rs2937395, rs4281882, rs4466940, rs4468448, rs4634524, rs4799760, rs6091820, rs6097782, rs6097793, rs6123749, rs660075, rs7080507, rs7789703, rs7963693, rs8099595, rs844602, rs860722, rs884266, rs913882, rs9378684, rs9405541, rs9405546, rs947603, or rs9944913 (hereinafter Group 5); and iii. administering the pharmaceutical composition comprising glatiramer acetate and a pharmaceutically acceptable carrier to the subject only if the subject is identified as a predicted responder to glatiramer acetate.

The invention also provides a method of identifying a human subject afflicted with multiple sclerosis or a single clinical attack consistent with multiple sclerosis as a predicted responder or as a predicted non-responder to glatiramer acetate, the method comprising determining the genotype of the subject at one or more single nucleotide polymorphisms (SNPs) selected from the group consisting of the SNPs in Group 1, wherein the subject is identified as a predicted responder to glatiramer acetate if the genotype is AA at one of the SNPs in Group 2, AT at rs12524041 or rs7806265, AG at rs10277267, rs10950359, rs11599624, rs13245980, rs1415557, rs2521643, rs4255033, rs6584894, rs6909321, rs702355, or rs844626, AC at rs12256889, rs1229542, rs214526, rs6097793, rs7086707, rs7180867, rs844608, or rs844610, TT at one of the SNPs in Group 3, GT at rs12532459, rs2722398, rs4369324, or rs7093143, CT at rs10950371, rs11761457, rs1229562, rs12529764, rs13021482, rs13238613, rs1538123, rs1591661, rs1611185, rs17807445, rs1941973, rs2461319, rs2685484, rs2895215, rs4634524, rs4799760, rs6097797, rs7080507, rs7238006, rs7789703, rs7803164, rs844612, or rs947603, GG at one of the SNPs in Group 4, CG at rs11618546 or rs860722, or CC one of the SNPs in Group 5; and wherein the subject is identified as a predicted non-responder to glatiramer acetate if the genotype is AA at rs1040194, rs10935016, rs10950359, rs11009827, rs11599624, rs12055694, rs1229542, rs1229558, rs1237625, rs12488259, rs12540494, rs12637073, rs1282540, rs1282546, rs12968586, rs13245980, rs16999008, rs17575455, rs2177073, rs2511064, rs2521643, rs4281882, rs4289164, rs4445746, rs4811492, rs6097793, rs6097801, rs6558102, rs7244801, rs7619350, rs7806265, rs7955917, rs844626, rs873216, rs894857, rs9332420, or rs948032 (hereinafter Group 6), AG at rs1040194, rs10935015, rs10935019, rs10988087, rs11081859, rs12055694, rs1229558, rs12340584, rs1237625, rs12494606, rs12540494, rs12637073, rs1282540, rs1282546, rs12968586, rs16999008, rs17007730, rs17087180, rs17104665, rs17104742, rs17588454, rs2374730, rs2487889, rs2487896, rs2511064, rs3135391, rs3742228, rs4148871, rs4343256, rs4445746, rs4809955, rs6097801, rs6713772, rs7244801, rs7619350, rs7955917, rs894857, rs933863, rs9392358, or rs9508834, AC at rs10214633, rs10935016, rs11009827, rs12488259, rs2088713, rs2177073, rs4306478, rs496486, rs6097790, or rs7317000, TT at rs10136012, rs1041897, rs10853605, rs10950371, rs11009835, rs11907046, rs1229555, rs1229562, rs1229563, rs1229564, rs1229568, rs12639443, rs13238613, rs1573706, rs1683691, rs1892974, rs2187495, rs2277431, rs2521644, rs2530121, rs2530123, rs2685484, rs2937395, rs35831078, rs4466940, rs4468448, rs4634524, rs6091820, rs6097782, rs6543934, rs660075, rs7789703, rs8099595, rs884266, rs913882, rs9378684, rs9405541, rs9405546, rs947603, rs948029, or rs9944913 (hereinafter Group 7), GT at rs11719825, rs13042992, rs1886308, rs2305623, or rs998051, CT at rs1041897, rs10931091, rs11009835, rs11617134, rs11709339, rs1229553, rs1229555, rs1229563, rs1229564, rs1229568, rs1234567, rs1234947, rs12593600, rs12639443, rs1320648, rs1573706, rs1683691, rs17134651, rs17666347, rs2187495, rs2277431, rs2508806, rs2937395, rs35831078, rs4466940, rs4468448, rs4483642, rs4565951, rs552994, rs6091820, rs6097782, rs657302, rs660075, rs7232734, rs7714122, rs8099595, rs9378319, rs9378684, rs9405541, rs9405546, rs9944913, or rs9952995, GG at rs10277267, rs10935015, rs10935019, rs10988087, rs11081859, rs11618546, rs11719825, rs12340584, rs12494606, rs12532459, rs13042992, rs17007730, rs17087180, rs17588454, rs1886308, rs2305623, rs2722398, rs3742228, rs4255033, rs4343256, rs4369324, rs4435429, rs4578835, rs4809955, rs6123749, rs6584894, rs6713772, rs7916897, rs7963693, rs9392358, or rs9508834 (hereinafter Group 8), CG at rs10083547, rs12496278, rs1299325, rs2155262, rs28861531, rs656975, rs7963693, or rs933864, or CC at rs1007328, rs10083547, rs10214633, rs10931091, rs11617134, rs11694344, rs11709339, rs11761457, rs12256889, rs1229553, rs1234567, rs1234947, rs12496278, rs12593600, rs1299325, rs1320648, rs1538123, rs1591661, rs1611185, rs17134651, rs17666347, rs17771939, rs17807327, rs1941973, rs214526, rs2461319, rs2508806, rs2722398, rs28861531, rs2895215, rs4306478, rs4344916, rs496486, rs552994, rs6015147, rs6025923, rs6025927, rs6097790, rs6097797, rs656975, rs657302, rs7178587, rs7232734, rs7238006, rs7317000, rs751370, rs7714122, rs7803164, rs844608, rs844610, rs844612, rs9378319, or rs9952995 (hereinafter Group 9);

and thereby identifying the subject as a predicted responder or as a predicted non-responder to glatiramer acetate.

The invention also provides a method for treating a human subject afflicted with multiple sclerosis or a single clinical attack consistent with multiple sclerosis comprising the steps of:

(i) administering to the human subject a therapeutic amount of a pharmaceutical composition comprising glatiramer and a pharmaceutically acceptable carrier;

(ii) identifying whether the human subject is a predicted responder to glatiramer acetate by determining the genotype of the subject at one or more single nucleotide polymorphisms (SNPs) selected from the group consisting of the SNPs in Group 1, wherein the subject is identified as a predicted responder to glatiramer acetate if the genotype is AA at one of the SNPs in Group 2, AT at rs12524041 or rs7806265, AG at rs10277267, rs10950359, rs11599624, rs13245980, rs1415557, rs2521643, rs4255033, rs6584894, rs6909321, rs702355, or rs844626, AC at rs12256889, rs1229542, rs214526, rs6097793, rs7086707, rs7180867, rs844608, or rs844610, TT one of the SNPs in Group 3, GT at rs12532459, rs2722398, rs4369324, rs7093143, CT at rs10950371, rs11761457, rs1229562, rs12529764, rs13021482, rs13238613, rs1538123, rs1591661, rs1611185, rs17807445, rs1941973, rs2461319, rs2685484, rs2895215, rs4634524, rs4799760, rs6097797, rs7080507, rs7238006, rs7789703, rs7803164, rs844612, or rs947603, GG at one of the SNPs in Group 4, CG at rs11618546 or rs860722, or CC at one of the SNPs in Group 5; and (iii) continuing administration of the pharmaceutical composition if the human subject is identified as a predicted responder to glatiramer acetate, or modifying the administration of the pharmaceutical composition to the human subject if the human subject is not identified as a predicted responder to glatiramer acetate.

The invention also provides a kit for identifying a human subject afflicted with multiple sclerosis or a single clinical attack consistent with multiple sclerosis as a predicted responder or as a predicted non-responder to glatiramer acetate, the kit comprising (i) at least one probe specific for a SNP selected from the group consisting of the SNPs in Group 1.

The invention also provides a kit for identifying a human subject afflicted with multiple sclerosis or a single clinical attack consistent with multiple sclerosis as a predicted responder or as a predicted non-responder to glatiramer acetate, the kit comprising at least one pair of PCR primers designed to amplify a DNA segment which includes a SNP selected from the group consisting of the SNPs in Group 1.

The invention also provides a PCR amplification kit comprising (i) at least one pair of PCR primers designed to amplify a DNA segment which includes a SNP selected from the group consisting of the SNPs in Group 1, and (ii) instructions for use of the PCR primers to amplify the segment of DNA.

The invention also provides a kit for identifying a human subject afflicted with multiple sclerosis or a single clinical attack consistent with multiple sclerosis as a predicted responder or as a predicted non-responder to glatiramer acetate, the kit comprising a reagent for performing a method selected from the group consisting of restriction fragment length polymorphism (RFLP) analysis, sequencing, single strand conformation polymorphism analysis (SSCP), chemical cleavage of mismatch (CCM), gene chip and denaturing high performance liquid chromatography (DHPLC) for determining the identity of at least one SNP selected from the group consisting of The SNPs in Group 1.

The invention also provides a kit for identifying a human subject afflicted with multiple sclerosis or a single clinical attack consistent with multiple sclerosis as a predicted responder or as a predicted non-responder to glatiramer acetate, the kit comprising reagents for TaqMan Open Array assay designed for determining the identity of at least one SNP selected from the group consisting of The SNPs in Group 1.

The invention also provides a probe for identifying the genotype of a SNP selected from the group consisting of the SNPs in Group 1.

DETAILED DESCRIPTION OF THE INVENTION

Figure 1:
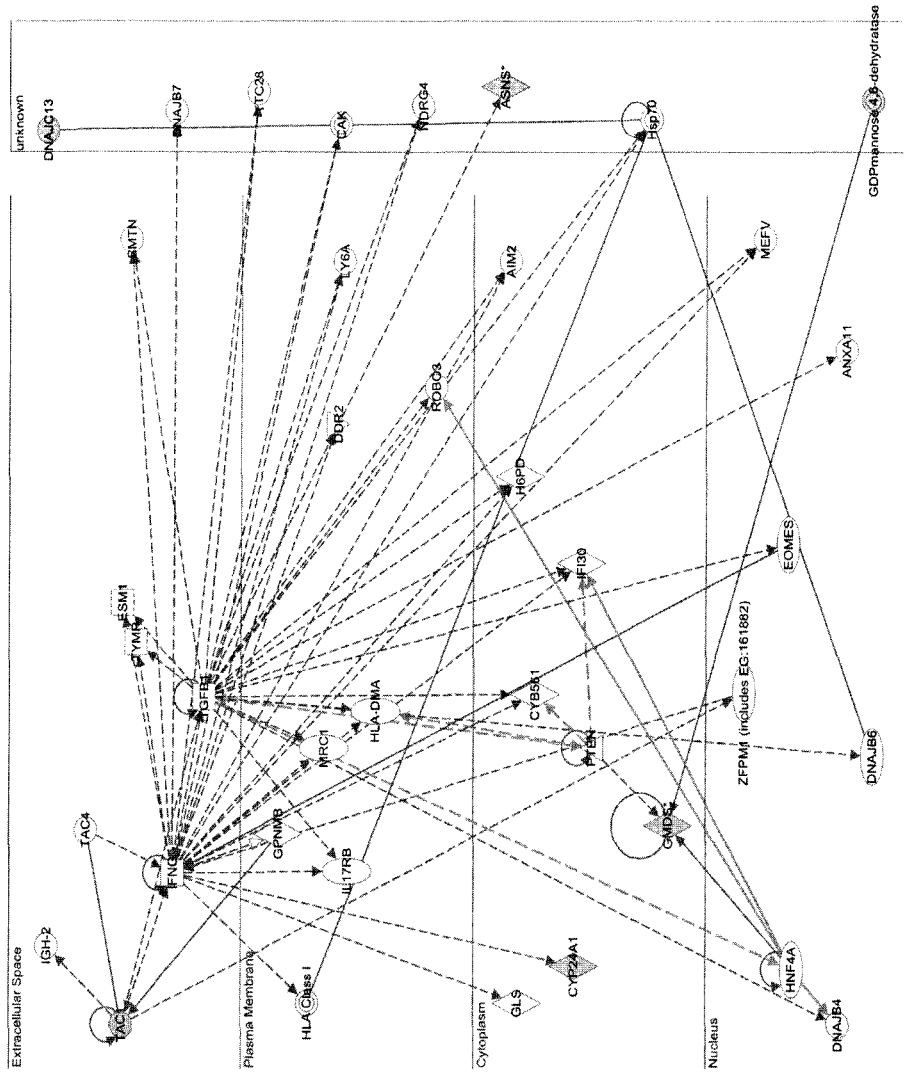
FIG. 1. Merging of the two mostly enriched networks for broad phenotype definition (organized by cellular compartment). Genes with the light grey symbols are from the GWAS findings, while the others with "empty" symbols are their pathways' specific members, and have not been identified by any GWAS.

This invention provides a method for treating a human subject afflicted with multiple sclerosis or a single clinical attack consistent with multiple sclerosis with a pharmaceutical composition comprising glatiramer acetate and a pharmaceutically acceptable carrier, comprising the steps of:
  i. determining a genotype of the subject at one or more single nucleotide polymorphisms (SNPs) selected from the group consisting of: the SNPs in Group 1,
  ii. identifying the subject as a predicted responder to glatiramer acetate if the genotype is
    AA at one of the SNPs in Group 2,
    AT at rs12524041 or rs7806265,
    AG at rs10277267, rs10950359, rs11599624, rs13245980, rs1415557, rs2521643, rs4255033, rs6584894, rs6909321, rs702355, or rs844626,
    AC at rs12256889, rs1229542, rs214526, rs6097793, rs7086707, rs7180867, rs844608, or rs844610,
    TT at one of the SNPs in Group 3,
    GT at rs12532459, rs2722398, rs4369324, or rs7093143,
    CT at rs10950371, rs11761457, rs1229562, rs12529764, rs13021482, rs13238613, rs1538123, rs1591661, rs1611185, rs17807445, rs1941973, rs2461319, rs2685484, rs2895215, rs4634524, rs4799760, rs6097797, rs7080507, rs7238006, rs7789703, rs7803164, rs844612, or rs947603,
    GG at one of the SNPs in Group 4,
    CG at rs11618546 or rs860722, or
    CC at one of the SNPs in Group 5; and
  iii. administering the pharmaceutical composition comprising glatiramer acetate and a pharmaceutically acceptable carrier to the subject only if the subject is identified as a predicted responder to glatiramer acetate.

In some embodiments, administering the pharmaceutical composition comprising glatiramer acetate and a pharmaceutically acceptable carrier comprises administering to the human subject three subcutaneous injections of the pharmaceutical composition over a period of seven days with at least one day between every subcutaneous injection.

In some embodiments, the pharmaceutical composition is a unit dose of a 1 ml aqueous solution comprising 40 mg of glatiramer acetate.

In some embodiments, the pharmaceutical composition is a unit dose of a 1 ml aqueous solution comprising 20 mg of glatiramer acetate.

In some embodiments, the pharmaceutical composition is a unit dose of a 0.5 ml aqueous solution comprising 20 mg of glatiramer acetate.

The invention also provides a method of identifying a human subject afflicted with multiple sclerosis or a single clinical attack consistent with multiple sclerosis as a predicted responder or as a predicted non-responder to glatiramer acetate, the method comprising determining the genotype of the subject at one or more single nucleotide polymorphisms (SNPs) selected from the group consisting of the SNPs in Group 1,
wherein the subject is identified as a predicted responder to glatiramer acetate if the genotype is
  AA at one of the SNPs in Group 2,
  AT at rs12524041 or rs7806265,
  AG at rs10277267, rs10950359, rs11599624, rs13245980, rs1415557, rs2521643, rs4255033, rs6584894, rs6909321, rs702355, or rs844626,
  AC at rs12256889, rs1229542, rs214526, rs6097793, rs7086707, rs7180867, rs844608, or rs844610,
  TT at one of the SNPs in Group 3,
  GT at rs12532459, rs2722398, rs4369324, or rs7093143,
  CT at rs10950371, rs11761457, rs1229562, rs12529764, rs13021482, rs13238613, rs1538123, rs1591661, rs1611185, rs17807445, rs1941973, rs2461319, rs2685484, rs2895215, rs4634524, rs4799760, rs6097797, rs7080507, rs7238006, rs7789703, rs7803164, rs844612, or rs947603,
  GG at one of the SNPs in Group 4,
  CG at rs11618546 or rs860722, or
  CC at one of the SNPs in Group 5; and
wherein the subject is identified as a predicted non-responder to glatiramer acetate if the genotype is
  AA at one of the SNPs in Group 6,
  AG at rs1040194, rs10935015, rs10935019, rs10988087, rs11081859, rs12055694, rs1229558, rs12340584, rs1237625, rs12494606, rs12540494, rs12637073, rs1282540, rs1282546, rs12968586, rs16999008, rs17007730, rs17087180, rs17104665, rs17104742, rs17588454, rs2374730, rs2487889, rs2487896, rs2511064, rs3135391, rs3742228, rs4148871, rs4343256, rs4445746, rs4809955, rs6097801, rs6713772, rs7244801, rs7619350, rs7955917, rs894857, rs933863, rs9392358, or rs9508834,
  AC at rs10214633, rs10935016, rs11009827, rs12488259, rs2088713, rs2177073, rs4306478, rs496486, rs6097790, or rs7317000,
  TT at one of the SNPs in Group 7,
  GT at rs11719825, rs13042992, rs1886308, rs2305623, or rs998051,
  CT at rs1041897, rs10931091, rs11009835, rs11617134, rs11709339, rs1229553, rs1229555, rs1229563, rs1229564, rs1229568, rs1234567, rs1234947, rs12593600, rs12639443, rs1320648, rs1573706, rs1683691, rs17134651, rs17666347, rs2187495, rs2277431, rs2508806, rs2937395, rs35831078, rs4466940, rs4468448, rs4483642, rs4565951, rs552994, rs6091820, rs6097782, rs657302, rs660075, rs7232734, rs7714122, rs8099595, rs9378319, rs9378684, rs9405541, rs9405546, rs9944913, or rs9952995,
  GG at one of the SNPs in Group 8,
  CG at rs10083547, rs12496278, rs1299325, rs2155262, rs28861531, rs656975, rs7963693, or rs933864, or
  CC at one of the SNPs in Group 9;
and thereby identifying the subject as a predicted responder or as a predicted non-responder to glatiramer acetate.

The invention also provides a method for treating a human subject afflicted with multiple sclerosis or a single clinical attack consistent with multiple sclerosis comprising the steps of:

(i) administering to the human subject a therapeutic amount of a pharmaceutical composition comprising glatiramer acetate and a pharmaceutically acceptable carrier;
(ii) identifying whether the human subject is a predicted responder to glatiramer acetate by determining the genotype of the subject at one or more single nucleotide polymorphisms (SNPs) selected from the group consisting of the SNPs in Group 1,
  wherein the subject is identified as a predicted responder to glatiramer acetate if the genotype is
  AA at one of the SNPs in Group 2,
  AT at rs12524041 or rs7806265,
  AG at rs10277267, rs10950359, rs11599624, rs13245980, rs1415557, rs2521643, rs4255033, rs6584894, rs6909321, rs702355, or rs844626,
  AC at rs12256889, rs1229542, rs214526, rs6097793, rs7086707, rs7180867, rs844608, or rs844610,
  TT at one of the SNPs in Group 3,
  GT at rs12532459, rs2722398, rs4369324, or rs7093143,
  CT at rs10950371, rs11761457, rs1229562, rs12529764, rs13021482, rs13238613, rs1538131, rs1591661, rs1611185, rs17807445, rs1941973, rs2461319, rs2685484, rs2895215, rs4634524, rs4799760, rs6097797, rs7080507, rs7238006, rs7789703, rs7803164, rs844612, or rs947603,
  GG at one of the SNPs in Group 4,
  CG at rs11618546 or rs860722, or
  CC at one of the SNPs in Group 5; and
(iii) continuing administration of the pharmaceutical composition if the human subject is identified as a predicted responder to glatiramer acetate, or modifying the administration of the pharmaceutical composition to the human subject if the human subject is not identified as a predicted responder to glatiramer acetate.

In some embodiments, administering to the human subject a therapeutic amount of a pharmaceutical composition comprising glatiramer acetate and a pharmaceutically acceptable carrier comprises administering to the human subject three subcutaneous injections of the pharmaceutical composition over a period of seven days with at least one day between every subcutaneous injection.

In some embodiments, the pharmaceutical composition is a unit dose of a 1 ml aqueous solution comprising 40 mg of glatiramer acetate.

In some embodiments, the pharmaceutical composition is a unit dose of a 1 ml aqueous solution comprising 20 mg of glatiramer acetate.

In some embodiments, the pharmaceutical composition is a unit dose of a 0.5 ml aqueous solution comprising 20 mg of glatiramer acetate.

In some embodiments, if the human subject is identified as a predicted responder to glatiramer acetate, the human subject is thereafter administered the pharmaceutical composition comprising glatiramer acetate and a pharmaceutically acceptable carrier as monotherapy.

In some embodiments, if the human subject is identified as a predicted responder to glatiramer acetate, the human subject is thereafter administered the pharmaceutical composition comprising glatiramer acetate and a pharmaceutically acceptable carrier in combination with at least one other multiple sclerosis drug.

In some embodiments, the genotype is determined at one or more single nucleotide polymorphisms (SNPs) selected from the group consisting of rs947603, rs1007328, rs1573706, rs2177073, rs2487896, rs2511064, rs2521644, rs3135391, rs4148871, rs4343256, rs4344916, rs4369324, rs4445746, rs6097801, rs9508834, rs9944913, rs10853605, rs10931091, rs10950359, rs10988087, rs11599624, rs11617134, rs12256889, rs12639443, rs13042992, rs13238613, rs17087180, rs17575455, rs17771939 and rs17807327.

In some embodiments, the genotype is determined at one or more single nucleotide polymorphisms (SNPs) selected from the group consisting of rs9508834, rs17807327, rs4344916, rs12639443, rs17087180 and rs17771939.

In some embodiments, the genotype is determined at one or more single nucleotide polymorphisms (SNPs) selected from the group consisting of rs4344916, rs12639443, rs17087180 and rs17771939.

In some embodiments, the genotype is determined at SNPs rs4344916, rs12639443, rs17087180 and rs17771939. In other embodiments the genotype is further determined at SNPs rs9508834 or rs17807327. In other embodiments the genotype is further determined at SNPs rs9508834 and rs17807327.

In some embodiments, the method comprises determining the genotype of the subject at 1, 2, 3, 4, 5, 6, 7, 8, 9, 10, 11, 12, 13, 14 or more of said SNPs.

In some embodiments, the method comprises determining the genotype of the subject at 4, 6, 10, 11, 12 or 13 of said SNPs.

In some embodiments, the method comprises determining the genotype of the subject at 6 or 8 of said SNPs.

In some embodiments, the method comprises determining the genotype of the subject at 6 SNPs.

In some embodiments, the genotype is determined at SNPs rs2521644, rs12256889, rs214526, rs17771939, rs496486, and rs949298.

In some embodiments, a score is assigned to each genotype of each SNP, for the purpose of determining if the human subject is a predicted responder to glatiramer acetate, wherein the scores are approximately as shown in tables 7a-f.

In some embodiments, the genotype is determined at SNPs rs2521644, rs12256889, rs214526, rs17771939, rs496486, and rs2511064.

In some embodiments, a score is assigned to each genotype of each SNP, for the purpose of determining if the human subject is a predicted responder to glatiramer acetate, wherein the scores are approximately as shown in tables 9a-f.

In some embodiments, a relative weight is assigned to each SNP, for the purpose of determining if the human subject is a predicted responder to glatiramer acetate, wherein the relative weight is approximately as shown in table 10.

In some embodiments, the genotype is determined at SNPs rs12256889, rs17771939, rs2511064, and rs2521644.

In some embodiments, a score is assigned to each genotype of each SNP, for the purpose of determining if the human subject is a predicted responder to glatiramer acetate, wherein the scores are approximately as shown in tables 9a-f.

In some embodiments, a relative weight is assigned to each SNP, for the purpose of determining if the human subject is a predicted responder to glatiramer acetate, wherein the relative weight is approximately as shown in table 11.

In some embodiments, the genotype is determined at SNPs rs11599624, rs12639443, rs13042992, rs13238613, rs17087180, rs17771939, rs17807327, rs2487896, rs3135391, rs4148871, rs4343256, rs4344916, and rs9508834.

In some embodiments, the genotype is determined at SNPs rs12256889, rs12639443, rs13238613, rs1573706, rs17087180, rs17771939, rs17807327, rs2487896, rs4343256, rs4344916, rs4369324, rs4445746, and rs9944913.

In some embodiments, the genotype is determined at SNPs rs10988087, rs12639443, rs13042992, rs13238613, rs1573706, rs17087180, rs17771939, rs17807327, rs4148871, rs4344916, rs6097801, and rs9508834.

In some embodiments, the genotype is determined at SNPs rs10988087, rs12256889, rs12639443, rs17087180, rs17771939, rs2177073, rs2521644, rs4344916, rs4369324, rs6097801, rs9508834, and rs9944913.

In some embodiments, the genotype is determined at SNPs rs10988087, rs11617134, rs12639443, rs13042992, rs17087180, rs17771939, rs17807327, rs2487896, rs4148871, rs4344916, rs4445746, rs6097801, and rs9508834.

In some embodiments, the genotype is determined at SNPs rs10988087, rs11617134, rs12639443, rs13042992, rs17087180, rs17771939, rs17807327, rs2487896, rs2521644, rs4148871, rs4344916, rs4445746, and rs6097801.

In some embodiments, the genotype is determined at SNPs rs10988087, rs12256889, rs12639443, rs17087180, rs17771939, rs17807327, rs2487896, rs4148871, rs4344916, rs6097801, and rs9508834.

In some embodiments, the genotype is determined at SNPs rs1007328, rs11617134, rs12639443, rs13238613, rs1573706, rs17087180, rs17771939, rs17807327, rs4343256, rs4344916, rs9508834, and rs9944913.

In some embodiments, the genotype is determined at SNPs rs12639443, rs17087180, rs17771939, rs17807327, rs2487896, rs4148871, rs4343256, rs4344916, rs4369324, rs4445746, rs6097801, rs9508834, and rs9944913.

In some embodiments, the genotype is determined at SNPs rs11617134, rs12639443, rs17087180, rs17771939, rs17807327, rs2487896, rs3135391, rs4148871, rs4344916, rs4369324, rs6097801, rs9508834, and rs9944913.

In some embodiments, the genotype is determined at SNPs rs10988087, rs12639443, rs13238613, rs17087180, rs17771939, rs2487896, rs4148871, rs4343256, rs4344916, and rs9508834.

In some embodiments, the genotype is determined at SNPs rs11617134, rs12256889, rs12639443, rs13042992, rs17087180, rs17771939, rs17807327, rs2177073, rs2487896, rs4343256, rs4344916, rs6097801, and rs9508834.

In some embodiments, the genotype is determined at SNPs rs10950359, rs11617134, rs12639443, rs17087180, rs17771939, rs2487896, rs2511064, rs3135391, rs4148871, rs4343256, rs4344916, rs9508834, and rs9944913.

In some embodiments, the genotype is determined at SNPs rs12256889, rs12639443, rs13042992, rs17087180, rs17771939, rs17807327, rs2487896, rs2521644, rs4344916, and rs6097801.

In some embodiments, the genotype is determined at SNPs rs10950359, rs10988087, rs11599624, rs12256889, rs12639443, rs13042992, rs17087180, rs17771939, rs17807327, rs2521644, rs3135391, rs4344916, and rs9508834.

In some embodiments, the genotype is determined at SNPs rs1007328, rs10950359, rs12256889, rs12639443, rs13042992, rs1573706, rs17087180, rs17771939, rs17807327, rs4343256, rs4344916, rs947603, and rs9508834.

In some embodiments, the genotype is determined at SNPs rs11599624, rs12256889, rs12639443, rs1573706, rs17087180, rs17771939, rs17807327, rs2177073, rs2487896, rs4344916, rs6097801, rs9508834, and rs9944913.

In some embodiments, the method further comprises the measurement of at least one clinical variable which is indicative of response or non-response to glatiramer acetate therapy.

In some embodiments, the at least one clinical variable is selected from age of the subject and T1 brain lesion volume.

In some embodiments, the method further comprises measuring the value of a biomarker in the blood of the human subject.

In some embodiments, the biomarker is selected from the group consisting of IL-10 concentration, IL-17 concentration, IL-18 concentration, TNF-α concentration, brain-derived neurotrophic factor concentration, caspase-1 concentration, IL-10/IL-18 ratio, IL-10/IL-17 ratio, IL-2 concentration and IFN-γ concentration, or a combination thereof.

In some embodiments, the genotype is determined from a nucleic acid-containing sample that has been obtained from the subject.

In some embodiments, the genotype is determined using an array.

In some embodiments, the array is selected from the group consisting of a gene array, a gene chip, a DNA array, a DNA microarray, a TAqMan Open Array and a bead array.

In some embodiments, the array is a TaqMan Open Array.

In some embodiments, determining the genotype comprises using a method selected from the group consisting of restriction fragment length polymorphism (RFLP) analysis, sequencing, single strand conformation polymorphism analysis (SSCP), chemical cleavage of mismatch (CCM), denaturing high performance liquid chromatography (DHPLC), Polymerase Chain Reaction (PCR) and an array, or a combination thereof.

In some embodiments, the genotype is determined using at least one pair of PCR primers and at least one probe.

In some embodiments, the genotype is determined by a method selected from the group consisting of restriction fragment length polymorphism (RFLP) analysis, sequencing, single strand conformation polymorphism analysis (SSCP), chemical cleavage of mismatch (CCM), gene chip, and denaturing high performance liquid chromatography (DHPLC).

In some embodiments, determining the genotype of the subject at said one or more SNP comprises:
  (i) obtaining DNA from a sample that has been obtained from the subject;
  (ii) optionally amplifying the DNA; and
  (iii) contacting the DNA or the amplified DNA with an array comprising a plurality of probes suitable for determining the identity of the one or more SNPs.

In some embodiments, determining the genotype of the subject at said one or more SNPs comprises:
  (i) obtaining DNA from a sample that has been obtained from the subject;
  (ii) optionally amplifying the DNA; and
  (iii) subjecting the DNA or the amplified DNA to a method selected from the group consisting of restriction fragment length polymorphism (RFLP) analysis, sequencing, single strand conformation polymorphism analysis (SSCP), chemical cleavage of mismatch (CCM), gene chip, denaturing high performance liquid chromatography (DHPLC) and an array, or a combination thereof for determining the identity the one or more SNPs.

In some embodiments, the array comprises a plurality of probes suitable for determining the identity of the one or more SNPs.

In some embodiments, the human subject is a naive patient.

In some embodiments, the human subject has been previously administered glatiramer acetate.

In some embodiments, the human subject has been previously administered a multiple sclerosis drug other than glatiramer acetate.

In some embodiments, the genotype of the subject at said one or more SNPs is obtained indirectly by determining the genotype of the subject at a SNP that is in linkage disequilibrium with said one or more SNPs.

The invention also provides a kit for identifying a human subject afflicted with multiple sclerosis or a single clinical attack consistent with multiple sclerosis as a predicted responder or as a predicted non-responder to glatiramer acetate, the kit comprising at least one probe specific for a SNP selected from the group consisting of the SNPs in Group 1.

The invention also provides a kit for identifying a human subject afflicted with multiple sclerosis or a single clinical attack consistent with multiple sclerosis as a predicted responder or as a predicted non-responder to glatiramer acetate, the kit comprising at least one pair of PCR primers designed to amplify a DNA segment which includes a SNP selected from the group consisting of the SNPs in Group 1.

The invention also provides a PCR amplification kit comprising
(i) at least one pair of PCR primers designed to amplify a DNA segment which includes a SNP selected from the group consisting of the SNPs in Group 1, and
(ii) instructions for use of the PCR primers to amplify the segment of DNA.

The invention also provides a kit for identifying a human subject afflicted with multiple sclerosis or a single clinical attack consistent with multiple sclerosis as a predicted responder or as a predicted non-responder to glatiramer acetate, the kit comprising a reagent for performing a method selected from the group consisting of restriction fragment length polymorphism (RFLP) analysis, sequencing, single strand conformation polymorphism analysis (SSCP), chemical cleavage of mismatch (CCM), gene chip and denaturing high performance liquid chromatography (DHPLC) for determining the identity of at least one SNP selected from the group consisting of the SNPs of Group 1.

In some embodiments, the kit comprises
(i) at least one pair of PCR primers designed to amplify a DNA segment which includes a SNP selected from the group consisting of the SNPs of Group 1, and
(ii) at least one probe specific for a SNP selected from the group consisting of the SNPs of Group 1.

The invention also provides a kit for identifying a human subject afflicted with multiple sclerosis or a single clinical attack consistent with multiple sclerosis as a predicted responder or as a predicted non-responder to glatiramer acetate, the kit comprising reagents for TaqMan Open Array assay designed for determining the identity of at least one SNP selected from the group consisting of The SNPs of Group 1.

In some embodiments the kit further comprises instructions for use of the kit for identifying a human subject afflicted with multiple sclerosis or a single clinical attack consistent with multiple sclerosis as a predicted responder or as a predicted non-responder to glatiramer acetate.

In some embodiments, the one or more single nucleotide polymorphisms (SNPs) is selected from the group consisting of rs947603, rs1007328, rs1573706, rs2177073, rs2487896, rs2511064, rs2521644, rs3135391, rs4148871, rs4343256, rs4344916, rs4369324, rs4445746, rs6097801, rs9508834, rs9944913, rs10853605, rs10931091, rs10950359, rs10988087, rs11599624, rs11617134, rs12256889, rs12639443, rs13042992, rs13238613, rs17087180, rs17575455, rs17771939 and rs17807327.

In some embodiments, the one or more single nucleotide polymorphisms (SNPs) is selected from the group consisting of rs9508834, rs17807327, rs4344916, rs12639443, rs17087180 and rs17771939.

In some embodiments, the one or more single nucleotide polymorphisms (SNPs) are selected from the group consisting of rs4344916, rs12639443, rs17087180 and rs17771939.

In some embodiments, the kit is designed to determine the genotype at SNPs rs9508834, rs17807327, rs4344916, rs12639443, rs17087180 and rs17771939.

In some embodiments, the kit is designed to determine the genotype at SNPs rs4344916, rs12639443, rs17087180 and rs17771939.

In some embodiments, the kit is designed to determine the genotype at SNPs rs2521644, rs12256889, rs214526, rs17771939, rs496486, and rs949298.

In some embodiments, the kit is designed to determine the genotype at SNPs rs2521644, rs12256889, rs214526, rs17771939, rs496486, and rs2511064.

In some embodiments, the kit is designed to determine the genotype at SNPs rs12256889, rs17771939, rs2511064, and rs2521644.

In some embodiments, the kit is designed to determine the genotype at SNPs rs11599624, rs12639443, rs13042992, rs13238613, rs17087180, rs17771939, rs17807327, rs2487896, rs3135391, rs4148871, rs4343256, rs4344916, and rs9508834.

In some embodiments, the kit is designed to determine the genotype at SNPs rs12256889, rs12639443, rs13238613, rs1573706, rs17087180, rs17771939, rs17807327, rs2487896, rs4343256, rs4344916, rs4369324, rs4445746, and rs9944913.

In some embodiments, the kit is designed to determine the genotype at SNPs rs10988087, rs12639443, rs13042992, rs13238613, rs1573706, rs17087180, rs17771939, rs17807327, rs4148871, rs4344916, rs6097801, and rs9508834.

In some embodiments, the kit is designed to determine the genotype at SNPs rs10988087, rs12256889, rs12639443, rs17087180, rs17771939, rs2177073, rs2521644, rs4344916, rs4369324, rs6097801, rs9508834, and rs9944913.

In some embodiments, the kit is designed to determine the genotype at SNPs rs10988087, rs11617134, rs12639443, rs13042992, rs17087180, rs17771939, rs17807327, rs2487896, rs4148871, rs4445746, rs6097801, and rs9508834.

In some embodiments, the kit is designed to determine the genotype at SNPs rs10988087, rs11617134, rs12639443, rs13042992, rs17087180, rs17771939, rs17807327, rs2487896, rs2521644, rs4148871, rs4344916, rs4445746, and rs6097801.

In some embodiments, the kit is designed to determine the genotype at SNPs rs10988087, rs12256889, rs12639443, rs17087180, rs17771939, rs17807327, rs2487896, rs4148871, rs4344916, rs6097801, and rs9508834.

In some embodiments, the kit is designed to determine the genotype at SNPs rs1007328, rs11617134, rs12639443, rs13238613, rs1573706, rs17087180, rs17771939, rs17807327, rs4343256, rs4344916, rs9508834, and rs9944913.

In some embodiments, the kit is designed to determine the genotype at SNPs rs12639443, rs17087180, rs17771939, rs17807327, rs2487896, rs4148871, rs4343256, rs4344916, rs4369324, rs4445746, rs6097801, rs9508834, and rs9944913.

In some embodiments, the kit is designed to determine the genotype at SNPs rs11617134, rs12639443, rs17087180, rs17771939, rs17807327, rs2487896, rs3135391, rs4148871, rs4344916, rs4369324, rs6097801, rs9508834, and rs9944913.

In some embodiments, the kit is designed to determine the genotype at SNPs rs10988087, rs12639443, rs13238613, rs17087180, rs17771939, rs2487896, rs4148871, rs4343256, rs4344916, and rs9508834.

In some embodiments, the kit is designed to determine the genotype at SNPs rs11617134, rs12256889, rs12639443, rs13042992, rs17087180, rs17771939, rs17807327, rs2177073, rs2487896, rs4343256, rs4344916, rs6097801, and rs9508834.

In some embodiments, the kit is designed to determine the genotype at SNPs rs10950359, rs11617134, rs12639443, rs17087180, rs17771939, rs2487896, rs2511064, rs3135391, rs4148871, rs4343256, rs4344916, rs9508834, and rs9944913.

In some embodiments, the kit is designed to determine the genotype at SNPs rs12256889, rs12639443, rs13042992, rs17087180, rs17771939, rs17807327, rs2487896, rs2521644, rs4344916, and rs6097801.

In some embodiments, the kit is designed to determine the genotype at SNPs rs10950359, rs10988087, rs11599624, rs12256889, rs12639443, rs13042992, rs17087180, rs17771939, rs17807327, rs2521644, rs3135391, rs4344916, and rs9508834.

In some embodiments, the kit is designed to determine the genotype at SNPs rs1007328, rs10950359, rs12256889, rs12639443, rs13042992, rs1573706, rs17087180, rs17771939, rs17807327, rs4343256, rs4344916, rs947603, and rs9508834.

In some embodiments, the kit is designed to determine the genotype at SNPs rs11599624, rs12256889, rs12639443, rs1573706, rs17087180, rs17771939, rs17807327, rs2177073, rs2487896, rs4344916, rs6097801, rs9508834, and rs9944913.

In some embodiments, a score is assigned to each genotype of each SNP, for the purpose of determining if the human subject is a predicted responder to glatiramer acetate, wherein the scores are approximately as shown in tables 18a-s and 19a-h.

In some embodiments, a relative weight is assigned to each SNP, for the purpose of determining if the human subject is a predicted responder to glatiramer acetate, wherein the relative weight is approximately as shown in one of tables 20-36, wherein the table selected corresponds to the SNPs at which a genotype was determined.

As used herein, a genetic marker refers to a DNA sequence that has a known location on a chromosome. Several non-limiting examples of classes of genetic markers include SNP (single nucleotide polymorphism), STR (short tandem repeat), and SFP (single feature polymorphism). VNTR (variable number tandem repeat), microsatellite polymorphism, insertions and deletions. The genetic markers associated with the invention are SNPs.

As used herein a SNP or "single nucleotide polymorphism" refers to a specific site in the genome where there is a difference in DNA base between individuals. In some embodiments the SNP is located in a coding region of a gene. In other embodiments the SNP is located in a noncoding region of a gene. In still other embodiments the SNP is located in an intergenic region.

Several non-limiting examples of databases from which information on SNPs or genes that are associated with human disease can be retrieved include: NCBI resources, The SNP Consortium LTD, NCBI dbSNP database, International HapMap Project, 1000 Genomes Project, Glovar Variation Browser, SNPStats, PharmGKB, GEN-SniP, and SNPedia.

In some embodiments, SNPs associated with the invention comprise one or more of the SNPs listed in Tables 1-3 or table 16. In some embodiments, multiple SNPs are evaluated simultaneously while in other embodiments SNPS are evaluated separately. SNPs are identified herein using the rs identifier numbers in accordance with the NCBI dbSNP database, which is publically available at: www.ncbi.nlm.nih.gov/projects/SNP/.

In some embodiments, SNPs in linkage disequilibrium with the SNPs found to be associated with response or non-response to GA are useful for obtaining similar results.

As used herein, linkage disequilibrium refers to the non-random association of SNPs at one loci. Techniques for the measurement of linkage disequilibrium are known in the art. As two SNPs are in linkage disequilibrium if they are inherited together, the information they provide is correlated to a certain extent. SNPs in linkage disequilibrium with the SNPs included in the models can be obtained from databases such as HapMap or other related databases, from experimental setups run in laboratories or from computer-aided in-silico experiments.

Determining the genotype of a subject at a position of SNP as specified herein, e.g. as specified by NCBI dbSNP rs identifier, may comprise directly genotyping, e.g. by determining the identity of the nucleotide of each allele at the locus of SNP, and/or indirectly genotyping, e.g. by determining the identity of each allele at one or more loci that are in linkage disequilibrium with the SNP in question and which allow one to infer the identity of each allele at the locus of SNP in question with a substantial degree of confidence.

In some cases, indirect genotyping may comprise determining the identity of each allele at one or more loci that are in sufficiently high linkage disequilibrium with the SNP in question so as to allow one to infer the identity of each allele at the locus of SNP in question with a probability of at least 85%, at least 90% or at least 99% certainty.

A genotype at a position of SNP (genotype "at a" SNP) may be represented by a single letter which corresponds to the identity of the nucleotide at the SNP, where A represents adenine, T represents thymine, C represents cytosine, and G represents guanine. The identity of two alleles at a single SNP may be represented by a two letter combination of A, T, C, and G, where the first letter of the two letter combination represents one allele and the second letter represents the second allele, and where A represents adenine, T represents thymine, C represents cytosine, and G represents guanine. Thus, a two allele genotype at a SNP can be represented as, for example, AA, AT, AG, AC, TT, TG, TC, GG, GC, or CC. It is understood that AT, AG, AC, TG, TC, and GC are equivalent to TA, GA, CA, GT, CT, and CG, respectively.

The SNPs of the invention can be used as predictive indicators of the response to GA in subjects afflicted with multiple sclerosis or a single clinical attack consistent with multiple sclerosis. Aspects of the invention relate to determining the presence of SNPs through obtaining a patient DNA sample and genotyping the patient sample at one or more SNPs, or at a certain set of SNPs. It should be appreciated that a patient DNA sample can be extracted, and a SNP can be detected in the sample, through any means known to one of ordinary skill in art. Some non-limiting examples of known techniques include detection via restriction fragment length polymorphism (RFLP) analysis, microarrays including but mot limited to planar microarrays or bead arrays, gene arrays, PCR arrays including TaqMan Open Array, sequencing, single strand conformation polymorphism analysis (SSCP), chemical cleavage of mismatch (CCM), and denaturing high performance liquid chromatography (DHPLC).

In some embodiments, a SNP is detected through PCR amplification and sequencing of the DNA region comprising the SNP.

In some embodiments, a SNP is detected through PCR amplification in the presence of a probe specific for a SNP.

Probes and methods for their use in detecting SNPs are well known in the art and are described, for example, in Barnes M R. Genetic Variation: Methods and Protocols 1st ed. New York: Humana Press, 2010 and Komar, A A. Single Nucleotide Polymorphisms: Methods and Protocols $2^{nd}$ ed. York: Humana Press, 2009.

In some embodiments SNPs are detected using DNA microarrays including DNA CHIPs. Microarrays for detection of genetic polymorphisms, changes or mutations (in general, genetic variations) such as a SNP in a DNA sequence, comprise a solid surface, typically glass, on which a high number of genetic sequences are deposited (the probes), complementary to the genetic variations to be studied. Using standard robotic printers to apply probes to the array a high density of individual probe features can be obtained, for example probe densities of 600 features per $cm^2$ or more can be typically achieved. The positioning of probes on an array is precisely controlled by the printing device (robot, inkjet printer, photolithographic mask etc) and probes are aligned in a grid. The organisation of probes on the array facilitates the subsequent identification of specific probe-target interactions.

Additionally it is common, but not necessary, to divide the array features into smaller sectors, also grid-shaped, that are subsequently referred to as sub-arrays. Sub-arrays typically comprise 32 individual probe features although lower (e.g. 16) or higher (e.g. 64 or more) features can comprise each subarray.

In some embodiments, detection of genetic variation such as the presence of a SNP involves hybridization to sequences which specifically recognize the normal and the mutant allele in a fragment of DNA derived from a test sample. Typically, the fragment has been amplified, e.g. by using the polymerase chain reaction (PCR), and labelled e.g. with a fluorescent molecule. A laser can be used to detect bound labelled fragments on the chip and thus an individual who is homozygous for the normal allele can be specifically distinguished from heterozygous individuals (in the case of autosomal dominant conditions then these individuals are referred to as carriers) or those who are homozygous for the mutant allele.

In some embodiments, the amplification reaction and/or extension reaction is carried out on the microarray or bead itself. For differential hybridization based methods there are a number of methods for analysing hybridization data for genotyping: Increase in hybridization level: The hybridization levels of probes complementary to the normal and mutant alleles are compared. Decrease in hybridization level: Differences in the sequence between a control sample and a test sample can be identified by a decrease in the hybridization level of the totally complementary oligonucleotides with a reference sequence. A loss approximating 100% is produced in mutant homozygous individuals while there is only an approximately 50% loss in heterozygotes.

In Microarrays for examining all the bases of a sequence of "n" nucleotides ("oligonucleotide") of length in both strands, a minimum of "2n" oligonucleotides that overlap with the previous oligonucleotide in all the sequence except in the nucleotide are necessary. Typically the size of the oligonucleotides is about 25 nucleotides. However it should be appreciated that the oligonucleotide can be any length that is appropriate as would be understood by one of ordinary skill in the art.

The increased number of oligonucleotides used to reconstruct the sequence reduces errors derived from fluctuation of the hybridization level. However, the exact change in sequence cannot be identified with this method; in some embodiments this method is combined with sequencing to identify the mutation. Where amplification or extension is carried out on the microarray or bead itself, three methods are presented by way of example: In the Minisequencing strategy, a mutation specific primer is fixed on the slide and after an extension reaction with fluorescent dideoxynucleotides, the image of the Microarray is captured with a scanner. In the Primer extension strategy, two oligonucleotides are designed for detection of the wild type and mutant sequences respectively. The extension reaction is subsequently carried out with one fluorescently labelled nucleotide and the remaining nucleotides unlabelled. In either case the starting material can be either an RNA sample or a DNA product amplified by PCR. In the Tag arrays strategy, an extension reaction is carried out in solution with specific primers, which carry a determined $5^1$ sequence or "tag". The use of Microarrays with oligonucleotides complementary to these sequences or "tags" allows the capture of the resultant products of the extension. Examples of this include the high density Microarray "Flexflex" (Affymetrix). In the Illumine 1M Dou BeadChip array (www.illumina.com/products/human1m_duo_dna_analysis_beadchip_kits.ilmn), SNP genotypes are generated from fluorescent intensities using the manufacturer's default cluster settings.

In some aspects of the invention, predictive models including SNPs from tables 1-3 or table 16, are used to predict the response to GA.

In some aspects of the invention, predictive models include 1, 2, 3, 4, 5, 6, 7, 8, 9, 10, 11, 12, 13, 14 or more SNPs.

In some aspects of the invention, predictive models include 4, 6, 10, 11, 12, 13 or 14 SNPs.

In some aspects of the invention, a prediction model includes a specific set of SNPs constituting the model.

Some specific sets of SNPs constituting models of the invention are presented in tables 5, 8 and 17.

In some aspects of the invention, a predictive model (or "model") is used to calculate the response probability p(Response) of a patient based on the genotype of the patient at the SNPs included in the specific model.

In some aspects of the invention, patients with a p(Response) above a specific threshold ("a predictive threshold") are predicted to be responders to GA while patients with a p(Response) below the same predictive threshold are predicted to be non-responders to GA.

In other aspects of the invention, patients with a p(Response) above a first predictive threshold (for example. 0.8) are predicted to be responders to GA while patients with a p(Response) below a second predictive threshold which is lower than the first threshold (for example, 0.2) are predicted to be non-responders to GA.

In some aspects of the invention, patients with a p(Response) above 0.1, 0.2, 0.3, 0.4, 0.5, 0.6, 0.7, 0.8 or 0.9 are predicted to be responders.

In some aspects of the invention, patients with a p(Response) below 0.1, 0.2, 0.3, 0.4, 0.5, 0.6, 0.7, 0.8 or 0.9 are predicted to be non-responders.

In a certain aspect of the invention, the predictive threshold is 0.5, such that a patient with response probability p(Response) above 0.5 is predicted to be a responder to GA treatment and a patient with p(Response) below 0.5 is predicted to be a non-responder to GA treatment.

In another aspect of the invention, the predictive threshold is 0.8, such that a patient with response probability p(Response) above 0.8 is predicted to be a responder to GA treatment and a patient with p(Response) below 0.8 is predicted to be a non-responder to GA treatment.

In some aspects of the invention, the p(Response) is compared to a predetermined threshold or thresholds in order to decide whether to treat the patient with GA.

In certain aspects of the invention, such comparison is made by the patient and/or a caregiver including but not limited to a healthcare provider and a family member, or by a medical or a scientific entity including but not limited a hospital, a medical institute or a lab.

In other aspects of the invention, the p(Response) is used by the patient and/or a caregiver including but not limited to a healthcare provider and a family member or by a medical or a scientific entity including but not limited a hospital, a medical institute or a lab in order to decide whether to treat the patient with GA without referring to a specific/predetermined predictive threshold or thresholds.

In some aspects of the invention, the p(Response) calculation includes using a kit.

In some aspects of the invention, the use of the kit comprises genotyping of the patient.

In some aspects of the invention, the use of the kit comprises calculating the p(Response) of the patient.

In certain aspects of the invention, the use of the kit comprises an indication to the user if the patient is genetically predicted to be a responder or a non-responder to GA.

In some aspects of the invention measurement of clinical variables comprises part of the prediction model predicting response to GA along with the genetic variables. Some non-limiting examples of clinical variables are the age of the patient (in years), gender of patient, clinical manifestations and MRI parameter. "Clinical manifestations" include but are not limited to EDSS score and relapse rate. "MRI parameters" include but are not limited to the volume and/or number of T1 enhancing lesions and/or T2 enhancing lesions. In certain aspect of the invention, the clinical variables taken into account are as measured at the time of the decision about the treatment suitable for the patient, or measured at a time point which seams reasonable to the physician, researcher or other professional involved in the decision.

The identification of a patient as a responder or as a non-responder to GA based on the presence of at least one SNP from tables 1-3 or table 16 a set of SNPs from tables 1-3, 5, 8, 16 or 17, or the combination of a SNP or a set of SNPs from tables 1-3, 5, 8, 16 or 17 with one or more clinical variables described above, may be used for predicting response to GA.

Also within the scope of the invention are kits and instructions for their use.

In some embodiments of the invention the kits are diagnostic kits.

In some embodiments of the invention the kits are PCR amplification kits.

In some embodiments kits associated with the invention are kits for identifying one or more SNPs within a patient sample.

In some embodiments a kit may contain primers for amplifying a specific genetic locus.

In some embodiments, a kit may contain a probe for hybridizing to a specific SNP.

In some embodiments kits associated with the invention contain at least one pair of PCR primers designed to amplify a DNA segment which includes a SNP of the invention.

In some embodiments kits associated with the invention contain a set of pairs of PCR primers designed to amplify a specific set of SNPs constituting a model of the invention.

In some embodiments kits associated with the invention contain at least one probe specific for a SNP of the invention.

In some embodiments kits associated with the invention contain a set of probes specific for a specific set of SNPs constituting a model of the invention.

The kit of the invention can include reagents for conducting each of the following assays including but not limited to restriction fragment length polymorphism (RFLP) analysis, microarrays including but not limited to planar microarrays or bead arrays, sequencing, single strand conformation polymorphism analysis (SSCP), chemical cleavage of mismatch (CCM), and denaturing high performance liquid chromatography (DHPLC), PCR amplification and sequencing of the DNA region comprising the SNP. In some aspects of the invention, the kit comprises a TaqMan Open Array or reagents for conducting a TaqMan Open Array assay.

In some aspects of the invention, the TaqMan Open Array is designed for genotyping SNPs of the invention. In some aspects of the invention, the TaqMan Open Array is designed for genotyping a specific set of SNPs constituting a model of the invention.

A kit of the invention can include a description of use of the contents of the kit for participation in any biological or chemical mechanism disclosed herein.

A kit can include instructions for use of the kit components alone or in combination with other methods or compositions for assisting in screening or diagnosing a sample and/or determining whether a subject is predicted to be a responder or a non-responder to GA.

In some embodiments, a kit of the invention includes instructions for calculating a p(Response) of a patient based on his/her genotype in specific SNPs. In some embodiments, the instructions include a predictive threshold or predictive thresholds and instructions or recommendations of how to compare the calculated p(Response) to the threshold/s in order to predict whether the subject is a responder or non-responder to GA.

Forms of Multiple Sclerosis:

There are five distinct disease stages and/or types of MS:
1) benign multiple sclerosis;
2) relapsing-remitting multiple sclerosis (RRMS);
3) secondary progressive multiple sclerosis (SPMS);
4) progressive relapsing multiple sclerosis (PRMS); and
5) primary progressive multiple sclerosis (PPMS).

Benign multiple sclerosis is a retrospective diagnosis which is characterized by 1-2 exacerbations with complete recovery, no lasting disability and no disease progression for 10-15 years after the initial onset. Benign multiple sclerosis may, however, progress into other forms of multiple sclerosis.

Patients suffering from RRMS experience sporadic exacerbations or relapses, as well as periods of remission. Lesions and evidence of axonal loss may or may not be visible on MRI for patients with RRMS.

SPMS may evolve from RRMS. Patients afflicted with SPMS have relapses, a diminishing degree of recovery during remissions, less frequent remissions and more pronounced neurological deficits than RRMS patients. Enlarged ventricles, which are markers for atrophy of the corpus callosum, midline center and spinal cord, are visible on MRI of patients with SPMS.

PPMS is characterized by a steady progression of increasing neurological deficits without distinct attacks or remissions. Cerebral lesions, diffuse spinal cord damage and evidence of axonal loss are evident on the MRI of patients with PPMS. PPMS has periods of acute exacerbations while proceeding along a course of increasing neurological deficits without remissions. Lesions are evident on MRI of patients suffering from PRMS. (28)

A clinically isolated syndrome (CIS) is a single monosymptomatic attack compatible with MS, such as optic neuritis, brain stem symptoms, and partial myelitis. Patients with CIS that experience a second clinical attack are generally considered to have clinically definite multiple sclerosis (CDMS). Over 80 percent of patients with a CIS and MRI lesions go on to develop MS, while approximately 20 percent have a self-limited process. (29, 30) Patients who experience a single clinical attack consistent with MS may have at least one lesion consistent with multiple sclerosis prior to the development of clinically definite multiple sclerosis.

Multiple sclerosis may present with optic neuritis, blurring of vision, diplopia, involuntary rapid eye movement, blindness, loss of balance, tremors, ataxia, vertigo, clumsiness of a limb, lack of co-ordination, weakness of one or more extremity, altered muscle tone, muscle stiffness, spasms, tingling, paraesthesia, burning sensations, muscle pains, facial pain, trigeminal neuralgia, stabbing sharp pains, burning tingling pain, slowing of speech, slurring of words, changes in rhythm of speech, dysphagia, fatigue, bladder problems (including urgency, frequency, incomplete emptying and incontinence), bowel problems (including constipation and loss of bowel control) impotence, diminished sexual arousal, loss of sensation, sensitivity to heat, loss of short term memory, loss of concentration, or loss of judgment or reasoning.

Relapsing Form of Multiple Sclerosis:
The term relapsing MS includes:
1) patients with RRMS;
2) patients with SPMS and superimposed relapses; and
3) patients with CIS who show lesion dissemination on subsequent MRI scans according to McDonald's criteria.

As used herein, relapsing forms of multiple sclerosis include: Relapsing-remitting multiple sclerosis (RAMS), characterized by unpredictable acute episodes of neurological dysfunction (relapses), followed by variable recovery and periods of clinical stability;

Secondary Progressive MS (SPMS), wherein patients having RRMS develop sustained deterioration with or without relapses superimposed; and Primary progressive-relapsing multiple sclerosis (PPRMS) or progressive-relapsing multiple sclerosis (PRMS), an uncommon form wherein patients developing a progressive deterioration from the beginning can also develop relapses later on.

Kurtzke Expanded Disability Status Scale (EDSS):
The Kurtzke Expanded Disability Status Scale (EDSS) is a method of quantifying disability in multiple sclerosis. The EDSS replaced the previous Disability Status Scales which used to bunch people with MS in the lower brackets. The EDSS quantifies disability in eight Functional Systems (FS) and allows neurologists to assign a Functional System Score (FSS) in each of these. The Functional Systems are: pyramidal, cerebellar, brainstem, sensory, bowel and bladder, visual & cerebral (according to www.mult-sclerosis.org/expanded-disabilitystatusscale).

Clinical Relapse:
A clinical relapse, which may also be used herein as "relapse," "confirmed relapse," or "clinically defined relapse," is defined as the appearance of one or more new neurological abnormalities or the reappearance of one or more previously observed neurological abnormalities.

This change in clinical state must last at least 48 hours and be immediately preceded by a relatively stable or improving neurological state of at least 30 days. This criterion is different from the clinical definition of exacerbation "at least 24 hours duration of symptoms," (31) as detailed in the section "relapse evaluation."

An event is counted as a relapse only when the subject's symptoms are accompanied by observed objective neurological changes, consistent with:
a) an increase of at least 0.5 in the EDSS score or one grade in the score of two or more of the seven FS (32); or,
b) two grades in the score of one of FS as compared to the previous evaluation.

The subject must not be undergoing any acute metabolic changes such as fever or other medical abnormality. A change in bowel/bladder function or in cognitive function must not be entirely responsible for the changes in EDSS or FS scores.

As used herein "a predicted responder/a genetically predicted responder to glatiramer acetate" is a human subject afflicted with multiple sclerosis or a single clinical attack consistent with multiple sclerosis that is predicted to be a responder to glatiramer acetate based on his/her genotype at SNPs, sets of SNPs or models of the invention. Similarly, a subject or patient which is predicted to be a non-responder to glatiramer acetate treatment based on his/her genotype is called "a predicted non-responder/genetically predicted non-responder to glatiramer acetate".

As used herein, a "multiple sclerosis drug" is a drug or an agent intended to treat clinically defined MS, CIS, any form of neurodegenerative or demyelinating diseases, or symptoms of any of the above mentioned diseases. "Multiple sclerosis drugs" may include but are not limited to antibodies, immunosuppressants, anti-inflammatory agents, immunomodulators, cytokines, cytotoxic agents and steroids and may include approved drugs, drugs in clinical trial, or alternative treatments, intended to treat clinically defined MS, CIS or any form of neurodegenerative or demyelinating diseases. "multiple sclerosis drugs" include but are not limited to Interferon and its derivatives (including BETASERON®, AVONEX® and REBIF®), Mitoxantrone and Natalizumab. Agents approved or in-trial for the treatment of other autoimmune diseases, but used in a MS or CIS patient to treat MS or CIS are also defined as multiple sclerosis drugs.

As used herein, a "naïve patient" is a subject that has not been treated with any multiple sclerosis drugs as defined in the former paragraph.

The administration of glatiramer acetate may be oral, nasal, pulmonary, parenteral, intravenous, intra-articular, transdermal, intradermal, subcutaneous, topical, intramuscular, rectal, intrathecal, intraocular, buccal or by gavage.

EXPERIMENTAL DETAILS

Examples

Analysis of DNA Sequence Polymorphism in Patients Classified as Responders or Non-Responders to GA Methods
Subjects:
Relapsing-remitting multiple sclerosis patients were treated with either 20 mg GA or 40 mg GA daily in the Teva FORTE clinical trial www.medicalnewstoday.com/articles/48863.php). Blood samples were drawn from each subject that signed an informed consent for the pharmacogenetic study and analyzed as described below.

The incidence of clinical relapses, and MRI data after 12 months treatment (T1 and T2 enhancing lesions) were used to define patients as responders or non-responders, according to two definitions: A "broad definition" or A "narrow definition" described herein below. In a first analysis, the subjects were binomially classified as "responders" (R) or "non-responders" (NR) according to a definition herein below defined as "broad". A further analysis was then conducted using a narrower definition, excluding some of the patients formerly classified as responders and leading to a much smaller sample. In addition, a third analysis used a continuous measure of response to GA, which was calculated based on the patients' clinical data and MRI parameters as described herein below ("A continuous measure").

Response Definitions

A "broad definition" or "broad phenotype": Responders according to the broad definition were defined as patients in the treatment group which had no relapse during the 12 months treatment period, and no T1 enhancing lesions and no new T2 enhancing lesions were observed at 12 months (end of 12 month treatment). Non responders were defined as patients having at least one relapse during the 12 months treatment period, and more than one new T2 enhancing lesion at 12 months.

A "narrow definition" or "narrow phenotype": Responders according to the narrow definition, were defined as patients in the treatment group which had no relapse during the 12 months treatment period, and no T1 enhancing lesions and no new T2 enhancing lesions at 12 months, as in the "broad" definition. In addition, patients in which no T1 enhancing lesion were observed at the time of recruitment and subjects in which the volume of T2 lesions significantly increased by 1000 $mm^3$) during the experiment were not defined as responders. The definition of Non-responders was the same as in the "broad" definition.

A "Composite measure", "composite phenotype" or "continuous measure" is calculated based on the clinical and MRI parameters (relapse rate during the 12 months treatment and T1 and T2 enhancing lesions at 12 months). This measure which is a continuous measure (in contrast to the "responder/non-responder" Binomial measure) was used in quantitative GWAS looking for SNPs associated with GA R/NR.

Relapse Evaluation

A clinical relapse was defined as the appearance of one or more new neurological abnormalities or the reappearance of one or more previously observed neurological abnormalities. This change in clinical state lasted at least 48 hours and was immediately preceded by a relatively stable or improving neurological state of at least 30 days. The criterion used in the study was different from the clinical definition of exacerbation "at least 24 hours duration of symptoms". (31) Since "in study" exacerbation definition must be supported by an objective neurological evaluation (see next paragraph), a neurological deficit must sustain long enough to eliminate pseudo exacerbations.

An event was counted as a relapse only when the subject's symptoms were accompanied by observed objective neurological changes, consistent with:

a) an increase of at least 0.5 in the EDSS score or one grade in the score of two or more of the seven FS (32); or,
b) two grades in the score of one of FS as compared to the previous evaluation.

The subject was not undergoing any acute metabolic changes such as fever or other medical abnormality. A change in bowel/bladder function or in cognitive function was not entirely responsible for the changes in EDSS or FS scores.

Subject Evaluation by the Examining Neurologist

A complete neurological assessment was performed at months −1 (screening), 0 (baseline), 3, 6, 9, 12 (end of double-blind phase), 18 and 24 (termination/early discontinuation).

Relapse Determination by the Treating Neurologist

The decision as to whether the neurological change was considered a confirmed relapse was made by the Treating Physician, based on EDSS/FS actual (not converted) scores assessed by the Examining Neurologist.

Follow-up visits to monitor the course of the relapse were made at the Treating Physician's discretion, in addition to the assessment at the next scheduled visit, but the neurological assessments were performed by the Examining Neurologist.

Relapse Evaluation Procedures

Subjects were instructed to telephone their study site within 48 hours should any symptoms suggestive of a relapse appear.

The Examining Neurologist evaluated the subject within 7 days of symptoms onset, conditional upon a symptomatic period of ≥48 hours. The Treating Neurologist/Physician evaluated the subject once any symptom suggestive of a relapse occurred.

In case of a suggestive relapse during a scheduled or unscheduled visit, the Treating Neurologist/Physician referred the subject to the Examining eurologist/Physician.

Analysis

The DNA chip selected for the GWAS was Illumine 1M Dou BeadChip(www.illumina.com/products/human1m_duo_dna_analysis_beadchip_kits.ilmn). Normalized bead intensity data obtained for each sample were analyzed with the Illumina Genome Studio v1.0.2 software, which generated SNP genotypes (including the different homozygotes and heterozygotes), from fluorescent intensities using the manufacturer's default cluster settings. Quality Controls (QC) included evaluation of call rate, check of SNPs with (1) no calls, (2) with MAF less than 0.05 and (3) with genotyping rate less than 0.9. SNPs that did not match these criteria were removed from further analyses. Data from individuals with missing genotyping>10% were also excluded from analyses. An additional quality control step was performed to exclude individuals and/or markers based on Mendelian error rate (PLINK; 56) version 1.04). SNPs with more than 10% and families with more than 5% Mendelian errors were discarded. Additionally, SNPs that showed a significant deviation from Hardy-Weinberg Equilibrium (HWE—p<0.00001) were flagged for evaluation before excluding them from further analyses.

GWAS analyses have been performed with the PLINK software (pngu.mgh.harvard.edu/~purcell/plink/), using the appropriate subroutines to analyze binomial or continuous measures. Results have not been corrected for multiple testing. SNPs with a p value of $10^{-4}$ or lower from the three analyses are considered as having a predictive ability of GA response. For the binomial measures (broad and narrow definitions), a marker was selected if the distribution of genotypes were significantly different in responders than in non responders.

Predictive Modeling

To find genotypic profiles that discriminate responders (R) from the non-responders (NR) to the treatment, we used a backward stepwise logistic regression procedure on the SNPs that emerged significant using the narrow definition (e.g., at p-value=$10^{-4}$ or lower). Other models were generated based on combinatorial optimization heuristics. Once a pool of models was created, selected models were chosen based on the low value of Akaike's Information Criterion (AIC) and low number SNPs in the model. The model chosen in the previous step went through "Leave one out" cross validation, searching for high values of the Area Under the ROC curve.

The response probability p(Response) of a specific patient was calculated according to the tables and formulas indicated for each specific model.

The SNPs were further genotypes by the TaqMan open array assay and the predictive value in the FORTE cohort and other cohorts was evaluated. Some of the predictive models were also evaluated in the same cohorts.

Results
GWAS Using the Three R/NR Phenotypes Found 86 SNPs having a Predictive Value for the Response to Treatment with GA As described in the "methods" section, SNPs with a p value of $10^{-4}$ or lower from the three analyses were considered as having a predictive ability of GA response.

When we conducted the GWAS analysis based on the broad definition, 17 SNPs having p value of $10^{-4}$ or lower were found. These SNPs are presented in table 1.

A second analysis was performed which included responders and non-responders according to the narrow definition. Using this definition, 31 SNPs having p value of $10^{-4}$ or lower were found. These SNPs are presented in table 2.

Performing the analysis using the composite phenotype, Genome-Wide (GW) significance was found for 38 SNPs having p value of $10^{-4}$ or lower, which are presented in table 3.

TABLE 1

Annotated SNPs with p-val < or = 1*10E−05 from the GWAS of the broad phenotype. Seventeen (17) SNPs have been genotyped with the Human1M Illumina chip and 110 additional SNPs are uniquely tagged by the genotyped SNPs. Among these 110 tagged SNPs, 11 are cross-represented within the list of the 17 "taggers", ultimately leading to 99 tagged SNPs that are not present, on the Human 1M chip.

| SNP | rank | P | chrom | coordinates | closest gene | type | distance to gene | Tagged_SNP | Tagged_SNP_r2 | Tagged_SNP_P |
|---|---|---|---|---|---|---|---|---|---|---|
| rs17771939 | 1 | 3.05E−07 | 8 | 94259105 | AC011118.2 | INTERGENIC | 99590 | | | |
| rs6097801 | 2 | 9.87E−07 | 20 | 52767434 | CYP24A1 | DOWNSTREAM | 2554 | | | |
| rs6097797 | 3 | 1.60E−06 | 20 | 52763331 | CYP24A1 | INTERGENIC | 6657 | | | |
| | | | | | | | | rs4811492 | 1 | — |
| | | | | | | | | rs1886308 | 1 | — |
| | | | | | | | | rs6097782 | 1 | — |
| | | | | | | | | rs6091820 | 1 | — |
| | | | | | | | | rs11907046 | 1 | — |
| | | | | | | | | rs16999008 | 1 | — |
| | | | | | | | | rs873216 | 1 | — |
| | | | | | | | | rs6097790 | 1 | — |
| | | | | | | | | rs6097793 | 1 | — |
| | | | | | | | | rs4809955 | 1 | 1.83E−06 |
| | | | | | | | | rs8118441 | 1 | — |
| | | | | | | | | rs6097801 | 1 | 9.87E−07 |
| rs4809955 | 4 | 1.83E−06 | 20 | 52765349 | CYP24A1 | DOWNSTREAM | 4639 | | | |
| rs1229553 | 5 | 2.53E−06 | 7 | 97432533 | ; ASNS | INTERGENIC | 48907 | | | |
| | | | | | | | | rs1234567 | 1 | — |
| | | | | | | | | rs1229568 | 1 | 3.76E−06 |
| | | | | | | | | rs1234947 | 1 | — |
| | | | | | | | | rs1237625 | 1 | — |
| | | | | | | | | rs1229564 | 1 | 3.76E−06 |
| | | | | | | | | rs1229563 | 1 | — |
| | | | | | | | | rs1229562 | 1 | — |
| | | | | | | | | rs1229559 | 1 | — |
| | | | | | | | | rs1229558 | 1 | — |
| | | | | | | | | rs1229557 | 1 | — |
| | | | | | | | | rs1229555 | 1 | — |
| | | | | | | | | rs2530123 | 0.93 | — |
| | | | | | | | | rs2530121 | 0.93 | — |
| rs1229542 | 6 | 3.76E−06 | 7 | 97422926 | TAC1 | INTERGENIC | 53048 | | | |
| rs1229568 | 7 | 3.76E−06 | 7 | 97425721 | ASNS | INTERGENIC | 55719 | | | |
| | | | | | | | | rs1234567 | 1 | — |
| | | | | | | | | rs1234947 | 1 | — |
| | | | | | | | | rs1237625 | 1 | — |
| | | | | | | | | rs1229564 | 1 | 3.76E−06 |
| | | | | | | | | rs1229563 | 1 | — |
| | | | | | | | | rs1229562 | 1 | — |
| | | | | | | | | rs1229559 | 1 | — |
| | | | | | | | | rs1229558 | 1 | — |
| | | | | | | | | rs1229557 | 1 | — |
| | | | | | | | | rs1229555 | 1 | — |
| | | | | | | | | rs1229553 | 1 | 2.53E−06 |
| | | | | | | | | rs2530123 | 0.93 | — |
| | | | | | | | | rs2530121 | 0.93 | — |

TABLE 1-continued

Annotated SNPs with p-val < or = 1*10E−05 from the GWAS of the broad phenotype. Seventeen (17) SNPs have been genotyped with the Human1M Illumina chip and 110 additional SNPs are uniquely tagged by the genotyped SNPs. Among these 110 tagged SNPs, 11 are cross-represented within the list of the 17 "taggers", ultimately leading to 99 tagged SNPs that are not present, on the Human 1M chip.

| SNP | rank | P | chrom | coordinates | closest gene | type | distance to gene | Tagged_SNP | Tagged_SNP_r2 | Tagged_SNP_P |
|---|---|---|---|---|---|---|---|---|---|---|
| rs1229564 | 8 | 3.76E−06 | 7 | 97428673 | ASNS | INTER-GENIC | 52767 | | | |
| | | | | | | | | rs1234567 | 1 | — |
| | | | | | | | | rs1229568 | 1 | 3.76E−06 |
| | | | | | | | | rs1234947 | 1 | — |
| | | | | | | | | rs1237625 | 1 | — |
| | | | | | | | | rs1229563 | 1 | — |
| | | | | | | | | rs1229562 | 1 | — |
| | | | | | | | | rs1229559 | 1 | — |
| | | | | | | | | rs1229558 | 1 | — |
| | | | | | | | | rs1229557 | 1 | — |
| | | | | | | | | rs1229555 | 1 | — |
| | | | | | | | | rs1229553 | 1 | 2.53E−06 |
| | | | | | | | | rs2530123 | 0.93 | — |
| | | | | | | | | rs2530121 | 0.93 | — |
| rs4344916 | 9 | 3.84E−06 | 2 | 35597319 | AC083939.1 | INTER-GENIC | −99352 | | | |
| | | | | | | | | rs4670454 | 0.84 | — |
| | | | | | | | | rs1439859 | 0.88 | 0.0008 |
| | | | | | | | | rs7570329 | 0.88 | — |
| | | | | | | | | rs1439850 | 0.38 | — |
| | | | | | | | | rs10208122 | 0.88 | — |
| | | | | | | | | rs7587522 | 0.88 | — |
| | | | | | | | | rs4670460 | 0.88 | — |
| | | | | | | | | rs12477791 | 0.88 | — |
| | | | | | | | | rs17327405 | 0.88 | 0.004 |
| | | | | | | | | rs7419474 | 0.88 | — |
| | | | | | | | | rs2371748 | 0.88 | — |
| | | | | | | | | rs11124426 | 0.88 | — |
| | | | | | | | | rs7608244 | 0.88 | — |
| | | | | | | | | rs13424077 | 0.92 | 2.33E−05 |
| | | | | | | | | rs13398774 | 0.96 | — |
| | | | | | | | | rs13429141 | 0.88 | — |
| | | | | | | | | rs4233912 | 0.92 | — |
| | | | | | | | | rs10168563 | 0.92 | — |
| | | | | | | | | rs4643516 | 0.88 | — |
| | | | | | | | | rs7579183 | 0.88 | 0.0002 |
| | | | | | | | | rs10174888 | 0.92 | — |
| | | | | | | | | rs10184819 | 0.88 | — |
| | | | | | | | | rs4371344 | 0.88 | 0.0004 |
| | | | | | | | | rs10195590 | 0.88 | — |
| | | | | | | | | rs7584849 | 0.88 | — |
| | | | | | | | | rs6543931 | 0.87 | 0.0015 |
| | | | | | | | | rs4533454 | 0.92 | — |
| | | | | | | | | rs7603696 | 0.92 | 0.0003 |
| | | | | | | | | rs7584898 | 0.96 | — |
| | | | | | | | | rs11680546 | 0.96 | — |
| | | | | | | | | rs6739671 | 0.96 | — |
| | | | | | | | | rs9332420 | 0.96 | 1.13E−05 |
| | | | | | | | | rs7556865 | 0.96 | — |
| | | | | | | | | rs7599336 | 0.96 | — |
| | | | | | | | | rs13021482 | 0.96 | 1.48E−05 |
| | | | | | | | | rs6726189 | 0.96 | — |
| | | | | | | | | rs6741426 | 0.96 | — |
| | | | | | | | | rs11674793 | 0.96 | — |
| | | | | | | | | rs7560990 | 0.96 | — |
| | | | | | | | | rs6543934 | 0.96 | 1.48E−05 |
| | | | | | | | | rs11694344 | 0.96 | 1.82E−05 |
| | | | | | | | | rs6543935 | 0.96 | — |
| | | | | | | | | rs4578835 | 1 | — |
| | | | | | | | | rs4281882 | 1 | — |
| | | | | | | | | rs4289164 | 1 | 6.43E−06 |
| | | | | | | | | rs4435429 | 1 | — |
| | | | | | | | | rs11124430 | 0.88 | 0.0005 |
| rs2487896 | 10 | 5.51E−06 | 10 | 100802380 | HPSE2 | IN-TRONIC | 0 | | | |
| | | | | | | | | rs2487889 | 0.93 | 2.86E−05 |
| rs5908518 | 11 | 6.09E−06 | X | 142128422 | SPANXN4 | INTER-GENIC | 5934 | | | |

TABLE 1-continued

Annotated SNPs with p-val < or = 1*10E−05 from the GWAS of the broad phenotype. Seventeen (17) SNPs have been genotyped with the Human1M Illumina chip and 110 additional SNPs are uniquely tagged by the genotyped SNPs. Among these 110 tagged SNPs, 11 are cross-represented within the list of the 17 "taggers", ultimately leading to 99 tagged SNPs that are not present, on the Human 1M chip.

| SNP | rank | P | chrom | coordinates | closest gene | type | distance to gene | Tagged_SNP | Tagged_SNP_r2 | Tagged_SNP_P |
|---|---|---|---|---|---|---|---|---|---|---|
| rs4289164 | 12 | 6.43E−06 | 2 | 35594631 | AC083939.1 | INTERGENIC | −102040 | | | |
| | | | | | | | | rs4670454 | 0.84 | — |
| | | | | | | | | rs1439859 | 0.88 | 0.0008 |
| | | | | | | | | rs7570329 | 0.88 | — |
| | | | | | | | | rs1439850 | 0.88 | — |
| | | | | | | | | rs10208122 | 0.88 | — |
| | | | | | | | | rs7587522 | 0.88 | — |
| | | | | | | | | rs4670460 | 0.88 | — |
| | | | | | | | | rs12477791 | 0.88 | — |
| | | | | | | | | rs17327405 | 0.88 | 0.004 |
| | | | | | | | | rs7419474 | 0.88 | — |
| | | | | | | | | rs2371748 | 0.88 | — |
| | | | | | | | | rs11124426 | 0.88 | — |
| | | | | | | | | rs7608244 | 0.88 | — |
| | | | | | | | | rs13424077 | 0.92 | 2.33E−05 |
| | | | | | | | | rs13398774 | 0.96 | — |
| | | | | | | | | rs13429141 | 0.88 | — |
| | | | | | | | | rs4233912 | 0.92 | — |
| | | | | | | | | rs10168563 | 0.92 | — |
| | | | | | | | | rs4643516 | 0.88 | — |
| | | | | | | | | rs7579183 | 0.88 | 0.0002 |
| | | | | | | | | rs10174888 | 0.92 | — |
| | | | | | | | | rs10184819 | 0.88 | — |
| | | | | | | | | rs4371344 | 0.88 | 0.0004 |
| | | | | | | | | rs10195590 | 0.88 | — |
| | | | | | | | | rs7584849 | 0.88 | — |
| | | | | | | | | rs6543931 | 0.87 | 0.0015 |
| | | | | | | | | rs4533454 | 0.92 | — |
| | | | | | | | | rs7603696 | 0.92 | 0.0003 |
| | | | | | | | | rs7584898 | 0.96 | — |
| | | | | | | | | rs11680546 | 0.96 | — |
| | | | | | | | | rs6739671 | 0.96 | — |
| | | | | | | | | rs9332420 | 0.96 | 1.13E−05 |
| | | | | | | | | rs7556865 | 0.96 | — |
| | | | | | | | | rs7599336 | 0.96 | — |
| | | | | | | | | rs13021482 | 0.96 | 1.48E−05 |
| | | | | | | | | rs6726189 | 0.96 | — |
| | | | | | | | | rs6741426 | 0.96 | — |
| | | | | | | | | rs11674793 | 0.96 | — |
| | | | | | | | | rs7560990 | 0.96 | — |
| | | | | | | | | rs6543934 | 0.96 | 1.48E−05 |
| | | | | | | | | rs11694344 | 0.96 | 1.82E−05 |
| | | | | | | | | rs6543935 | 0.96 | — |
| | | | | | | | | rs4578835 | 1 | — |
| | | | | | | | | rs4281882 | 1 | — |
| | | | | | | | | rs4344916 | 1 | 3.84E−06 |
| | | | | | | | | rs4435429 | 1 | — |
| | | | | | | | | rs11124430 | 0.88 | 0.0005 |
| rs9405541 | 13 | 6.55E−06 | 6 | 2052811 | GMDS | INTRONIC | 0 | | | |
| | | | | | | | | rs9392358 | 1 | — |
| | | | | | | | | rs9378319 | 1 | — |
| | | | | | | | | rs12055694 | 1 | 6.55E−06 |
| | | | | | | | | rs17134651 | 1 | — |
| | | | | | | | | rs9405546 | 1 | — |
| | | | | | | | | rs9378684 | 1 | — |
| rs12055694 | 14 | 6.55E−06 | 6 | 2072157 | GMDS | INTRONIC | 0 | | | |
| | | | | | | | | rs9405541 | 1 | 6.55E−06 |
| | | | | | | | | rs9392358 | 1 | — |
| | | | | | | | | rs9378319 | 1 | — |
| | | | | | | | | rs17134651 | 1 | — |
| | | | | | | | | rs9405546 | 1 | — |
| | | | | | | | | rs9378684 | 1 | — |
| rs11009827 | 15 | 7.76E−06 | 10 | 19710332 | C10orf112 | INTRONIC | 0 | | | |
| | | | | | | | | rs11009812 | 1 | — |
| | | | | | | | | rs11009826 | 1 | — |
| | | | | | | | | rs7912880 | 0.82 | — |
| | | | | | | | | rs11009835 | 1 | 7.76E−06 |
| | | | | | | | | rs11009843 | 1 | — |

TABLE 1-continued

Annotated SNPs with p-val < or = 1*10E−05 from the GWAS of the broad phenotype. Seventeen (17) SNPs have been genotyped with the Human1M Illumina chip and 110 additional SNPs are uniquely tagged by the genotyped SNPs. Among these 110 tagged SNPs, 11 are cross-represented within the list of the 17 "taggers", ultimately leading to 99 tagged SNPs that are not present, on the Human 1M chip.

| SNP | rank | P | chrom | coordinates | closest gene | type | distance to gene | Tagged_SNP | Tagged_SNP_r2 | Tagged_SNP_P |
|---|---|---|---|---|---|---|---|---|---|---|
| rs11009835 | 16 | 7.76E−06 | 10 | 19712714 | C10orf112 | INTRONIC | 0 | | | |
| | | | | | | | | rs11009812 | 1 | — |
| | | | | | | | | rs11009826 | 1 | — |
| | | | | | | | | rs11009827 | 1 | 7.76E−06 |
| | | | | | | | | rs7912880 | 0.86 | — |
| | | | | | | | | rs11009843 | 1 | — |
| | | | | | | | | rs10508584 | 0.8 | — |
| rs12637073 | 17 | 9.79E−06 | 3 | 132183561 | DNAJC13 | INTRONIC | 0 | | | |
| | | | | | | | | rs12639443 | 1 | — |
| | | | | | | | | rs11709339 | 1 | — |
| | | | | | | | | rs12633010 | 1 | — |
| | | | | | | | | rs10935015 | 1 | — |
| | | | | | | | | rs12496278 | 1 | — |
| | | | | | | | | rs10935016 | 1 | — |
| | | | | | | | | rs7619350 | 1 | 1.53E−05 |
| | | | | | | | | rs7633210 | 0.93 | — |
| | | | | | | | | rs12494606 | 0.93 | 4.90E−05 |
| | | | | | | | | rs12488259 | 0.86 | 4.90E−05 |
| | | | | | | | | rs10935019 | 0.93 | 4.90E−05 |
| | | | | | | | | rs2088713 | 0.93 | 4.90E−05 |
| | | | | | | | | rs11719825 | 0.93 | 4.90E−05 |
| | | | | | | | | rs10804610 | 0.93 | 0.0008 |
| | | | | | | | | rs6779298 | 0.86 | 0.0008 |
| | | | | | | | | rs2305623 | 0.93 | 0.0002 |
| | | | | | | | | rs11719902 | 0.93 | 0.0002 |
| | | | | | | | | rs10935023 | 0.93 | 0.0001 |
| | | | | | | | | rs12491543 | 0.93 | — |
| | | | | | | | | rs10512873 | 0.93 | — |
| | | | | | | | | rs2168435 | 0.93 | 0.0006 |

TABLE 2

Annotated SNPs with p-val < or = 5*10E−05 from the GWAS of the narrow phenotype. Thirtyone (31) SNPs have been genotyped with the Human1M Illumina chip and 82 additional SNPs are uniquely tagged by the genotyped SNPs. Among these 82 tagged SNPs, 6 are cross-represented within the list of the 31 "taggers", ultimately leading to 76 tagged SNPs that are not present on the Human 1M chip.

| SNP | rank | P | chrom | coordinates | type | closest gene |
|---|---|---|---|---|---|---|
| rs10277267 | 1 | 4.03E−06 | 7 | 1809120 | INTERGENIC | AC074389.1 |
| rs10950359 | 2 | 4.89E−06 | 7 | 1800967 | INTRONIC | AC074389.1 |
| rs2521644 | 3 | 6.48E−06 | 7 | 24427969 | INTERGENIC | NPY |
| rs35603463 | 4 | 9.28E−06 | 6 | 32531745 | UPSTREAM | AL713966.2 |
| rs13245980 | 5 | 9.64E−06 | 7 | 1813198 | INTERGENIC | AC074389.1 |
| rs10270654 | 6 | 9.64E−06 | 7 | 1815851 | INTERGENIC | AC074389.1 |
| rs1538123 | 7 | 1.48E−05 | 10 | 110513959 | WITHIN_NON_CODING_GENE | RP11-655H13.2 |
| rs4369324 | 8 | 1.48E−05 | 10 | 110530574 | WITHIN_NON_CODING_GENE | ;RP11-655H13.2 |
| rs2895215 | 9 | 1.81E−05 | 7 | 1837636 | INTERGENIC | MAD1L1 |
| rs10950371 | 10 | 1.95E−05 | 7 | 1825304 | INTERGENIC | AC074389.1 |
| rs7916897 | 11 | 2.39E−05 | 10 | 9061104 | INTERGENIC | RP11-428L9.2 |
| rs17807445 | 12 | 2.54E−05 | 6 | 80804273 | INTERGENIC | BCKDHB |
| rs17771939 | 13 | 2.62E−05 | 8 | 94259105 | INTERGENIC | AC011118.2 |
| rs6584894 | 14 | 2.90E−05 | 10 | 110518607 | WITHIN_NON_CODING_GENE | RP11-655H13.2 |
| rs496486 | 15 | 3.18E−05 | 3 | 107225936 | INTERGENIC | BBX |
| rs949298 | 16 | 3.29E−05 | 11 | 120608085 | INTRONIC | GRIK4 |
| rs948032 | 17 | 3.29E−05 | 11 | 120608661 | INTRONIC | GRIK4 |
| rs7803164 | 18 | 3.41E−05 | 7 | 1829835 | INTERGENIC | MAD1L1 |
| rs7093143 | 19 | 3.65E−05 | 10 | 110478002 | WITHIN_NON_CODING_GENE | RP11-655H13.2 |
| rs1415557 | 20 | 3.65E−05 | 10 | 110504802 | WITHIN_NON_CODING_GENE | RP11-655H13.2 |
| rs7086707 | 21 | 3.65E−05 | 10 | 110573667 | WITHIN_NON_CODING_GENE | RP11-655H13.2 |
| rs1007328 | 22 | 3.71E−05 | 15 | 96703373 | INTERGENIC | AC012409.1 |
| rs12256889 | 23 | 4.34E−05 | 10 | 94827183 | INTRONIC | CYP26C1 |
| rs214526 | 24 | 4.35E−05 | 6 | 18248916 | INTRONIC | DEK |

TABLE 2-continued

Annotated SNPs with p-val < or = 5*10E−05 from the GWAS of the narrow phenotype.
Thirtyone (31) SNPs have been genotyped with the Human1M Illumina chip and 82 additional SNPs are uniquely tagged by the genotyped SNPs. Among these 82 tagged SNPs, 6 are cross-represented within the list of the 31 "taggers", ultimately leading to 76 tagged SNPs that are not present on the Human 1M chip.

| | | | | | | |
|---|---|---|---|---|---|---|
| rs9315048 | 25 | 4.38E−05 | 13 | 31327840 | INTRONIC | ALOX5AP |
| rs4445746 | 26 | 4.38E−05 | 13 | 31341435 | DOWNSTREAM | RP11-469L23.2 |
| rs11599624 | 27 | 4.64E−05 | 10 | 110606763 | UPSTREAM | RP11-655H13.1 |
| rs2155262 | 28 | 4.65E−05 | 11 | 120610692 | INTRONIC | GRIK4 |
| rs10056549 | 29 | 4.73E−05 | 5 | 114329175 | INTERGENIC | RP11-438C19.2 |
| rs844626 | 30 | 4.85E−05 | 6 | 147898558 | WITHIN_NON_CODING_GENE | AL034350.1 |
| rs947603 | 31 | 4.87E−05 | 10 | 95249605 | INTERGENIC | CEP55 |

| SNP | rank | distance to gene | Tagged_SNP | Tagged_SNP_r2 | Tagged_SNP_P |
|---|---|---|---|---|---|
| rs10277267 | 1 | −7016 | | | |
| | | | rs2222813 | 0.91 | — |
| rs10950359 | 2 | 0 | | | |
| rs2521644 | 3 | 96485 | | | |
| | | | rs6971202 | 0.87 | — |
| | | | rs2722398 | 0.83 | — |
| | | | rs2521643 | 0.84 | — |
| | | | rs2722396 | 0.88 | 0.0016 |
| rs35603463 | 4 | −3946 | | | |
| rs13245980 | 5 | −11094 | | | |
| rs10270654 | 6 | −13747 | | | |
| | | | rs4634524 | 1 | — |
| | | | rs4255033 | 1 | — |
| | | | rs12532459 | 1 | — |
| | | | rs12540494 | 1 | — |
| | | | rs13231999 | 1 | — |
| | | | rs10280601 | 1 | — |
| | | | rs13245980 | 1 | 9.64E−06 |
| | | | rs10235174 | 1 | — |
| | | | rs10238227 | 1 | — |
| | | | rs10225815 | 1 | — |
| | | | rs10228960 | 1 | — |
| | | | rs6955820 | 1 | — |
| | | | rs10950368 | 1 | — |
| | | | rs10270415 | 1 | — |
| | | | rs10270538 | 1 | — |
| | | | rs12539381 | 1 | — |
| | | | rs10271168 | 1 | — |
| | | | rs4436012 | 1 | — |
| | | | rs10259574 | 1 | — |
| | | | rs10259592 | 1 | — |
| | | | rs10259699 | 1 | — |
| | | | rs10275253 | 1 | — |
| | | | rs10278438 | 1 | — |
| | | | rs1881858 | 0.87 | — |
| | | | rs11766215 | 0.85 | — |
| | | | rs10950371 | 0.86 | 1.95E−05 |
| rs1538123 | 7 | 0 | | | |
| | | | rs7080507 | 0.95 | 6.97E−05 |
| | | | rs1591661 | 0.95 | — |
| | | | rs2685484 | 0.95 | — |
| | | | rs2461319 | 0.86 | — |
| rs4369324 | 8 | 0 | | | |
| | | | rs7080507 | 0.95 | 6.97E−05 |
| | | | rs1591661 | 0.95 | — |
| | | | rs2685484 | 0.95 | — |
| | | | rs2461319 | 0.86 | — |
| rs2895215 | 9 | 17747 | | | |
| rs10950371 | 10 | −23200 | | | |
| rs7916897 | 11 | 45673 | | | |
| | | | rs1031161 | 0.96 | — |
| rs17807445 | 12 | −12091 | | | |
| | | | rs12524041 | 0.87 | — |
| | | | rs12529764 | 0.87 | 0.0002 |
| | | | rs17807327 | 1 | — |
| rs17771939 | 13 | 99590 | | | |
| rs6584894 | 14 | 0 | | | |
| rs496486 | 15 | −15847 | | | |
| | | | rs1282534 | 1 | — |
| | | | rs1282540 | 1 | 7.04E−05 |
| | | | rs1299325 | 1 | — |
| | | | rs1040194 | 1 | — |
| | | | rs1282546 | 0.91 | — |
| | | | rs552994 | 1 | — |
| | | | rs657302 | 1 | — |

TABLE 2-continued

Annotated SNPs with p-val < or = 5*10E−05 from the GWAS of the narrow phenotype.
Thirtyone (31) SNPs have been genotyped with the Human1M Illumina chip and 82 additional SNPs are uniquely tagged by the genotyped SNPs. Among these 82 tagged SNPs, 6 are cross-represented within the list of the 31 "taggers", ultimately leading to 76 tagged SNPs that are not present on the Human 1M chip.

|  |  |  |  |  |  |
|---|---|---|---|---|---|
|  |  |  | rs577189 | 1 | — |
|  |  |  | rs660075 | 1 | 7.04E−05 |
|  |  |  | rs656975 | 1 | — |
|  |  |  | rs860722 | 1 | — |
|  |  |  | rs618213 | 1 | — |
|  |  |  | rs565614 | 0.85 | — |
|  |  |  | rs2937395 | 1 | — |
| rs949298 | 16 | 0 |  |  |  |
| rs948032 | 17 | 0 |  |  |  |
|  |  |  | rs1320648 | 1 | — |
|  |  |  | rs752979 | 1 | — |
| rs7803164 | 18 | 25548 |  |  |  |
|  |  |  | rs1881858 | 0.82 | — |
|  |  |  | rs11766215 | 0.85 | — |
|  |  |  | rs10950371 | 0.9 | 1.95E−05 |
|  |  |  | rs13238613 | 0.95 | — |
|  |  |  | rs11761457 | 0.86 | — |
|  |  |  | rs7789703 | 0.86 | 9.91E−05 |
|  |  |  | rs7806265 | 0.95 | — |
|  |  |  | rs2895215 | 0.86 | 1.81E−05 |
| rs7093143 | 19 | 0 |  |  |  |
|  |  |  | rs7080507 | 0.95 | 6.97E−05 |
|  |  |  | rs1591661 | 0.95 | — |
|  |  |  | rs2685484 | 0.95 | — |
|  |  |  | rs2461319 | 0.9 | — |
| rs1415557 | 20 | 0 |  |  |  |
|  |  |  | rs7080507 | 0.95 | 6.97E−05 |
|  |  |  | rs1591661 | 0.95 | — |
|  |  |  | rs2685484 | 0.95 | — |
|  |  |  | rs2461319 | 0.86 | — |
| rs7086707 | 21 | 0 |  |  |  |
| rs1007328 | 22 | 108628 |  |  |  |
| rs12256889 | 23 | 0 |  |  |  |
| rs214526 | 24 | 0 |  |  |  |
| rs9315048 | 25 | 0 |  |  |  |
|  |  |  | rs4468448 | 0.95 | 0.0014 |
|  |  |  | rs12019512 | 0.9 | 0.0002 |
|  |  |  | rs4466940 | 0.9 | — |
|  |  |  | rs4445746 | 1 | 4.38E−05 |
| rs4445746 | 26 | −35908 |  |  |  |
|  |  |  | rs9315048 | 1 | 4.38E−05 |
|  |  |  | rs4468448 | 0.95 | 0.0014 |
|  |  |  | rs12019512 | 0.9 | 0.0002 |
|  |  |  | rs4466940 | 0.9 | — |
| rs11599624 | 27 | −1181 |  |  |  |
| rs2155262 | 28 | 0 |  |  |  |
|  |  |  | rs2852230 | 1 | — |
|  |  |  | rs949298 | 1 | 3.29E−05 |
|  |  |  | rs752979 | 0.81 | — |
|  |  |  | rs751370 | 0.83 | — |
|  |  |  | rs751369 | 0.87 | — |
|  |  |  | rs2187495 | 1 | — |
|  |  |  | rs2511064 | 1 | — |
|  |  |  | rs2508806 | 1 | — |
|  |  |  | rs1892974 | 1 | — |
|  |  |  | rs948029 | 1 | — |
| rs10056549 | 29 | −37795 |  |  |  |
| rs844626 | 30 | 0 |  |  |  |
|  |  |  | rs844612 | 1 | — |
|  |  |  | rs844610 | 1 | 0.0002 |
|  |  |  | rs844609 | 1 | — |
|  |  |  | rs844608 | 1 | — |
|  |  |  | rs702355 | 1 | — |
|  |  |  | rs844603 | 1 | — |
|  |  |  | rs844602 | 1 | — |
| rs947603 | 31 | −6764 |  |  |  |

TABLE 3

Annotated SNPs with p-val < or = 5*10E−05 from the GWAS of the composite phenotype
Thirty-eight (38) SNPs have been genotyped with the Human1M Illumina chip and 89 additional SNPs are uniquely tagged by the genotyped SNPs. Among these 89 tagged SNPs, 20 are cross-represented within the list of the 38 "taggers", ultimately leading to 69 tagged SNPs that are not present on the Human 1M chip.

| SNP | rank | P | chr | coordinate | type | closest gene |
|---|---|---|---|---|---|---|
| rs11617134 | 1 | 2.29E−08 | 13 | 30590793 | INTERGENIC | RP11-629E24.2 |
| rs17588454 | 2 | 3.92E−08 | 13 | 30580656 | INTERGENIC | RP11-629E24.2 |
| rs9944913 | 3 | 1.41E−07 | 18 | 31926438 | INTERGENIC | NOL4 |
| rs2177073 | 4 | 1.84E−07 | 18 | 32054724 | INTERGENIC | DTNA |
| rs913882 | 5 | 6.90E−07 | 20 | 56521654 | INTERGENIC | RP13-379L11.2 |
| rs10136012 | 6 | 1.29E−06 | 14 | 93505960 | INTRONIC | ITPK1 |
| rs6025927 | 7 | 1.35E−06 | 20 | 56523799 | INTERGENIC | RP13-379L11.2 |
| rs884266 | 8 | 1.60E−06 | 20 | 56520904 | INTERGENIC | RP13-379L11.2 |
| rs9405541 | 9 | 2.38E−06 | 6 | 2052811 | INTRONIC | GMDS |
| rs869106 | 10 | 2.38E−06 | 9 | 2421273 | DOWNSTREAM | RP11-125B21.2 |
| rs12055694 | 11 | 2.77E−06 | 6 | 2072157 | INTRONIC | GMDS |
| rs28861531 | 12 | 3.22E−06 | Y | 1324728 | INTERGENIC | N/A |
| rs10988087 | 13 | 3.35E−06 | 9 | 131443671 | UPSTREAM | SET |
| rs11618546 | 14 | 3.50E−06 | 13 | 58874752 | INTERGENIC | RP11-538C21.1 |
| rs894857 | 15 | 3.55E−06 | 1 | 211901341 | UPSTREAM | RP11-122M14.3 |
| rs12340584 | 16 | 4.00E−06 | 9 | 14210653 | INTRONIC | NFIB |
| rs6682365 | 17 | 4.01E−06 | 1 | 233718651 | INTERGENIC | KCNK1 |
| rs1573706 | 18 | 4.04E−06 | 20 | 40921149 | INTRONIC | PTPRT |
| rs12968586 | 19 | 4.59E−06 | 18 | 31909968 | INTERGENIC | NOL4 |
| rs11081859 | 20 | 4.73E−06 | 18 | 31926289 | INTERGENIC | NOL4 |
| rs17104742 | 21 | 4.86E−06 | 5 | 145895558 | NON_SYNONYMOUS_CODING | GPR151 |
| rs10214633 | 22 | 5.54E−06 | 6 | 147989996 | WITHIN_NON_CODING_GENE | RP11-307P5.1 |
| rs1041897 | 23 | 5.62E−06 | 20 | 46561222 | INTERGENIC | RP11-347D21.1 |
| rs7955917 | 24 | 5.82E−06 | 12 | 128860496 | INTERGENIC | AC023595.1 |
| rs6713772 | 25 | 5.95E−06 | 2 | 123216847 | INTERGENIC | N/A |
| rs17575455 | 26 | 6.00E−06 | 2 | 76624220 | INTERGENIC | AC078940.2 |
| rs1802027 | 27 | 6.79E−06 | 5 | 145890228 | 3PRIME_UTR | TCERG1 |
| rs998051 | 28 | 6.83E−06 | 5 | 145875259 | INTRONIC | TCERG1 |
| rs7714122 | 29 | 6.87E−06 | 5 | 96255017 | 3PRIME_UTR | ERAP2 |
| rs3742228 | 30 | 7.00E−06 | 13 | 113459221 | INTRONIC | ATP11A |
| rs4483642 | 31 | 7.19E−06 | 12 | 108308740 | INTERGENIC | ASCL4 |
| rs12439713 | 32 | 7.27E−06 | 15 | 91200733 | UPSTREAM | AC021422.1 |
| rs13042992 | 33 | 7.79E−06 | 20 | 14737843 | INTRONIC | MACROD2 |
| rs17007730 | 34 | 7.89E−06 | 2 | 123192216 | INTRONIC | N/A |
| rs2277431 | 35 | 9.19E−06 | 13 | 113473375 | INTRONIC | ATP11A |
| rs10931091 | 36 | 9.53E−06 | 2 | 184533968 | INTERGENIC | AC074182.1 |
| rs6558102 | 37 | 9.69E−06 | 8 | 29096853 | INTRONIC | KIF13B |
| rs4343256 | 38 | 1.01E−05 | 15 | 91198415 | INTERGENIC | AC021422.1 |

| SNP | rank | distance to gene | Tagged_SNP | Tagged_SNP_r2 | Tagged_SNP_P |
|---|---|---|---|---|---|
| rs11617134 | 1 | 5365 | | | |
| | | | rs35831078 | 0.82 | — |
| | | | rs35831078 | 0.82 | — |
| | | | rs17588454 | 0.82 | 3.92E−08 |
| | | | rs17588454 | 0.82 | 3.92E−08 |
| | | | rs7317000 | 1 | — |
| | | | rs7317000 | 1 | — |
| rs17588454 | 2 | 15502 | | | |
| | | | rs35831078 | 1 | — |
| | | | rs7317000 | 0.83 | — |
| | | | rs11617134 | 0.82 | 2.29E−08 |
| rs9944913 | 3 | −122923 | | | |
| | | | rs7238006 | 1 | — |
| | | | rs17666347 | 1 | 0.0004 |
| rs2177073 | 4 | −18530 | | | |
| rs913882 | 5 | 10528 | | | |
| | | | rs6025914 | 0.95 | — |
| | | | rs6025917 | 0.94 | — |
| | | | rs12480795 | 0.95 | — |
| | | | rs6015147 | 1 | — |
| | | | rs6025921 | 0.95 | — |
| | | | rs6025923 | 1 | — |
| | | | rs884266 | 0.95 | 1.60E−06 |
| | | | rs884265 | 1 | — |
| | | | rs6123749 | 1 | — |
| | | | rs6123750 | 1 | — |
| | | | rs6025924 | 1 | — |
| | | | rs6025926 | 1 | — |
| | | | rs6025927 | 1 | 1.35E−06 |

TABLE 3-continued

Annotated SNPs with p-val < or = 5*10E−05 from the GWAS of the composite phenotype
Thirty-eight (38) SNPs have been genotyped with the Human1M Illumina chip and 89 additional SNPs are uniquely tagged by the genotyped SNPs. Among these 89 tagged SNPs, 20 are cross-represented within the list of the 38 "taggers", ultimately leading to 69 tagged SNPs that are not present on the Human 1M chip.

| | | | | | |
|---|---|---|---|---|---|
| rs10136012 | 6 | 0 | | | |
| rs6025927 | 7 | 8383 | | | |
| | | | rs6025914 | 0.96 | — |
| | | | rs6025917 | 0.95 | — |
| | | | rs12480795 | 1 | — |
| | | | rs6015147 | 1 | — |
| | | | rs6025921 | 0.83 | — |
| | | | rs6025923 | 1 | — |
| | | | rs884266 | 0.96 | 1.60E−06 |
| | | | rs884265 | 0.96 | — |
| | | | rs913882 | 1 | 6.90E−07 |
| | | | rs6123749 | 1 | — |
| | | | rs6123750 | 1 | — |
| | | | rs6025924 | 1 | — |
| | | | rs6025926 | 1 | — |
| rs884266 | 8 | 11278 | | | |
| | | | rs6025914 | 0.92 | — |
| | | | rs6025917 | 0.91 | — |
| | | | rs12480795 | 0.92 | — |
| | | | rs6015147 | 0.96 | — |
| | | | rs6025921 | 0.8 | — |
| | | | rs6025923 | 0.96 | — |
| | | | rs884265 | 0.92 | — |
| | | | rs913882 | 0.95 | 6.90E−07 |
| | | | rs6123749 | 0.96 | — |
| | | | rs6123750 | 0.96 | — |
| | | | rs6025924 | 0.96 | — |
| | | | rs6025926 | 0.96 | — |
| | | | rs6025927 | 0.96 | 1.35E−06 |
| rs9405541 | 9 | 0 | | | |
| | | | rs9392358 | 1 | — |
| | | | rs9378319 | 1 | — |
| | | | rs12055694 | 1 | 2.77E−06 |
| | | | rs17134651 | 1 | — |
| | | | rs9405546 | 1 | — |
| | | | rs9378684 | 1 | — |
| rs869106 | 10 | 1429 | | | |
| | | | rs7033436 | 1 | — |
| | | | rs7042088 | 0.93 | — |
| | | | rs16906059 | 1 | — |
| | | | rs869105 | 0.92 | — |
| | | | rs9696012 | 0.83 | — |
| rs12055694 | 11 | 0 | | | |
| | | | rs9405541 | 1 | 2.38E−06 |
| | | | rs9392358 | 1 | — |
| | | | rs9378319 | 1 | — |
| | | | rs17134651 | 1 | — |
| | | | rs9405546 | 1 | — |
| | | | rs9378684 | 1 | — |
| rs28861531 | 12 | −9 | | | |
| rs10988087 | 13 | −2032 | | | |
| rs11618546 | 14 | 67501 | | | |
| rs894857 | 15 | −2597 | | | |
| rs12340584 | 16 | 0 | | | |
| rs6682365 | 17 | −31099 | | | |
| | | | rs11800854 | 1 | — |
| rs1573706 | 18 | 0 | | | |
| rs12968586 | 19 | −106453 | | | |
| | | | rs7232734 | 1 | — |
| | | | rs8099595 | 1 | — |
| | | | rs9952995 | 0.83 | — |
| | | | rs7244801 | 1 | — |
| rs11081859 | 20 | −122774 | | | |
| | | | rs4799760 | 0.92 | — |
| rs17104742 | 21 | 0 | | | |
| | | | rs17104665 | 1 | — |
| | | | rs998051 | 1 | 6.83E−06 |
| | | | rs2033471 | 1 | — |
| | | | rs1802027 | 1 | 6.79E−06 |

TABLE 3-continued

Annotated SNPs with p-val < or = 5*10E−05 from the GWAS of the composite phenotype
Thirty-eight (38) SNPs have been genotyped with the Human1M Illumina chip and 89 additional SNPs are
uniquely tagged by the genotyped SNPs. Among these 89 tagged SNPs, 20 are cross-represented within
the list of the 38 "taggers", ultimately leading to 69 tagged SNPs that are not present
on the Human 1M chip.

| | | | | | |
|---|---|---|---|---|---|
| rs10214633 | 22 | 0 | | | |
| rs1041897 | 23 | −18321 | | | |
| rs7955917 | 24 | −22481 | | | |
| | | | rs1905942 | 0.83 | 0.0064 |
| | | | rs1112925 | 0.83 | 0.0076 |
| | | | rs7963693 | 1 | — |
| | | | rs1683691 | 1 | — |
| | | | rs1713615 | 1 | — |
| | | | rs1713618 | 0.91 | — |
| | | | rs7979791 | 0.9 | — |
| | | | rs4882750 | 0.81 | — |
| | | | rs4882751 | 0.92 | — |
| rs6713772 | 25 | −9 | | | |
| | | | rs10864878 | 0.93 | — |
| | | | rs17007730 | 1 | 7.89E−06 |
| | | | rs10207898 | 1 | — |
| | | | rs11687082 | 1 | — |
| | | | rs13412899 | 1 | — |
| | | | rs10170186 | 1 | — |
| | | | rs10170543 | 0.93 | — |
| | | | rs6742690 | 1 | — |
| | | | rs13419434 | 1 | — |
| | | | rs11674429 | 1 | — |
| rs17575455 | 26 | 47985 | | | |
| | | | rs17575434 | 0.92 | 0.0003 |
| rs1802027 | 27 | 0 | | | |
| | | | rs17104665 | 1 | — |
| | | | rs998051 | 1 | 6.83E−06 |
| | | | rs2033471 | 1 | — |
| | | | rs17104742 | 1 | 4.86E−06 |
| rs998051 | 28 | 0 | | | |
| | | | rs17104665 | 1 | — |
| | | | rs2033471 | 1 | — |
| | | | rs1802027 | 1 | 6.79E−06 |
| | | | rs17104742 | 1 | 4.86E−06 |
| rs7714122 | 29 | 0 | | | |
| | | | rs17087180 | 1 | — |
| rs3742228 | 30 | 0 | | | |
| rs4483642 | 31 | 138319 | | | |
| | | | rs2374730 | 0.91 | — |
| | | | rs4565951 | 1 | — |
| | | | rs933863 | 1 | — |
| | | | rs933864 | 1 | — |
| rs12439713 | 32 | −2732 | | | |
| | | | rs7175350 | 1 | — |
| | | | rs7180867 | 1 | 0.0004 |
| | | | rs8035793 | 1 | — |
| | | | rs10520693 | 1 | — |
| | | | rs7183485 | 1 | — |
| | | | rs11633340 | 1 | — |
| | | | rs11638226 | 1 | — |
| | | | rs6416556 | 1 | — |
| | | | rs7178587 | 1 | 0.0001 |
| | | | rs6496716 | 1 | — |
| | | | rs17180345 | 1 | — |
| | | | rs4506872 | 1 | — |
| | | | rs4343256 | 1 | 1.01E−05 |
| | | | rs12593600 | 1 | — |
| | | | rs10083547 | 1 | — |
| | | | rs4306478 | 1 | — |
| | | | rs11855570 | 1 | — |
| rs13042992 | 33 | 0 | | | |
| rs17007730 | 34 | −9 | | | |
| | | | rs10864878 | 0.92 | — |
| | | | rs10207898 | 1 | — |
| | | | rs11687082 | 1 | — |
| | | | rs13412899 | 1 | — |
| | | | rs10170186 | 1 | — |
| | | | rs10170543 | 0.92 | — |
| | | | rs6742690 | 1 | — |
| | | | rs13419434 | 1 | — |
| | | | rs11674429 | 1 | — |
| | | | rs6713772 | 1 | 5.95E−06 |

TABLE 3-continued

Annotated SNPs with p-val < or = 5*10E-05 from the GWAS of the composite phenotype
Thirty-eight (38) SNPs have been genotyped with the Human1M Illumina chip and 89 additional SNPs are
uniquely tagged by the genotyped SNPs. Among these 89 tagged SNPs, 20 are cross-represented within
the list of the 38 "taggers", ultimately leading to 69 tagged SNPs that are not present
on the Human 1M chip.

| | | | | | |
|---|---|---|---|---|---|
| rs2277431 | 35 | 0 | | | |
| rs10931091 | 36 | −61118 | | | |
| | | | rs10931090 | 1 | — |
| | | | rs11899025 | 0.81 | — |
| | | | rs11884398 | 0.81 | 0.0037 |
| rs6558102 | 37 | 0 | | | |
| rs4343256 | 38 | −5050 | | | |

Tables 1-3 also include the identity of the closest genes to the SNPs identified as having a predictive value for the response to GA (GWAS significant SNPs), and "tagged SNPs" (SNPs which are in linkage disequilibrium with the GWAS significant SNPs). SNPs which are in linkage disequilibrium with the GWAS significant SNPs and/or reside in the closest genes may also serve to predict whether the subject is a responder or non-responder to GA.

We then compared the p values of the SNPs we found using the broad definition to results from the analysis of the narrow definition. This comparison confirmed that the same SNPs had a significant association with response to GA in both analyses, as presented in table 4.

is not limiting in nature. It would be appreciated by those of skill in the art that other sets of SNPs and combinations of certain SNPs with certain clinical variables may be obtained by methods known to the person skilled in the art, which would demonstrate a predictive value for the response to GA. Other predictive models created from SNPs from tables 1-3 and table 16 are presented in tables 17-36.

An analysis was performed which included responders and non-responders according to the narrow definition. Data from 33 patients classified as responders according to the narrow definition and from 41 patients classified as non-responders were obtained, which included genotypes of all 31 SNPs. Patients which were included in the following prediction

TABLE 4 results of GWAS using a narrow definition of the R/NR phenotype,
with corresponding p values also for the broad phenotype

| SNP | chromosome | Closest gene | Narrow Phenotype | Broad Phenotype |
|---|---|---|---|---|
| rs2521644 | 7 | NPY; OTTHUMG00000022973 | 6.48E−06 | 0.0003 |
| rs35603463 | 6 | AL713966.1 | 9.28E−06 | 0.0002 |
| rs4369324 | 10 | OTTHUMG00000019024; RP11-655H13.1 | 1.48E−05 | 9.45E−05 |
| rs1538123 | 10 | OTTHUMG00000019024; RP11-655H13.1 | 1.48E−05 | 0.0001 |
| rs17807445 | 6 | OTTHUMG00000016430; BCKDHB | 2.54E−05 | 0.0004 |
| rs17771939 | 8 | AC011118.1 | 2.62E−05 | 3.05E−07 |
| rs6584894 | 10 | OTTHUMG00000019024; RP11-655H13.1 | 2.90E−05 | 0.0003 |
| rs496486 | 3 | OTTHUMG00000150360; BBX | 3.18E−05 | 6.86E−05 |
| rs949298 | 11 | GRIK4; OTTHUMG00000048255 | 3.29E−05 | 3.38E−05 |
| rs948032 | 11 | GRIK4; OTTHUMG00000048255 | 3.29E−05 | 3.38E−05 |
| rs7086707 | 10 | OTTHUMG00000019024; RP11-655H13.1 | 3.65E−05 | 0.0001 |
| rs7093143 | 10 | OTTHUMG00000019024; RP11-655H13.1 | 3.65E−05 | 0.0003 |
| rs1415557 | 10 | OTTHUMG00000019024; RP11-655H13.1 | 3.65E−05 | 0.0003 |
| rs1007328 | 15 | AC012409.1 | 3.71E−05 | 0.0007 |
| rs12256889 | 10 | CYP26C1; OTTHUMG00000018766 | 4.34E−05 | 0.0008 |
| rs214526 | 6 | OTTHUMG00000014319; DEK | 4.35E−05 | 0.0018 |
| rs9315048 | 13 | ALOX5AP; OTTHUMG00000016677 | 4.38E−05 | 0.0008 |
| rs4445746 | 13 | ALOX5AP; OTTHUMG00000016677 | 4.38E−05 | 0.0015 |
| rs2155262 | 11 | GRIK4; OTTHUMG00000048255 | 4.65E−05 | 2.93E−05 |
| rs844626 | 6 | SAMD5; OTTHUMG00000015767 | 4.85E−05 | 0.0014 |
| rs947603 | 10 | CEP55; OTTHUMG00000018774 | 4.87E−05 | 0.0037 |

A Predictive Model Based on the SNPs Having a Predictive Value for the Response for GA Treatment A predictive model using the SNPs from table 2 was created in order to improve the predictive value by certain combinations of SNPs with certain genotypes. It should be emphasized that this specific model is created by a specific backward stepwise procedure, and is therefore intended to illustrate certain preferred embodiments of the invention and model consisting of 6 SNPs were 51 patients classified as responders, and 61 classified as non-responders, out of 599 patients in the FORTE cohort.

A backward stepwise logistic regression procedure led to the following predictive model which includes a set of 6 SNPs. The 6 SNPs and predictive values are presented in table 5. This model is also called FM1.

TABLE 5 results from a logistic regression analysis of R/NR to Copaxone with best resulting SNPs from the GWAS. The model has been performed with a backward stepwise procedure (probability of removal if p < 0.05) and lead to a pattern composed by 6 SNPs,.

| resp1_amir | Odds Ratio | Std. Err. | z | P > \|z\| | [95% Conf. Interval] | |
|---|---|---|---|---|---|---|
| rs2521644_g | 15.58231 | 14.09115 | 3.04 | 0.002 | 2.647807 | 91.70168 |
| rs12256889_a | 11.63899 | 11.44968 | 2.49 | 0.013 | 1.692618 | 80.03346 |
| rs214526_a | 10.38811 | 9.471729 | 2.57 | 0.010 | 1.739496 | 62.03686 |
| rs17771939_g | .0332771 | .0338315 | −3.35 | 0.001 | .0045369 | .2440786 |
| rs496486_c | .0205013 | .0344571 | −2.31 | 0.021 | .0007606 | .5526131 |
| rs949298_a | .1027731 | .0902505 | −2.59 | 0.010 | .0183821 | .5745987 |

In addition, the sensitivity, specificity, positive predictive value (PPV) and negative predictive value (NPV) were analyzed to determine the usefulness of the predictive model to predict the response to GA treatment. The sensitivity of the test is defined as the proportion of clinical responders who are correctly identified as such. The specificity on the other hand measures the proportion of negatives which are correctly identified. The PPV of a test is defined as the proportion of patients with positive test results who are correctly identified, whereas the NPV of a test is the proportion of patients with negative test results who are correctly identified.

The predictive values derived from the logistic regression in table 5 are presented in table 6.

TABLE 6

Classification table from the logistic regression as in Table 7

| Classified | True | | Total |
|---|---|---|---|
| | R | NR | |
| (R) | 29 | 3 | 32 |
| (NR) | 4 | 38 | 42 |
| Total | 33 | 41 | 74 |

Classified + if predicted Pr(R) >= .5
True R defined as resp1_amir != 0

| Sensitivity | Pr(+\|R) | 87.88% |
|---|---|---|
| Specificity | Pr(−\|NR) | 92.68% |
| Positive predictive value | Pr(R\|+) | 90.62% |
| Negative predictive value | Pr(NR\|−) | 90.48% |
| False + rate for true ~D | Pr(+\|NR) | 7.32% |
| False − rate for true D | Pr(−\|R) | 12.12% |
| False + rate for classified + | Pr(NR\|+) | 9.38% |
| False − rate for classified − | Pr(R\|−) | 9.52% |
| Correctly classified | | 90.54% |

Based on this model, it can be concluded that the specific set of SNPs presented in table 5 can be used to determine whether the patient is responder to GA.

The response probability of a specific patient was calculated according to the model. Following the genotyping of the patient at the relevant SNPs, the values of the 6 SNPs were recoded to numeric values as described in the following tables (7a-f):

TABLE 7a

| rs2521644 | rs2521644_g |
|---|---|
| TT | 0 |
| CT | 1 |
| CC | 2 |

TABLE 7b

| rs12256889 | rs12256889_a |
|---|---|
| CC | 0 |
| AC | 1 |
| AA | 2 |

TABLE 7c

| rs214526 | rs214526_a |
|---|---|
| CC | 0 |
| AC | 1 |
| AA | 2 |

TABLE 7d

| rs17771939 | rs17771939_g |
|---|---|
| TT | 0 |
| CT | 1 |
| CC | 2 |

TABLE 7e

| rs496486 | rs496486_c |
|---|---|
| AA | 0 |
| AC | 1 |
| CC | 2 |

TABLE 7f

| rs949298 | rs949298_a |
|---|---|
| GG | 0 |
| AG | 1 |
| AA | 2 |

Then, βX was calculated according to the following formula:

$$\beta X = -1.6546 + 2.7614 \cdot rs2521644_g + 3.0106 \cdot rs12256889_a + 2.4996 \cdot rs214526_a - 2.6679 \cdot rs17771939_g - 3.6010 \cdot rs496436_c - 2.1277 \cdot rs949298\_a$$

and the response probability p(Response) was calculated using the formula:

$$P(\text{Response}) = \frac{e^{\beta X}}{1 + e^{\beta X}}$$

Patients with p(Response) above 0.5 were predicted to be responders and patients with p(Response) below 0.5 were predicted to be non-responders. When the model was retrospectively applied to the full cohort of 599 FORTE patients, we observed that the annualized relapse rate (ARR) in patients genetically predicted as responders was reduced by 62% compared to all patients, and by 76% compared to non-responders (p<0.0001). When we applied the model retrospectively to a second independent cohort of 79 patients, the model could identify subpopulations genetically predicted to be responders and non-responders with respectively lower (for responders) and higher (for non-responders) relapse rate. In the placebo-treated arm no specific pattern could be observed. This may suggest that this genetic model is specific to response to GA and not to the MS disease natural course.

Two other variations of the model presented in table 5 were further created, as presented in table 8:

TABLE 8

| Model | SNPs in model |
|---|---|
| FM1a | rs12256889 rs17771939 rs214526 rs2521644 rs496486 rs2511064 |
| FM2 | rs12256889 rs17771939 rs2511064 rs2521644 |

The response probability of a specific patient was calculated according to each model. Following the genotyping of the patient at the relevant SNPs, the values of the SNPs were recoded to numeric values as described in the following tables (9a-f):

TABLE 9a

| rs12256889 | Recoded value |
|---|---|
| AA | 2 |
| AC | 1 |
| CC | 0 |

TABLE 9b

| rs17771939 | Recoded value |
|---|---|
| CC | 2 |
| CT | 1 |
| TT | 0 |

TABLE 9c

| rs2511064 | Recoded value |
|---|---|
| AA | 0 |
| AG | 1 |
| GG | 2 |

TABLE 9d

| rs2521644 | Recoded value |
|---|---|
| TT | 0 |
| CT | 1 |
| CC | 2 |

TABLE 9e

| rs496486 | Recoded value |
|---|---|
| AA | 0 |
| AC | 1 |
| CC | 2 |

TABLE 9f

| rs214526 | Recoded value |
|---|---|
| AA | 2 |
| AC | 1 |
| CC | 0 |

Then, $\beta X$ was calculated by multiplying the recoded value of each of the defined numeric variables by the coefficient in the table (Table 10 for the FM1 model, table 11 for the FM2 model):

TABLE 10

| FM1a model parameter | Coefficient |
|---|---|
| Intercept | −5.0447 |
| rs12256889 | 2.8853 |
| rs17771939 | −1.9024 |
| rs214526 | 3.2451 |
| rs2521644 | 1.9614 |
| rs496486 | −2.2393 |
| rs2511064 | 1.7477 |

TABLE 11

| FM2 model parameter | Coefficient |
|---|---|
| Intercept | −2.8016 |
| rs12256889 | 1.5847 |
| rs17771939 | −0.9850 |
| rs2521644 | 1.1482 |
| rs2511064 | 1.1486 | and the response probability p(Response) was calculated using the formula:

$$P(\text{Response}) = \frac{e^{\beta X}}{1 + e^{\beta X}}$$

GWAS Using a Composite/Continuous Measure

A composite measure has been created using a multivariate algorithm that considers diverse measures (Number of Relapses, Number of new T2 lesions and number of T1 lesions) in a unique quantitative measure of Response to Copaxone. Then, we performed a quantitative GWAS looking for SNPs that may distinguish R from NR patients. As described above, analysis using the composite measure led to the identification of 38 SNPs having p value of $10^{-4}$ or lower, which are presented in table 3.

Pathway Analyses

We created a list of genes identified via SNPs by the GWAS analyses for the broad and narrow phenotypes. The two lists are presented in Table 12. Based on these genes, we identified several canonical pathways which are significantly enriched using the broad or the narrow definitions. Beginning with the list of "genes" presented in table 12, we could initially find out which canonical pathways are significantly enriched using the broad (Table 13) or the narrow (Table 14) phenotype.

TABLE 12

List of genes identified via SNPs from the GWAS analyses

| BROAD PHENO | NARROW PHENO |
|---|---|
| AC016885.1 | AC011118.1 |
| CYP24A1 | CYP24A1 |
| ASNS | ASNS |
| TAC1 | TAC1 |
| ASNS | ASNS |
| AC083939.1 | SPANXN4 |
| HPSE2 | GMDS |
| SPANXN4 | C10orf112 |
| AC083939.1 | DNAJC13 |
| GMDS | NPY |
| C10orf112 | AL713966.1 |
| C10orf112 | BCKDHB |
| DNAJC13 | RP11-655H13.1 |
|  | BBX |
|  | GRIK4 |
|  | AC012409.1 |
|  | CYP26C1 |
|  | DEK |
|  | ALOX5AP |
|  | SAMD5 |
|  | CEP55 |
|  | AC093762.1 |
|  | AL138825.1 |

TABLE 13

Canonical pathways significantly enriched by top SNPs in broad definition

| Pathway | P-value | Genes |
|---|---|---|
| Stilbene, Coumarine and Lignin Biosynthesis | 1.28E−02 | CYP24A1 |
| Ascorbate and Aldarate Metabolism | 1.16E−02 | CYP24A1 |
| Biosynthesis of Steroids | 7.81E−03 | CYP24A1 |
| Neuroprotective Role of THOP1 in Alzheimer's Disease | 1.85E−02 | TAC1 |

TABLE 13-continued

Canonical pathways significantly enriched by top SNPs in broad definition

| Pathway | P-value | Genes |
|---|---|---|
| Alanine and Aspartate Metabolism | 1.14E−02 | ASNS |
| Nitrogen Metabolism | 7.52E−03 | ASNS |
| Fructose and Mannose Metabolism | 6.90E−03 | GMDS |
| VDR/RXR Activation | 1.25E−02 | CYP24A1 |
| Sphingolipid Metabolism | 8.62E−03 | CYP24A1 |
| Neuropathic Pain Signaling In Dorsal Horn Neurons | 9.71E−03 | TAC1 |
| NRF2-mediated Oxidative Stress Response | 5.46E−03 | DNAJC13 |

TABLE 14

Canonical pathways significantly enriched by top SNPs in narrow definition

| Pathway | P-value | Genes |
|---|---|---|
| Stilbene, Coumarine and Lignin Biosynthesis | 2.56E−02 | CYP24A1, BCKDHB |
| Ascorbate and Aldarate Metabolism | 2.33E−02 | CYP24A1, BCKDHB |
| Aminophosphonate Metabolism | 1.54E−02 | BCKDHB |
| Biosynthesis of Steroids | 7.81E−03 | CYP24A1 |
| Pentose Phosphate Pathway | 1.12E−02 | BCKDHB |
| Neuroprotective Role of THOP1 in Alzheimer's Disease | 1.85E−02 | TAC1 |
| Alanine and Aspartate Metabolism | 1.14E−02 | ASNS |
| Nitrogen Metabolism | 7.52E−03 | ASNS |
| Pentose and Glucuronate Interconversions | 6.67E−03 | BCKDHB |
| Glutamate Receptor Signaling | 1.43E−02 | GRIK4 |
| Fructose and Mannose Metabolism | 6.90E−03 | GMDS |
| Eicosanoid Signaling | 1.20E−02 | ALOX5AP |
| Valine, Leucine and Isoleucine Degradation | 9.01E−03 | BCKDHB |
| Leptin Signaling in Obesity | 1.22E−02 | NPY |
| Ubiquinone Biosynthesis | 8.40E−03 | BCKDHB |
| VDR/RXR Activation | 1.25E−02 | CYP24A1 |
| Tyrosine Metabolism | 4.95E−03 | BCKDHB |
| Arginine and Proline Metabolism | 5.46E−03 | BCKDHB |
| Pyruvate Metabolism | 6.71E−03 | BCKDHB |
| Sphingolipid Metabolism | 8.62E−03 | CYP24A1 |
| Amyotrophic Lateral Sclerosis Signaling | 8.93E−03 | GRIK4 |
| Neuropathic Pain Signaling In Dorsal Horn Neurons | 9.71E−03 | TAC1 |
| Tryptophan Metabolism | 3.95E−03 | BCKDHB |
| CREB Signaling in Neurons | 5.10E−03 | GRIK4 |
| NRF2-mediated Oxidative Stress Response | 5.46E−03 | DNAJC13 |
| Purine Metabolism | 2.28E−03 | BCKDHB |

With the same enrichment strategy, we can generate various pathways that our current findings suggest, and that are related to disorder-related pathways, Molecular and cellular functions and Physiological system development and functions. Table 15 (a and b) shows a summary of the pathways findings.

TABLE 15a-15b 15.a BROAD PHENOTYPE
TOP BIO FUNCTIONS

| Disease and disorders | P-value | Genes |
|---|---|---|
| Neurological Disease | 1.66E−03-3.68E−02 | GMDS, TAC1, HPSE2, ASNS, C10ORF112 |
| Cancer | 1.9E−03-1.9E−03 | CYP24A1 |
| Endocrine System Disorders | 1.9E−03-2.73E−02 | CYP24A1, GMDS, HPSE2, C10ORF112 |
| Connective Tissue Disorders | 4.22E−02-4.22E−02 | GMDS, TAC1, HPSE2 |
| Genetic Disorder | 1.9E−03-3.68E−02 | CYP24A1, GMDS, TAC1, HPSE2, ASNS, C10ORF112 |
| Psychological Disorders | 1.98E−03-3.37E−02 | GMDS, TAC1, HPSE2, C10ORF112 |

TABLE 15a-15b-continued

| | P-value | P-value | |
|---|---|---|---|
| Molecular and cellular functions | | | |
| Amino Acid Metabolism | 4.76E−04-1.93E−02 | TAC1 | |
| Cell Cycle | 4.76E−04-5.69E−03 | TAC1 | |
| Cell Signaling | 4.76E−04-2.63E−02 | TAC1 | |
| Drug Metabolism | 4.76E−04-3.37E−02 | CYP24A1, TAC1 | |
| Lipid Metabolism | 4.76E−04-3.74E−02 | CYP24A1, TAC1 | |
| Physiological System Development and Functions | | | |
| Connective Tissue Development and Function | 4.76E−04-2.85E−03 | TAC1 | |
| Digestive System Development and Function | 4.76E−04-2.45E−02 | TAC1 | |
| Organ Morphology | 4.76E−04-2.38E−03 | TAC1 | |
| Skeletal and Muscular System Development and Function | 4.76E−04-8.53E−03 | CYP24A1, TAC1 | |
| Tissue Morphology | 4.76E−04-1.93E−02 | TAC1 | |

15.b NARROW PHENOTYPE TOP BIO FUNCTIONS

| Disease and disorders | P-value | Genes |
|---|---|---|
| Connective Tissue Disorders | 2.93E−04-2.72E−02 | NPY, DEK, GMDS, GRIK4, SAMD5, ALOX5AP, TAC1, BCKDHB |
| Inflammatory Disease | 2.93E−04-2.72E−02 | NPY, DEK, GMDS, GRIK4, SAMD5, ALOX5AP, TAC1, C10OR F112, BCKDHB |
| Skeletal and Muscular Disorders | 2.93E−04-2.72E−02 | NPY, DEK, GMDS, GRIK4, SAMD5, ALOX5AP, TAC1, ASNS, BCKDHB |
| Hypersensitivity Response | 1.02E−03-7.11E−03 | NPY, TAC1 |
| Inflammatory Response | 1.02E−03-4E−02 | NPY, DEK, ALOX5AP, TAC1 |

| | P-value | P-value |
|---|---|---|
| Molecular and cellular functions | | |
| Cell Morphology | 1.84E−05-2.82E−02 | NPY, GRIK4, TAC1 |
| Amino Acid Metabolism | 7.77E−04-2.52E−02 | NPY, TAC1, BCKDHS |
| Molecular Transport | 7.77E−04-3.63E−02 | NPY, CYP24A1, GRIK4, ALOX5AP, TAC1 |
| Small Molecule Biochemistry | 7.77E−04-3.71E−02 | NPY, CYP24A1, GMDS, CYP26C1, ALOX5AP, TAC1, BCKDHB |
| Cell Cycle | 1.02E−03-4.98E−02 | DEK, TAC1, ASNS, CEP55 |
| Physiological System Development and Functions | | |
| Behavior | 5.99E−04-4.88E−02 | NPY, TAC1 |
| Nervous System Development and Function | 2.1E−03-4.67E−02 | NPY, GRIK4, TAC1 |
| Connective Tissue Development and Function | 1.02E−03-2.62E−02 | NPY, TAC1 |
| Digestive System Development and Function | 1.02E−03-4.59E−02 | NPY, TAC1 |
| Organ Morphology | 1.02E−03-5.09E−03 | TAC1, ALOX5AP |

Figure 2:
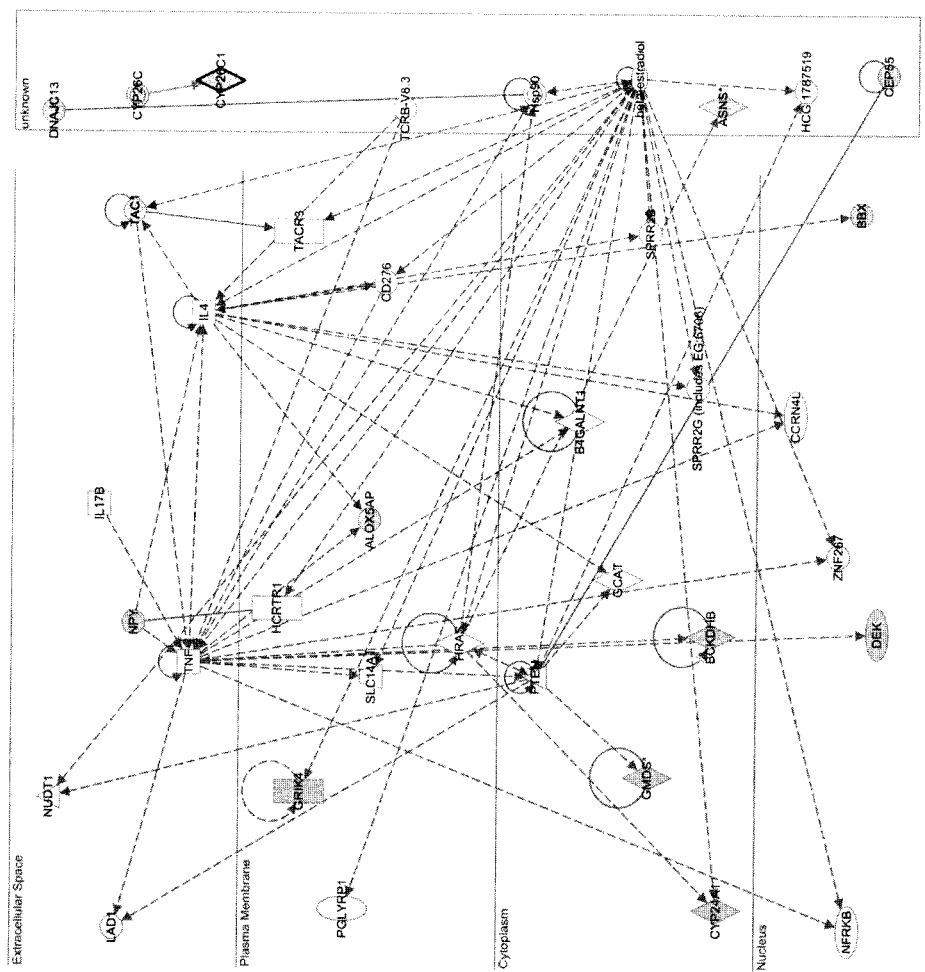
FIG. 2. Merging of the two mostly enriched networks for narrow phenotype definition (organized by cellular compartments). Genes with the light grey symbols are from the GWAS findings, while the others with "empty" symbols are their pathways' specific members, and have not been identified by any GWAS.

As examples, FIGS. 1-2 were created using the Ingenuity Systems Pathway Analysis software, show how a set of genes from some of the enriched pathways reported in Table 15 can be arranged within the blueprint of a cellular layout, to suggest possible functional hypotheses of how genes indirectly related to Response to Copaxone by proxy SNPs may act.

FIG. 1 relates to the broad phenotype findings, points to genes related to Inflammatory Response, Cell-To-Cell Signaling and Interaction and Hematological System Development and Function (AIM2, ANXA11, ASNS, CAR, CYB561, CYP24A1, DDR2, DNAJB4, DNAJB6, DNAJB7, DNAJC13, EOMES, ESM1, GDPmannose 4,6-dehydratase, GLS, GMDS, GPNMB, H6PD, HLA Class I, HLA-DMA, HNF4A, Hsp70, IFI30, IFNG, IGH-2, IL17RB, LY6A, MEFV, MRC1, NDRG4, PTEN, ROBO3, SMTN, TAC1, TAC4, TGFB1, TTC28, TYMP, ZFPM1)

FIG. 2, relates to the narrow phenotype findings, points to pathways relating to Cell Death; Cell-To-Cell Signaling and Interaction; Cellular Development via another set of genes that are again identified by the resulting significant SNPs from the GWAS on narrow phenotype (ALOX5AP, ASNS, B4GALNT1, BBX, BCKDHB, beta-estradiol, CCRN4L, CD276, CEP55, CYP24A1, CYP26C, CYP26C1, DEK, DNAJC13, GCAT, GMDS, GRIK4, HCG 1787519, HCRTR1, HRAS, Hsp90, IL17B, IL4, LAD1, NFRRB, NPY, NUDT1, PGLYRP1, PTEN, SLC14A1, SPRR2B, SPRR2G (includes EG:6706), TAC1, TACR3, TCRB-V8.3, TNF, ZNF267).

We have further repeated the analysis using the Ingenuity Systems Pathway Analysis software and created a modified pathway analysis.

Figure 3:
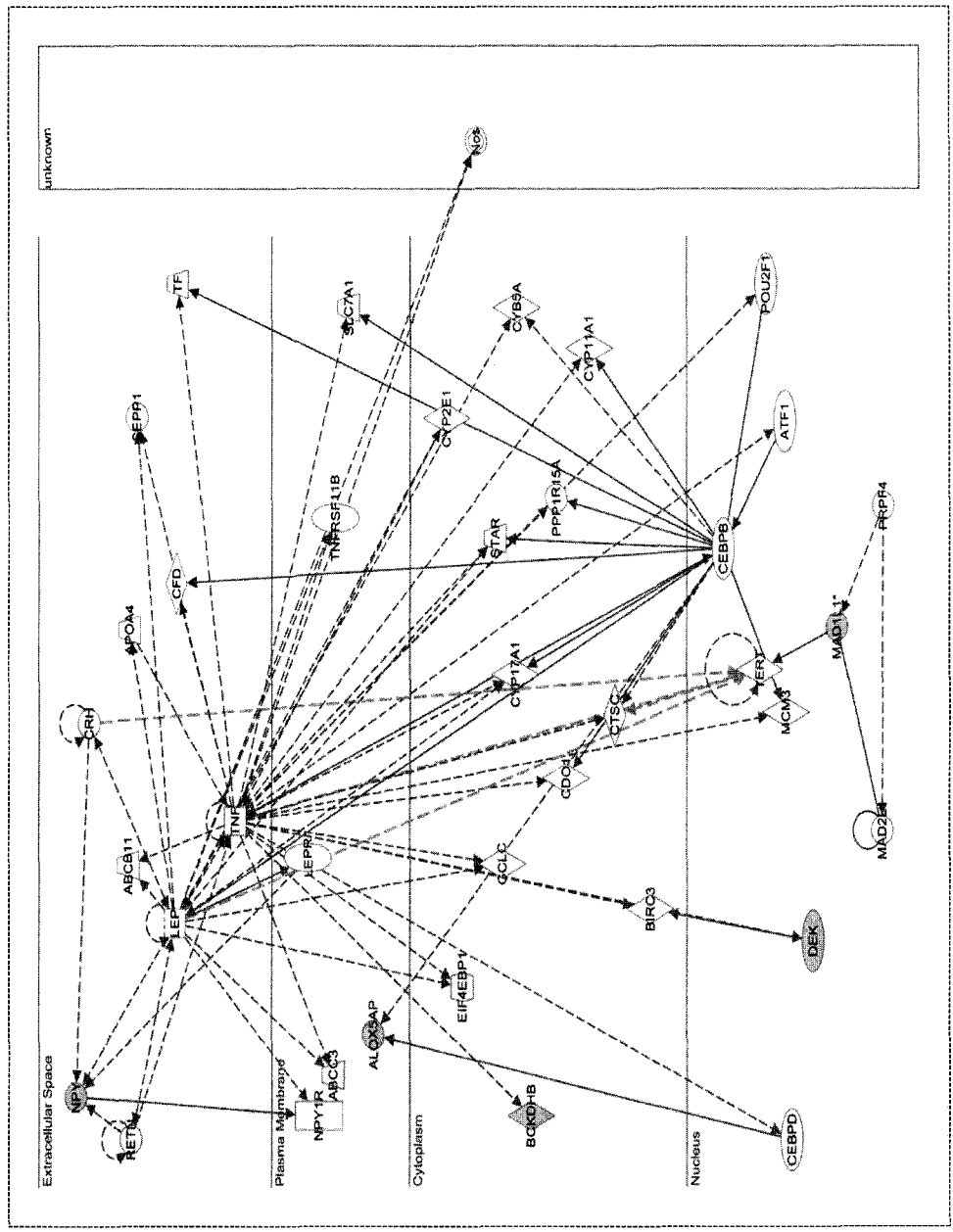
FIG. 3. Merging two networks for narrow phenotype definition (organized by cellular compartments). Genes with the light grey symbols are from the GWAS findings, while the others with "empty" symbols are their pathways' specific members, and have not been identified by any GWAS.

FIG. 3, relates to the narrow phenotype findings, points to pathways relating to connective Tissue Disorders, Metabolic Disease, Lipid Metabolism via another set of genes that are relating to Cell Cycle, DNA Replication, Recombination, and Repair, Cellular Growth and Proliferation. The two networks are functionally related to each other and together make a single large Gene Regulatory Network orchestrated by TNFα and CEBPB. A third, independent pathway is related to GRIK4 (Glutamatergic transmission).

Prediction Using the Broad, Narrow, and Composite Definitions of R/NR

We tested 81 GWAS significant SNPs from tables 1-3 and SNPs which are in linkage disequilibrium with those SNPS ("tagged SNPs") in a confirmation study. The SNPs were genotypes by the TaqMan Open Array assay and the predictive value in the FORTE cohort was evaluated. Table 16 suggests an interpretation of genotype data to Response/Non-Response prediction according to the narrow definition. For the SNPs and tagged SNPs originating in the broad and narrow phenotypes, PPV, NPV, specificity and sensitivity values are given. For SNPs and tagged SNPs originating in the composite phenotype, R square is given. When tested in non-treated patients (from the CORAL study), none of the SNPs that were found highly associated with response in the FORTE study were found associated with response. Table 16a presents data for the broad phenotype, Table 16b presents data for the narrow and composite phenotypes.

TABLE 16a

| | | | | | | | | | |
|---|---|---|---|---|---|---|---|---|---|
| | | | | Broad Phenotype | | | | | |
| SNP ID | R Allele | NR Allele | analysis according to phenotype: | response definition | P-value | specificity | sensitivity | positive predicting value | negative predicting value |
| rs1007328 | TT | CC | broad/narrow | broad | 0.00125 | 37.50% | 97.70% | 85.80% | 80.80% |
| rs10083547 | GG | CC, CG | composite/broad | broad | 0.04799 | 35.60% | 97.20% | 84.70% | 77.80% |
| rs10136012 | GG | TT | composite/broad | broad | 0.08301 | 32.20% | 97.20% | 84.10% | 76.00% |
| rs10214633 | — | — | composite/narrow | broad | 0.36439 | 34.50% | 96.90% | 85.00% | 74.10% |
| rs10277267 | AA, AG | GG | broad/narrow | broad | 0.25544 | 35.60% | 96.80% | 84.60% | 75.00% |
| rs1040194 | GG | AA, AG | broad/narrow | broad | 0.00787 | 35.60% | 96.80% | 84.80% | 75.00% |
| rs1041897 | CC | CT, TT | composite | broad | 0.58427 | 31.00% | 96.30% | 84.10% | 69.20% |
| rs10853605 | CC | TT | broad/narrow/composite | broad | 0.00033 | 42.40% | 97.30% | 86.30% | 80.60% |
| rs10931091 | TT | CC, CT | composite | broad | 0.92888 | 30.50% | 96.30% | 83.50% | 69.20% |
| rs10935015 | AA | AG, GG | broad/narrow/composite | broad | 0.03250 | 39.00% | 96.80% | 85.40% | 76.70% |
| rs10935016 | CC | AA, AC | broad/narrow/composite | broad | 0.02452 | 39.70% | 96.40% | 85.90% | 74.20% |
| rs10935019 | AA | AG, GG | broad/narrow/composite | broad | 0.07243 | 37.30% | 96.80% | 85.10% | 75.90% |
| rs10950359 | AG, GG | AA | narrow | broad | 0.10917 | 35.00% | 96.70% | 84.20% | 75.00% |
| rs10950371 | CC, CT | TT | broad/narrow | broad | 0.03299 | 36.70% | 97.30% | 85.10% | 78.60% |
| rs10988087 | AA | AG, GG | composite | broad | 0.97429 | 34.50% | 96.80% | 84.70% | 74.10% |
| rs11009827 | CC | AA, AC | broad | broad | 0.03226 | 36.20% | 97.30% | 85.20% | 77.80% |
| rs11009835 | CC | CT, TT | broad | broad | 0.06069 | 34.50% | 97.30% | 84.90% | 76.90% |
| rs11081859 | AA | AG, GG | composite | broad | 0.31158 | 32.20% | 96.70% | 83.70% | 73.10% |
| rs11599624 | AG, GG | AA | broad/narrow/composite | broad | 0.00254 | 41.40% | 96.20% | 85.50% | 75.00% |
| rs11617134 | TT | CC, CT | composite/broad | broad | 0.00609 | 42.40% | 96.80% | 86.20% | 78.10% |
| rs11618546 | CC, CG | GG | composite | broad | 0.78326 | 31.70% | 96.40% | 84.00% | 70.40% |
| rs11694344 | AA | CC | broad/narrow/composite | broad | 0.00449 | 39.00% | 97.20% | 85.50% | 79.30% |
| rs11709339 | TT | CC, CT | broad/narrow/composite | broad | 0.02699 | 39.70% | 97.30% | 85.90% | 79.30% |
| rs11719825 | TT | GG, GT | broad/narrow/composite | broad | 0.04708 | 35.10% | 97.20% | 84.70% | 76.90% |
| rs11761457 | TT, CT | CC | broad/narrow | broad | 0.05228 | 35.60% | 97.30% | 84.90% | 77.80% |
| rs11907046 | CC | TT | broad/narrow | broad | 0.00115 | 43.30% | 95.90% | 86.20% | 74.30% |
| rs12055694 | GG | AA, AG | broad/narrow/composite | broad | 0.00789 | 39.00% | 96.80% | 85.40% | 76.70% |
| rs12256889 | AA, AC | CC | broad/narrow/composite | broad | 0.01840 | 37.30% | 96.80% | 85.10% | 75.90% |
| rs1229542 | CC, CA | AA | broad | broad | 0.03832 | 31.00% | 96.40% | 84.30% | 69.20% |
| rs1229553 | TT | CC, CT | composite/broad | broad | 0.02602 | 35.00% | 96.40% | 84.70% | 72.40% |
| rs1229555 | CC | CT, TT | composite/broad | broad | 0.02523 | 36.20% | 96.90% | 85.40% | 75.00% |
| rs1229558 | GG | AA, AG | composite | broad | 0.34952 | 33.90% | 97.70% | 85.40% | 79.20% |
| rs1229562 | CC, CT | TT | composite/broad | broad | 0.02149 | 35.60% | 96.70% | 84.50% | 75.00% |
| rs1229563 | CC | CT, TT | composite/broad | broad | 0.02734 | 35.60% | 96.80% | 84.80% | 75.00% |
| rs1229564 | CC | CT, TT | composite/broad | broad | 0.02309 | 35.60% | 96.80% | 84.90% | 75.00% |
| rs1229568 | CC | CT, TT | composite/broad | broad | 0.02316 | 35.60% | 96.70% | 84.60% | 75.00% |
| rs12340584 | AA | AG, GG | composite | broad | 0.57078 | 35.00% | 97.30% | 84.80% | 77.80% |
| rs1234567 | TT | CC, CT | composite/broad | broad | 0.02755 | 35.00% | 96.40% | 84.70% | 72.40% |
| rs1234947 | TT | CC, CT | composite/broad | broad | 0.02605 | 35.00% | 96.40% | 84.60% | 72.40% |
| rs1237625 | GG | AA, AG | composite/broad | broad | 0.02189 | 35.60% | 96.80% | 84.80% | 75.00% |
| rs12488259 | CC | AA, AC | broad/narrow/composite | broad | 0.02922 | 33.90% | 96.80% | 84.50% | 74.10% |
| rs12494606 | AA | AG, GG | broad/narrow/composite | broad | 0.06989 | 37.30% | 96.80% | 85.00% | 75.90% |
| rs12496278 | GG | CC, CG | broad/narrow/composite | broad | 0.01703 | 38.30% | 96.40% | 85.10% | 74.20% |
| rs12524041 | AT | | broad/narrow | broad | 0.01216 | 32.20% | 96.40% | 84.10% | 70.40% |
| rs12529764 | CT | | broad/narrow | broad | 0.01478 | 32.80% | 96.30% | 84.10% | 70.40% |
| rs12532459 | GT, TT | GG | narrow | broad | 0.20971 | 37.30% | 96.70% | 84.90% | 75.90% |
| rs12540494 | GG | AA, AG | narrow | broad | 0.14854 | 37.30% | 96.80% | 85.10% | 75.90% |
| rs12593600 | TT | CC, CT | broad/narrow/composite | broad | 0.03049 | 36.20% | 97.30% | 85.20% | 77.80% |
| rs12633010 | GG | GT | broad/narrow | broad | 0.04672 | 38.60% | 97.30% | 86.20% | 78.60% |
| rs12637073 | GG | AA, AG | broad/narrow/composite | broad | 0.01574 | 40.00% | 95.90% | 85.40% | 72.70% |
| rs12639443 | CC | CT, TT | broad/narrow/composite | broad | 0.01513 | 39.00% | 95.90% | 85.50% | 71.90% |
| rs1264423 | TT | | broad/narrow | broad | 0.04086 | 37.30% | 96.80% | 85.10% | 75.90% |
| rs1282540 | GG | AA, AG | broad/narrow | broad | 0.01061 | 33.30% | 96.80% | 84.60% | 73.10% |
| rs1282546 | GG | AA, AG | broad/narrow | broad | 0.00800 | 35.60% | 96.80% | 84.70% | 75.00% |
| rs12968586 | GG | AA, AG | composite | broad | 0.74958 | 31.70% | 96.40% | 83.90% | 70.40% |
| rs1299325 | GG | CC, CG | broad/narrow | broad | 0.00972 | 35.60% | 96.80% | 84.70% | 75.00% |
| rs13021482 | CC, CT | | broad | broad | 0.01565 | 36.50% | 96.90% | 85.10% | 76.00% |
| rs13042992 | TT | GG, GT | composite/broad | broad | 0.02245 | 34.50% | 96.70% | 84.50% | 74.10% |
| rs1320648 | TT | CC, CT | broad/narrow | broad | 0.00037 | 36.20% | 95.90% | 85.10% | 70.00% |

TABLE 16a-continued

Broad Phenotype

| SNP ID | R Allele | NR Allele | analysis according to phenotype: | response definition | P-value | specificity | sensitivity | positive predicting value | negative predicting value |
|---|---|---|---|---|---|---|---|---|---|
| rs13238613 | CC, CT | TT | broad/narrow | broad | 0.04644 | 35.60% | 97.30% | 84.90% | 77.80% |
| rs13245980 | AG, GG | AA | narrow | broad | 0.16285 | 37.30% | 96.80% | 85.20% | 75.90% |
| rs1415557 | AA, AG | | broad/narrow | broad | 0.01902 | 33.90% | 96.80% | 84.30% | 74.10% |
| rs1538123 | CT, TT | CC | broad/narrow | broad | 0.00422 | 39.00% | 96.80% | 85.50% | 76.70% |
| rs1573706 | CC | CT, TT | broad/narrow/composite | broad | 0.00645 | 44.10% | 97.20% | 86.50% | 81.30% |
| rs1591661 | CT, TT | CC | broad/narrow | broad | 0.00665 | 39.00% | 96.80% | 85.30% | 76.70% |
| rs1611185 | CT | CC | broad/narrow/composite | broad | 0.00162 | 38.90% | 97.60% | 86.10% | 80.80% |
| rs1683691 | CC | CT, TT | composite | broad | 0.20336 | 37.30% | 96.80% | 85.10% | 75.90% |
| rs16999008 | GG | AA, AG | broad/narrow | broad | 0.00079 | 44.10% | 96.00% | 86.60% | 74.30% |
| rs17007730 | AA | AG, GG | composite | broad | 0.28369 | 31.00% | 97.70% | 84.20% | 78.30% |
| rs17087180 | AA | AG, GG | composite | broad | 0.44158 | 29.80% | 97.20% | 83.90% | 73.90% |
| rs17104665 | AA, GG | AG | composite | broad | 0.89875 | 31.00% | 96.70% | 83.80% | 72.00% |
| rs17104742 | AA, GG | AG | composite | broad | 0.84851 | 31.60% | 96.80% | 84.50% | 72.00% |
| rs17134651 | TT | CC, TT | broad/narrow/composite | broad | 0.00970 | 39.00% | 96.80% | 85.50% | 76.70% |
| rs17575455 | CC | AA | composite | broad | 0.10700 | 37.30% | 96.40% | 85.10% | 73.30% |
| rs17588454 | AA | AG, GG | broad/narrow/composite | broad | 0.00670 | 40.70% | 96.80% | 85.80% | 77.40% |
| rs17666347 | TT | CC, CT | composite | broad | 0.72869 | 33.90% | 96.30% | 84.30% | 71.40% |
| rs17771939 | TT | CC | broad/narrow | broad | 0.00006 | 47.50% | 95.00% | 87.00% | 71.80% |
| rs17807327 | AA, AC | | broad/narrow | broad | 0.01086 | 32.20% | 96.30% | 84.10% | 70.40% |
| rs17807445 | CC, CT | | broad/narrow | broad | 0.01540 | 33.30% | 96.40% | 84.30% | 71.40% |
| rs1886308 | | GG, GT | broad/narrow | broad | 0.00115 | 43.30% | 96.00% | 86.30% | 74.30% |
| rs1892974 | AA | TT | broad/narrow | broad | 0.00006 | 37.30% | 94.60% | 85.10% | 64.70% |
| rs1941973 | CT | CC, TT | composite | broad | 0.71879 | 30.00% | 96.80% | 83.50% | 72.00% |
| rs2033471 | GG | CG | composite | broad | 0.99912 | 32.20% | 96.90% | 84.40% | 73.10% |
| rs2088713 | AA | AC | broad/narrow/composite | broad | 0.01689 | 40.40% | 96.30% | 85.80% | 74.20% |
| rs214526 | AA, AC | CC | narrow | broad | 0.18675 | 34.50% | 97.30% | 84.90% | 76.90% |
| rs2155262 | GG | GG, CG | broad/narrow | broad | 0.00006 | 39.00% | 95.00% | 85.20% | 67.60% |
| rs2177073 | CC | AA, AC | composite/broad | broad | 0.02974 | 35.00% | 95.90% | 84.50% | 70.00% |
| rs2187495 | CC | CT, TT | broad/narrow | broad | 0.00007 | 38.30% | 95.10% | 85.10% | 67.60% |
| rs2277431 | CC | CT, TT | composite | broad | 0.96105 | 33.30% | 96.40% | 84.30% | 71.40% |
| rs2305623 | | GG, GT | narrow | broad | 0.17456 | 33.90% | 96.80% | 84.50% | 74.10% |
| rs2374730 | AA | AG | composite | broad | 0.70015 | 35.00% | 96.90% | 84.80% | 75.00% |
| rs2461319 | TT, CT | CC | narrow | broad | 0.17373 | 32.20% | 97.30% | 84.20% | 76.00% |
| rs2487889 | GG | AG | broad/narrow | broad | 0.00113 | 39.00% | 97.30% | 85.50% | 79.30% |
| rs2487896 | GG | AG | broad/narrow | broad | 0.00094 | 41.70% | 96.90% | 86.10% | 78.10% |
| rs2508806 | TT | CC, CT | broad/narrow | broad | 0.00007 | 38.20% | 95.80% | 85.70% | 70.00% |
| rs2511064 | GG | AA, AG | broad/narrow | broad | 0.00007 | 42.40% | 94.60% | 86.10% | 67.60% |
| rs2521643 | GG, AG | AA | broad/narrow | broad | 0.01564 | 38.30% | 97.30% | 85.40% | 79.30% |
| rs2521644 | CC | TT | broad/narrow | broad | 0.00918 | 39.70% | 97.30% | 85.90% | 79.30% |
| rs2530121 | GG | TT | composite/broad | broad | 0.02672 | 36.20% | 96.80% | 85.00% | 75.00% |
| rs2530123 | GG | TT | composite/broad | broad | 0.02099 | 40.40% | 96.70% | 85.90% | 76.70% |
| rs2685484 | CC, CT | TT | broad/narrow | broad | 0.00334 | 41.70% | 96.80% | 85.90% | 78.10% |
| rs2722396 | TT | CC | broad/narrow | broad | 0.06130 | 33.90% | 97.30% | 84.80% | 76.90% |
| rs2722398 | TT, CT | CC | broad/narrow | broad | 0.01847 | 38.30% | 97.30% | 85.40% | 79.30% |
| rs28861531 | GG | CC, CG | composite | broad | 0.80326 | 32.20% | 96.80% | 84.30% | 73.10% |
| rs2895215 | TT, CT | CC | broad/narrow | broad | 0.06951 | 37.90% | 97.60% | 85.20% | 81.50% |
| rs2937395 | CC | TT, CT | broad/narrow | broad | 0.00775 | 35.60% | 96.80% | 84.80% | 75.00% |
| rs3135391 | GG | AG | broad/narrow | broad | 0.00031 | 44.80% | 95.80% | 86.60% | 74.30% |
| rs35831078 | | TT, CT | broad/narrow/composite | broad | 0.00412 | 42.40% | 96.40% | 86.30% | 75.80% |
| rs3742228 | | GG, AG | composite | broad | 0.42320 | 33.90% | 96.80% | 84.60% | 74.10% |
| rs3778630 | — | — | broad/narrow | broad | 0.04590 | 35.00% | 96.80% | 84.60% | 75.00% |
| rs401618 | — | TT, CT | broad/narrow | broad | 0.00439 | 37.30% | 97.70% | 85.40% | 81.50% |
| rs4148871 | GG | AG | narrow | broad | 0.32856 | 31.00% | 97.20% | 83.70% | 75.00% |
| rs4255033 | AA, AG | GG | narrow | broad | 0.16036 | 35.60% | 96.80% | 84.60% | 75.00% |
| rs4281882 | CC | AA | broad/narrow/composite | broad | 0.00315 | 36.80% | 97.20% | 85.10% | 77.80% |
| rs4289164 | GG | AA | broad/narrow/composite | broad | 0.00467 | 39.00% | 96.70% | 85.00% | 76.70% |
| rs4306478 | AA | AC, CC | composite/broad | broad | 0.08034 | 37.30% | 97.20% | 85.00% | 78.60% |
| rs4343256 | AA | AG, GG | composite/broad | broad | 0.06024 | 35.60% | 97.30% | 84.90% | 77.80% |
| rs4344916 | AA | CC | broad/narrow/composite | broad | 0.00375 | 40.00% | 97.30% | 85.70% | 80.00% |
| rs4369324 | TT | GG, GT | broad/narrow | broad | 0.00588 | 40.70% | 96.80% | 85.70% | 77.40% |
| rs4435429 | AA | AG | broad/narrow/composite | broad | 0.00412 | 36.80% | 97.30% | 85.60% | 77.80% |
| rs4445746 | GG | AA, AG | broad/narrow/composite | broad | 0.00687 | 37.90% | 96.80% | 85.50% | 75.90% |
| rs4466940 | CC | TT, CT | broad/narrow/composite | broad | 0.01163 | 39.00% | 96.20% | 85.10% | 74.20% |
| rs4468448 | CC | TT, CT | broad | broad | 0.08451 | 37.30% | 96.80% | 85.10% | 75.90% |
| rs4483642 | TT | CT | composite | broad | 0.71368 | 33.90% | 96.80% | 84.60% | 74.10% |
| rs4565951 | TT | CT | composite | broad | 0.67826 | 36.70% | 96.30% | 84.70% | 73.30% |
| rs4578835 | AA | GG | broad/narrow/composite | broad | 0.00489 | 37.90% | 96.80% | 85.40% | 75.90% |
| rs4634524 | CC, CT | TT | narrow | broad | 0.23175 | 47.10% | 96.80% | 87.00% | 80.00% |
| rs4799760 | CC, CT | — | composite | broad | 0.30448 | 32.20% | 96.80% | 84.20% | 73.10% |
| rs4809955 | AA | GG, AG | broad/narrow | broad | 0.00180 | 41.40% | 96.30% | 86.10% | 75.00% |
| rs4811492 | TT | AA | broad/narrow | broad | 0.03358 | 40.40% | 97.20% | 86.00% | 79.30% |
| rs496486 | AA | CC, AC | broad/narrow | broad | 0.00754 | 35.60% | 96.80% | 84.90% | 75.00% |
| rs552994 | TT | CC, CT | broad/narrow | broad | 0.00597 | 37.30% | 96.80% | 85.20% | 75.90% |
| rs6015147 | AA | CC | composite | broad | 0.31168 | 37.90% | 96.30% | 85.20% | 73.30% |

TABLE 16a-continued

Broad Phenotype

| SNP ID | R Allele | NR Allele | analysis according to phenotype: | response definition | P-value | specificity | sensitivity | positive predicting value | negative predicting value |
|---|---|---|---|---|---|---|---|---|---|
| rs6025923 | TT | CC | composite | broad | 0.47714 | 26.50% | 96.60% | 84.80% | 65.00% |
| rs6025927 | TT | CC | composite | broad | 0.16216 | 32.70% | 96.60% | 84.30% | 72.00% |
| rs6091820 | CC | TT, CT | broad/narrow | broad | 0.00357 | 44.80% | 97.30% | 87.00% | 81.30% |
| rs6097782 | CC | TT, CT | broad/narrow | broad | 0.00164 | 42.40% | 97.30% | 86.50% | 80.60% |
| rs6097790 | AA | CC, AC | broad/narrow | broad | 0.00252 | 42.40% | 96.30% | 86.10% | 75.80% |
| rs6097793 | CC, AC | AA | broad/narrow | broad | 0.00265 | 42.40% | 95.90% | 86.00% | 73.50% |
| rs6097797 | TT, CT | CC | broad/narrow | broad | 0.00354 | 42.10% | 95.80% | 86.30% | 72.70% |
| rs6097801 | GG, AG | AA | broad/narrow | broad | 0.00086 | 45.00% | 95.90% | 86.60% | 75.00% |
| rs6123749 | CC | GG | composite | broad | 0.19902 | 35.60% | 96.30% | 84.60% | 72.40% |
| rs6543934 | GG | TT | broad/narrow/composite | broad | 0.00389 | 39.00% | 96.80% | 85.40% | 76.70% |
| rs6558102 | AA | GG | composite | broad | 0.85966 | 31.00% | 96.30% | 84.00% | 69.20% |
| rs656975 | GG | CC, CG | broad/narrow | broad | 0.00805 | 35.60% | 96.80% | 84.90% | 75.00% |
| rs657302 | TT | CC, CT | broad/narrow | broad | 0.01109 | 32.80% | 96.80% | 84.30% | 73.10% |
| rs6584894 | AA, AG | GG | broad/narrow | broad | 0.00822 | 40.00% | 97.00% | 85.70% | 78.60% |
| rs660075 | CC | TT, CT | broad/narrow | broad | 0.00805 | 35.60% | 96.80% | 84.90% | 75.00% |
| rs6713772 | AA | GG, AG | composite | broad | 0.49662 | 30.50% | 97.30% | 83.90% | 75.00% |
| rs6909321 | AA, AG | — | narrow | broad | 0.13191 | 32.20% | 97.30% | 84.30% | 76.00% |
| rs6971202 | GG | — | broad/narrow | broad | 0.06288 | 35.60% | 97.30% | 84.90% | 77.80% |
| rs702355 | AA, AG | | narrow | broad | 0.12523 | 34.50% | 96.80% | 84.60% | 74.10% |
| rs7080507 | CC, CT | — | broad/narrow | broad | 0.01211 | 36.20% | 96.70% | 84.90% | 75.00% |
| rs7086707 | AA, AC | — | broad/narrow | broad | 0.00572 | 39.00% | 96.80% | 85.40% | 76.70% |
| rs7093143 | GG, GT | — | broad/narrow | broad | 0.00990 | 35.60% | 96.80% | 84.70% | 75.00% |
| rs7178587 | — | CC | broad/narrow/composite | broad | 0.00158 | 33.90% | 97.20% | 84.80% | 76.00% |
| rs7180867 | AA, AC | — | broad | broad | 0.09670 | 34.50% | 96.30% | 84.70% | 71.40% |
| rs7232734 | TT | CC, CT | composite | broad | 0.77696 | 32.20% | 96.40% | 84.10% | 70.40% |
| rs7238006 | CT | CC | composite | broad | 0.98175 | 28.60% | 96.80% | 84.10% | 69.60% |
| rs7244801 | GG | AA, AG | composite | broad | 0.74039 | 33.30% | 96.40% | 84.80% | 70.40% |
| rs7317000 | AA | CC, AC | composite/broad | broad | 0.01775 | 41.40% | 96.70% | 85.80% | 77.40% |
| rs751370 | — | CC | broad/narrow/composite | broad | 0.00182 | 37.90% | 96.80% | 85.40% | 75.90% |
| rs752979 | GG | — | broad/narrow | broad | 0.00011 | 39.00% | 94.60% | 85.40% | 65.70% |
| rs7619350 | GG | AA, AG | broad/narrow/composite | broad | 0.03076 | 39.70% | 97.20% | 85.80% | 79.30% |
| rs7633210 | TT | — | broad/narrow | broad | 0.07574 | 35.70% | 97.60% | 85.10% | 80.00% |
| rs7714122 | TT | CC, CT | composite | broad | 0.46907 | 32.80% | 96.80% | 84.50% | 73.10% |
| rs7789703 | CC, CT | TT | narrow | broad | 0.17605 | 33.90% | 97.70% | 85.00% | 79.20% |
| rs7803164 | TT, CT | CC | broad/narrow | broad | 0.04543 | 38.60% | 97.20% | 85.80% | 78.60% |
| rs7806265 | TT, AT | AA | broad/narrow | broad | 0.05396 | 35.60% | 97.20% | 84.80% | 77.80% |
| rs7916897 | TT | GG | narrow | broad | 0.60788 | 48.10% | 97.40% | 87.60% | 83.30% |
| rs7955917 | GG | AA, AG | composite | broad | 0.10317 | 37.30% | 96.80% | 85.30% | 75.90% |
| rs7963693 | CC | GG, CG | composite | broad | 0.13295 | 37.90% | 96.30% | 85.40% | 73.30% |
| rs8099595 | CC | TT, CT | composite | broad | 0.76429 | 31.00% | 96.80% | 84.10% | 72.00% |
| rs8118441 | TT | — | broad/narrow | broad | 0.00186 | 42.40% | 95.90% | 86.10% | 73.50% |
| rs844602 | CC | — | composite | broad | 0.95421 | 38.60% | 97.10% | 85.30% | 78.60% |
| rs844608 | AA, AC | CC | composite | broad | 0.99091 | 36.80% | 97.30% | 85.60% | 77.80% |
| rs844610 | AA, AC | CC | composite | broad | 0.99078 | 37.30% | 97.30% | 85.30% | 78.60% |
| rs844612 | TT, CT | CC | broad/narrow | broad | 0.08601 | 35.60% | 97.20% | 84.80% | 77.80% |
| rs844626 | GG, AG | AA | broad/narrow/composite | broad | 0.06588 | 36.20% | 97.30% | 85.20% | 77.80% |
| rs860722 | CC, CG | — | broad | broad | 0.02761 | 35.60% | 96.40% | 84.80% | 72.40% |
| rs873216 | GG | AA | broad/narrow | broad | 0.00074 | 44.10% | 96.40% | 86.70% | 76.50% |
| rs884266 | CC | TT | composite | broad | 0.51236 | 30.40% | 96.40% | 84.60% | 68.00% |
| rs894857 | GG | AA, AG | composite | broad | 0.93523 | 31.00% | 96.80% | 84.30% | 72.00% |
| rs913882 | CC | TT | composite | broad | 0.14380 | 37.30% | 96.40% | 85.10% | 73.30% |
| rs9315048 | GG | — | broad/narrow | broad | 0.00848 | 35.30% | 98.10% | 86.40% | 81.80% |
| rs9332420 | GG | AA | broad/narrow/composite | broad | 0.00460 | 39.00% | 96.80% | 85.50% | 76.70% |
| rs9933863 | AA | AG | composite | broad | 0.64163 | 37.30% | 96.40% | 85.20% | 73.30% |
| rs9933864 | GG | CG | composite | broad | 0.88068 | 34.50% | 96.80% | 84.60% | 74.10% |
| rs9378319 | TT | CC, CT | broad/narrow/composite | broad | 0.00955 | 39.00% | 96.80% | 85.60% | 76.70% |
| rs9378684 | CC | TT, CT | broad/narrow/composite | broad | 0.00897 | 40.70% | 96.40% | 85.80% | 75.00% |
| rs9392358 | AA | GG, AG | broad/narrow/composite | broad | 0.01177 | 39.70% | 97.30% | 85.90% | 79.30% |
| rs9405541 | CC | TT, CT | broad/narrow/composite | broad | 0.00787 | 41.40% | 96.80% | 86.20% | 77.40% |
| rs9405546 | CC | TT, CT | broad/narrow/composite | broad | 0.00765 | 41.40% | 96.80% | 86.10% | 77.40% |
| rs947603 | CC, CT | TT | broad/narrow | broad | 0.03909 | 33.90% | 96.80% | 84.30% | 74.10% |
| rs948029 | AA | TT | broad/narrow | broad | 0.00007 | 40.70% | 94.50% | 85.60% | 66.70% |
| rs948032 | GG | AA | broad/narrow | broad | 0.00011 | 39.00% | 94.60% | 85.50% | 65.70% |
| rs949298 | GG | — | broad/narrow | broad | 0.02138 | 39.30% | 97.70% | 86.30% | 81.50% |
| rs9508834 | AA | GG, AG | broad/narrow/composite | broad | 0.00409 | 40.70% | 96.40% | 85.90% | 75.00% |
| rs9944913 | CC | TT, CT | composite | broad | 0.99956 | 30.50% | 96.80% | 83.70% | 72.00% |
| rs9952995 | TT | CC, CT | composite | broad | 0.98014 | 29.30% | 96.80% | 83.90% | 70.80% |
| rs998051 | GG | GT | composite | broad | 0.65018 | 32.80% | 96.70% | 84.20% | 73.10% |

TABLE 16b

Narrow and Composite Phenotypes

| SNP ID | response definition | P-value | specificity | sensitivity | positive predicting value | negative predicting value | response definition | P-value | R Square |
|---|---|---|---|---|---|---|---|---|---|
| rs1007328 | narrow | 0.00408 | 67.90% | 71.90% | 69.50% | 70.40% | composite | 0.2050811449 | 0.250 |
| rs10083547 | narrow | 0.10505 | 64.40% | 71.40% | 65.60% | 70.40% | composite | 0.0001776096 | 0.269 |
| rs10136012 | narrow | 0.22150 | 67.80% | 58.90% | 63.50% | 63.50% | composite | 0.0000000122 | 0.293 |
| rs10214633 | narrow | 0.09531 | 60.30% | 68.40% | 62.90% | 66.00% | composite | 0.0016635019 | 0.269 |
| rs10277267 | narrow | 0.01876 | 74.60% | 63.00% | 69.40% | 68.80% | composite | 0.1624935610 | 0.253 |
| rs1040194 | narrow | 0.07052 | 66.10% | 73.20% | 67.20% | 72.20% | composite | 0.8333666744 | 0.246 |
| rs1041897 | narrow | 0.23820 | 63.80% | 61.40% | 62.50% | 62.70% | composite | 0.0000000016 | 0.297 |
| rs10853605 | narrow | 0.00184 | 71.20% | 73.20% | 70.70% | 73.70% | composite | 0.0192031795 | 0.257 |
| rs10931091 | narrow | 0.63575 | 69.50% | 60.00% | 64.70% | 65.10% | composite | 0.0002547344 | 0.267 |
| rs10935015 | narrow | 0.06898 | 61.00% | 71.40% | 63.50% | 69.20% | composite | 0.0348126442 | 0.253 |
| rs10935016 | narrow | 0.05887 | 63.80% | 71.90% | 66.10% | 69.80% | composite | 0.0870671686 | 0.252 |
| rs10935019 | narrow | 0.08402 | 59.30% | 73.20% | 63.10% | 70.00% | composite | 0.0707246889 | 0.253 |
| rs10950359 | narrow | 0.00292 | 76.70% | 67.30% | 72.50% | 71.90% | composite | 0.2165718898 | 0.236 |
| rs10950371 | narrow | 0.00602 | 73.30% | 71.90% | 71.90% | 73.30% | composite | 0.1803959905 | 0.252 |
| rs10988087 | narrow | 0.71678 | 63.80% | 67.90% | 64.40% | 67.30% | composite | 0.0000000031 | 0.305 |
| rs11009827 | narrow | 0.13412 | 63.80% | 69.60% | 65.00% | 68.50% | composite | 0.1112191369 | 0.250 |
| rs11009835 | narrow | 0.17860 | 62.10% | 67.90% | 63.30% | 66.70% | composite | 0.1131736185 | 0.250 |
| rs11081859 | narrow | 0.80646 | 66.10% | 56.40% | 60.80% | 61.90% | composite | 0.0006049647 | 0.266 |
| rs11599624 | narrow | 0.00049 | 77.60% | 70.90% | 75.00% | 73.80% | composite | 0.0695370150 | 0.240 |
| rs11617134 | narrow | 0.11844 | 61.00% | 69.60% | 62.90% | 67.90% | composite | 0.0000183303 | 0.273 |
| rs11618546 | narrow | 0.73048 | 65.00% | 59.60% | 61.80% | 62.90% | composite | 0.0000000276 | 0.290 |
| rs11694344 | narrow | 0.07036 | 72.90% | 67.90% | 70.40% | 70.50% | composite | 0.0676961332 | 0.251 |
| rs11709339 | narrow | 0.06063 | 60.30% | 71.40% | 63.50% | 68.60% | composite | 0.0748133928 | 0.252 |
| rs11719825 | narrow | 0.05582 | 61.40% | 75.50% | 64.50% | 72.90% | composite | 0.0278392113 | 0.257 |
| rs11761457 | narrow | 0.01490 | 69.50% | 71.40% | 69.00% | 71.90% | composite | 0.2595068530 | 0.250 |
| rs11907046 | narrow | 0.01512 | 61.70% | 71.90% | 64.10% | 69.80% | composite | 0.6134026928 | 0.246 |
| rs12055694 | narrow | 0.05185 | 64.40% | 70.90% | 65.00% | 70.40% | composite | 0.0006868573 | 0.276 |
| rs12256889 | narrow | 0.00223 | 71.20% | 70.20% | 70.20% | 71.20% | composite | 0.0048849245 | 0.261 |
| rs1229542 | narrow | 0.22302 | 60.30% | 70.20% | 63.50% | 67.30% | composite | 0.3948082568 | 0.256 |
| rs1229553 | narrow | 0.14140 | 60.00% | 66.70% | 61.30% | 65.50% | composite | 0.0011542566 | 0.264 |
| rs1229555 | narrow | 0.14151 | 62.10% | 66.70% | 63.30% | 65.50% | composite | 0.0006891767 | 0.270 |
| rs1229558 | narrow | 0.35801 | 60.70% | 69.60% | 63.90% | 66.70% | composite | 0.0004112907 | 0.276 |
| rs1229562 | narrow | 0.10238 | 61.00% | 71.40% | 63.50% | 69.20% | composite | 0.0013755214 | 0.263 |
| rs1229563 | narrow | 0.14702 | 61.00% | 69.60% | 62.90% | 67.90% | composite | 0.0016266164 | 0.266 |
| rs1229564 | narrow | 0.10238 | 61.00% | 71.40% | 63.50% | 69.20% | composite | 0.0011739273 | 0.263 |
| rs1229568 | narrow | 0.11245 | 62.70% | 69.10% | 63.30% | 68.50% | composite | 0.0015575098 | 0.262 |
| rs12340584 | narrow | 0.70311 | 63.30% | 53.60% | 57.70% | 59.40% | composite | 0.0000498360 | 0.271 |
| rs1234567 | narrow | 0.14140 | 60.00% | 66.70% | 61.30% | 65.50% | composite | 0.0014524348 | 0.262 |
| rs1234947 | narrow | 0.14140 | 60.00% | 66.70% | 61.30% | 65.50% | composite | 0.0013208828 | 0.262 |
| rs1237625 | narrow | 0.10238 | 61.00% | 71.40% | 63.50% | 69.20% | composite | 0.0010132650 | 0.263 |
| rs12488259 | narrow | 0.05733 | 59.30% | 75.00% | 63.60% | 71.40% | composite | 0.0677945040 | 0.263 |
| rs12494606 | narrow | 0.08402 | 59.30% | 73.20% | 63.10% | 70.00% | composite | 0.0649695076 | 0.251 |
| rs12496278 | narrow | 0.05483 | 63.30% | 71.40% | 64.50% | 70.40% | composite | 0.0901845657 | 0.252 |
| rs12524041 | narrow | 0.00842 | 71.20% | 64.30% | 67.90% | 67.70% | composite | 0.3664238633 | 0.247 |
| rs12529764 | narrow | 0.01003 | 72.40% | 66.10% | 69.80% | 68.90% | composite | 0.1210653349 | 0.250 |
| rs12532459 | narrow | 0.02232 | 78.00% | 69.60% | 75.00% | 73.00% | composite | 0.3350822048 | 0.254 |
| rs12540494 | narrow | 0.01891 | 78.00% | 70.90% | 75.00% | 74.20% | composite | 0.1669469791 | 0.257 |
| rs12593600 | narrow | 0.09698 | 58.60% | 71.40% | 62.50% | 68.00% | composite | 0.0001262140 | 0.270 |
| rs12633010 | narrow | 0.05946 | 61.40% | 73.70% | 65.60% | 70.00% | composite | 0.1145268012 | 0.261 |
| rs12637073 | narrow | 0.05223 | 63.30% | 71.90% | 65.10% | 70.40% | composite | 0.0967951660 | 0.252 |
| rs12639443 | narrow | 0.01681 | 66.10% | 71.90% | 67.20% | 70.90% | composite | 0.0664176972 | 0.252 |
| rs1264423 | narrow | 0.02012 | 71.20% | 62.50% | 67.30% | 66.70% | composite | 0.1631840283 | 0.249 |
| rs1282540 | narrow | 0.07052 | 66.70% | 73.20% | 68.30% | 71.70% | composite | 0.6472043851 | 0.248 |
| rs1282546 | narrow | 0.07052 | 66.10% | 73.20% | 67.20% | 72.20% | composite | 0.7524765779 | 0.245 |
| rs12968586 | narrow | 0.94218 | 63.30% | 58.90% | 60.00% | 62.30% | composite | 0.0004984226 | 0.265 |
| rs1299325 | narrow | 0.07052 | 66.10% | 73.20% | 67.20% | 72.20% | composite | 0.6954314594 | 0.247 |
| rs13021482 | narrow | 0.21323 | 67.30% | 64.60% | 64.60% | 67.30% | composite | 0.1249466723 | 0.270 |
| rs13042992 | narrow | 0.60485 | 63.80% | 65.50% | 63.20% | 66.10% | composite | 0.0000481220 | 0.271 |
| rs13320648 | narrow | 0.00068 | 63.80% | 76.80% | 67.20% | 74.00% | composite | 0.7343494667 | 0.248 |
| rs13238613 | narrow | 0.00756 | 74.60% | 71.40% | 72.70% | 73.30% | composite | 0.1828487368 | 0.251 |
| rs13245980 | narrow | 0.02028 | 79.70% | 64.80% | 74.50% | 71.20% | composite | 0.3356975007 | 0.254 |
| rs1415557 | narrow | 0.01107 | 74.60% | 69.60% | 72.20% | 72.10% | composite | 0.9001338769 | 0.246 |
| rs1538123 | narrow | 0.00308 | 76.30% | 69.60% | 73.60% | 72.60% | composite | 0.9139002586 | 0.245 |
| rs1573706 | narrow | 0.01127 | 71.20% | 73.20% | 70.70% | 73.70% | composite | 0.0013465086 | 0.262 |
| rs1591661 | narrow | 0.00222 | 76.30% | 69.60% | 73.60% | 72.60% | composite | 0.8782253468 | 0.252 |
| rs1611185 | narrow | 0.01980 | 66.70% | 69.60% | 68.40% | 67.90% | composite | 0.0722742172 | 0.181 |
| rs1683691 | narrow | 0.43495 | 61.00% | 66.10% | 61.70% | 65.50% | composite | 0.0019111927 | 0.263 |
| rs16999008 | narrow | 0.01200 | 62.70% | 73.70% | 65.60% | 71.20% | composite | 0.6105720761 | 0.246 |
| rs17007730 | narrow | 0.58028 | 63.80% | 60.00% | 61.10% | 62.70% | composite | 0.0000223406 | 0.272 |
| rs17087180 | narrow | 0.18731 | 63.20% | 69.60% | 65.00% | 67.90% | composite | 0.0000000001 | 0.304 |
| rs17104665 | narrow | 0.86999 | 63.80% | 58.20% | 60.40% | 61.70% | composite | 0.0000160623 | 0.276 |

TABLE 16b-continued

Narrow and Composite Phenotypes

| SNP ID | response definition | P-value | specificity | sensitivity | positive predicting value | negative predicting value | response definition | P-value | R Square |
|---|---|---|---|---|---|---|---|---|---|
| rs17104742 | narrow | 0.86754 | 64.90% | 64.30% | 64.30% | 64.90% | composite | 0.0000104133 | 0.281 |
| rs17134651 | narrow | 0.05573 | 62.70% | 71.40% | 64.50% | 69.80% | composite | 0.0008626073 | 0.265 |
| rs17575455 | narrow | 0.10819 | 67.80% | 67.90% | 66.70% | 69.00% | composite | 0.0000053597 | 0.277 |
| rs17588454 | narrow | 0.07799 | 62.70% | 73.20% | 65.10% | 71.20% | composite | 0.0000204321 | 0.274 |
| rs17666347 | narrow | 0.97881 | 69.50% | 56.40% | 63.30% | 63.10% | composite | 0.0000458865 | 0.271 |
| rs17771939 | narrow | 0.00387 | 67.80% | 73.20% | 68.30% | 72.70% | composite | 0.8848357851 | 0.248 |
| rs17807327 | narrow | 0.00749 | 76.30% | 61.80% | 70.80% | 68.20% | composite | 0.4731278635 | 0.248 |
| rs17807445 | narrow | 0.02258 | 71.70% | 62.50% | 67.30% | 67.20% | composite | 0.1064680457 | 0.251 |
| rs1886308 | narrow | 0.01502 | 61.70% | 68.40% | 62.90% | 67.30% | composite | 0.5133224539 | 0.247 |
| rs1892974 | narrow | 0.00024 | 69.50% | 77.20% | 71.00% | 75.90% | composite | 0.6406540443 | 0.248 |
| rs1941973 | narrow | 0.49180 | 60.00% | 60.70% | 58.60% | 62.10% | composite | 0.0000547438 | 0.271 |
| rs2033471 | narrow | 0.84659 | 62.70% | 61.40% | 61.40% | 62.70% | composite | 0.0000256482 | 0.273 |
| rs2088713 | narrow | 0.04883 | 63.20% | 69.80% | 63.80% | 69.20% | composite | 0.0893788014 | 0.243 |
| rs214526 | narrow | 0.02901 | 69.00% | 64.30% | 66.70% | 66.70% | composite | 0.3079668681 | 0.248 |
| rs2155262 | narrow | 0.00031 | 67.80% | 78.60% | 69.80% | 76.90% | composite | 0.5761110166 | 0.251 |
| rs2177073 | narrow | 0.98321 | 66.70% | 64.90% | 64.90% | 66.70% | composite | 0.0000025098 | 0.278 |
| rs2187495 | narrow | 0.00015 | 68.30% | 76.80% | 69.40% | 75.90% | composite | 0.6545016897 | 0.248 |
| rs2277431 | narrow | 0.44554 | 65.00% | 56.40% | 59.60% | 61.90% | composite | 0.0000450193 | 0.272 |
| rs2305623 | narrow | 0.07317 | 59.30% | 72.70% | 62.50% | 70.00% | composite | 0.1998120292 | 0.250 |
| rs2374730 | narrow | 0.16022 | 63.30% | 59.60% | 60.70% | 62.30% | composite | 0.0000019327 | 0.279 |
| rs2461319 | narrow | 0.09884 | 72.90% | 66.10% | 69.80% | 69.40% | composite | 0.9302610439 | 0.245 |
| rs2487889 | narrow | 0.02308 | 61.00% | 66.10% | 61.70% | 65.50% | composite | 0.4149154853 | 0.247 |
| rs2487896 | narrow | 0.04167 | 63.30% | 68.40% | 63.90% | 67.90% | composite | 0.4363548670 | 0.247 |
| rs2508806 | narrow | 0.00301 | 65.50% | 76.80% | 69.40% | 73.50% | composite | 0.6790301896 | 0.245 |
| rs2511064 | narrow | 0.00577 | 66.10% | 76.80% | 68.30% | 75.00% | composite | 0.6854191571 | 0.247 |
| rs2521643 | narrow | 0.00682 | 73.30% | 66.70% | 70.40% | 69.80% | composite | 0.8397645047 | 0.258 |
| rs2521644 | narrow | 0.00303 | 77.60% | 63.20% | 73.50% | 68.20% | composite | 0.7274741771 | 0.252 |
| rs2530121 | narrow | 0.19485 | 60.30% | 66.70% | 62.30% | 64.80% | composite | 0.0157723654 | 0.256 |
| rs2530123 | narrow | 0.12073 | 59.60% | 69.10% | 62.30% | 66.70% | composite | 0.0169136879 | 0.188 |
| rs2685484 | narrow | 0.00273 | 76.70% | 70.90% | 73.60% | 74.20% | composite | 0.8157058663 | 0.245 |
| rs2722396 | narrow | 0.00818 | 72.90% | 61.40% | 68.60% | 66.20% | composite | 0.6811200337 | 0.247 |
| rs2722398 | narrow | 0.00682 | 73.30% | 66.70% | 70.40% | 69.80% | composite | 0.7767461226 | 0.246 |
| rs28861531 | narrow | 0.95650 | 61.00% | 58.90% | 58.90% | 61.00% | composite | 0.0000000623 | 0.293 |
| rs2895215 | narrow | 0.01525 | 74.10% | 70.40% | 71.70% | 72.90% | composite | 0.1030119635 | 0.252 |
| rs2937395 | narrow | 0.07058 | 66.10% | 73.20% | 67.20% | 72.20% | composite | 0.7574277637 | 0.245 |
| rs3135391 | narrow | 0.00362 | 67.20% | 72.70% | 67.80% | 72.20% | composite | 0.7886848031 | 0.248 |
| rs35831078 | narrow | 0.04785 | 62.70% | 75.40% | 66.20% | 72.50% | composite | 0.0000393384 | 0.277 |
| rs3742228 | narrow | 0.93310 | 59.30% | 57.90% | 57.90% | 59.30% | composite | 0.0000001929 | 0.285 |
| rs3778630 | narrow | 0.08732 | 70.00% | 58.90% | 64.30% | 64.60% | composite | 0.1201100770 | 0.248 |
| rs401618 | narrow | 0.01912 | 66.10% | 64.90% | 64.90% | 66.10% | composite | 0.2527657227 | 0.255 |
| rs4148871 | narrow | 0.00638 | 62.10% | 76.80% | 66.20% | 73.50% | composite | 0.2213169699 | 0.254 |
| rs4255033 | narrow | 0.02413 | 78.00% | 66.10% | 74.00% | 70.80% | composite | 0.2641530455 | 0.248 |
| rs4281882 | narrow | 0.02853 | 70.20% | 70.90% | 69.60% | 71.40% | composite | 0.0055073684 | 0.260 |
| rs4289164 | narrow | 0.05358 | 72.90% | 67.90% | 70.40% | 70.50% | composite | 0.0284597023 | 0.262 |
| rs4306478 | narrow | 0.32247 | 67.80% | 67.30% | 66.10% | 69.00% | composite | 0.0001910761 | 0.270 |
| rs4343256 | narrow | 0.18768 | 62.70% | 66.10% | 62.70% | 66.10% | composite | 0.0001403301 | 0.268 |
| rs4344916 | narrow | 0.04203 | 75.00% | 67.90% | 71.70% | 71.40% | composite | 0.0109294485 | 0.257 |
| rs4369324 | narrow | 0.00308 | 76.30% | 69.60% | 73.60% | 72.60% | composite | 0.9220257544 | 0.247 |
| rs4435429 | narrow | 0.02361 | 71.90% | 71.90% | 71.90% | 71.90% | composite | 0.0049301543 | 0.245 |
| rs4445746 | narrow | 0.00937 | 63.80% | 80.40% | 68.20% | 77.10% | composite | 0.0853642663 | 0.252 |
| rs4466940 | narrow | 0.02967 | 64.40% | 75.00% | 66.70% | 73.10% | composite | 0.0124998039 | 0.259 |
| rs4468448 | narrow | 0.11642 | 62.70% | 73.20% | 65.10% | 71.20% | composite | 0.1384180377 | 0.250 |
| rs4483642 | narrow | 0.29453 | 62.70% | 59.60% | 60.70% | 61.70% | composite | 0.0000146605 | 0.280 |
| rs4565951 | narrow | 0.48217 | 65.00% | 57.10% | 60.40% | 61.90% | composite | 0.0001718130 | 0.256 |
| rs4578835 | narrow | 0.04990 | 72.40% | 67.90% | 70.40% | 70.00% | composite | 0.0116559644 | 0.262 |
| rs4634524 | narrow | 0.03289 | 80.40% | 68.90% | 75.60% | 74.50% | composite | 0.3275992309 | 0.265 |
| rs4799760 | narrow | 0.72214 | 64.40% | 64.30% | 63.20% | 65.50% | composite | 0.0003882703 | 0.265 |
| rs4809955 | narrow | 0.01531 | 60.30% | 71.40% | 63.50% | 68.60% | composite | 0.6111078532 | 0.175 |
| rs4811492 | narrow | 0.03685 | 64.90% | 75.00% | 67.70% | 72.50% | composite | 0.4190188183 | 0.251 |
| rs496486 | narrow | 0.07058 | 66.10% | 73.20% | 67.20% | 72.20% | composite | 0.7537962256 | 0.246 |
| rs552994 | narrow | 0.07052 | 66.10% | 73.20% | 67.20% | 72.20% | composite | 0.7714754149 | 0.246 |
| rs6015147 | narrow | 0.95445 | 69.00% | 63.00% | 65.40% | 66.70% | composite | 0.0000005811 | 0.222 |
| rs6025923 | narrow | 0.74123 | 61.20% | 66.70% | 65.50% | 62.50% | composite | 0.0000238011 | 0.277 |
| rs6025927 | narrow | 0.99741 | 63.60% | 66.70% | 64.30% | 66.00% | composite | 0.0001156133 | 0.176 |
| rs6091820 | narrow | 0.03230 | 60.30% | 71.90% | 64.10% | 68.60% | composite | 0.7102878021 | 0.248 |
| rs6097782 | narrow | 0.01874 | 61.00% | 71.90% | 64.10% | 69.20% | composite | 0.6232805036 | 0.246 |
| rs6097790 | narrow | 0.02179 | 62.70% | 69.60% | 63.90% | 68.50% | composite | 0.5460615394 | 0.246 |
| rs6097793 | narrow | 0.02179 | 62.70% | 69.60% | 63.90% | 68.50% | composite | 0.5534389737 | 0.246 |
| rs6097797 | narrow | 0.01685 | 63.20% | 71.40% | 65.60% | 69.20% | composite | 0.6656843066 | 0.251 |
| rs6097801 | narrow | 0.01512 | 61.70% | 71.90% | 64.10% | 69.80% | composite | 0.7551179553 | 0.247 |
| rs6123749 | narrow | 0.90554 | 66.10% | 64.30% | 64.30% | 66.10% | composite | 0.0000013456 | 0.280 |

TABLE 16b-continued

Narrow and Composite Phenotypes

| SNP ID | response definition | P-value | specificity | sensitivity | positive predicting value | negative predicting value | response definition | P-value | R Square |
|---|---|---|---|---|---|---|---|---|---|
| rs6543934 | narrow | 0.06219 | 72.90% | 65.50% | 69.20% | 69.40% | composite | 0.0600136502 | 0.253 |
| rs6558102 | narrow | 0.64731 | 63.80% | 67.90% | 64.40% | 67.30% | composite | 0.0000008558 | 0.283 |
| rs656975 | narrow | 0.07052 | 66.10% | 73.20% | 67.20% | 72.20% | composite | 0.7480314538 | 0.246 |
| rs657302 | narrow | 0.08729 | 67.20% | 74.50% | 68.30% | 73.60% | composite | 0.7230354724 | 0.246 |
| rs6584894 | narrow | 0.01294 | 78.20% | 67.30% | 73.30% | 72.90% | composite | 0.6868242683 | 0.232 |
| rs660075 | narrow | 0.07058 | 66.10% | 73.20% | 67.20% | 72.20% | composite | 0.7494347642 | 0.246 |
| rs6713772 | narrow | 0.71395 | 62.70% | 60.70% | 60.70% | 62.70% | composite | 0.0000002337 | 0.284 |
| rs6909321 | narrow | 0.06543 | 71.20% | 62.50% | 67.30% | 66.70% | composite | 0.1096157565 | 0.251 |
| rs6971202 | narrow | 0.00663 | 76.30% | 61.80% | 70.80% | 68.20% | composite | 0.6839825085 | 0.246 |
| rs702355 | narrow | 0.06082 | 75.90% | 60.00% | 70.20% | 66.70% | composite | 0.1579609518 | 0.250 |
| rs7080507 | narrow | 0.00600 | 75.90% | 73.20% | 74.50% | 74.60% | composite | 0.8019114252 | 0.247 |
| rs7086707 | narrow | 0.00500 | 74.60% | 69.60% | 72.20% | 72.10% | composite | 0.9233502939 | 0.246 |
| rs7093143 | narrow | 0.00961 | 74.60% | 68.50% | 71.20% | 72.10% | composite | 0.8860702002 | 0.246 |
| rs7178587 | narrow | 0.03385 | 62.50% | 67.30% | 63.80% | 66.00% | composite | 0.0678997453 | 0.242 |
| rs7180867 | narrow | 0.16354 | 65.50% | 66.10% | 64.90% | 66.70% | composite | 0.1819945701 | 0.254 |
| rs7232734 | narrow | 0.90058 | 66.10% | 58.90% | 62.30% | 62.90% | composite | 0.0002842721 | 0.272 |
| rs7238006 | narrow | 0.52288 | 67.90% | 66.10% | 67.30% | 66.70% | composite | 0.0079837106 | 0.257 |
| rs7244801 | narrow | 0.84726 | 61.40% | 69.60% | 63.90% | 67.30% | composite | 0.0002560514 | 0.273 |
| rs7317000 | narrow | 0.21018 | 56.90% | 71.90% | 62.10% | 67.30% | composite | 0.0001141326 | 0.269 |
| rs751370 | narrow | 0.00859 | 67.20% | 70.40% | 66.70% | 70.90% | composite | 0.0185234836 | 0.265 |
| rs752979 | narrow | 0.00046 | 64.40% | 77.20% | 67.70% | 74.50% | composite | 0.7360004970 | 0.252 |
| rs7619350 | narrow | 0.06063 | 60.30% | 71.40% | 63.50% | 68.60% | composite | 0.0851490259 | 0.251 |
| rs7633210 | narrow | 0.05618 | 67.90% | 71.70% | 67.90% | 71.70% | composite | 0.5617924237 | 0.260 |
| rs7714122 | narrow | 0.20804 | 65.50% | 67.30% | 64.90% | 67.90% | composite | 0.0027785239 | 0.279 |
| rs7789703 | narrow | 0.07183 | 66.10% | 65.40% | 64.20% | 67.30% | composite | 0.3143051576 | 0.247 |
| rs7803164 | narrow | 0.01264 | 71.90% | 69.60% | 70.90% | 70.70% | composite | 0.2698212215 | 0.254 |
| rs7806265 | narrow | 0.00718 | 74.60% | 71.90% | 73.20% | 73.30% | composite | 0.1586648076 | 0.184 |
| rs7916897 | narrow | 0.05231 | 76.90% | 76.00% | 76.00% | 76.90% | composite | 0.1481399148 | 0.261 |
| rs7955917 | narrow | 0.29246 | 55.90% | 66.10% | 58.70% | 63.50% | composite | 0.0002623828 | 0.270 |
| rs7963693 | narrow | 0.39632 | 55.20% | 66.70% | 59.40% | 62.70% | composite | 0.0001330852 | 0.275 |
| rs8099595 | narrow | 0.90747 | 63.80% | 62.50% | 62.50% | 63.80% | composite | 0.0003997105 | 0.265 |
| rs8118441 | narrow | 0.02179 | 62.70% | 69.60% | 63.90% | 68.50% | composite | 0.5282969814 | 0.246 |
| rs844602 | narrow | 0.96474 | 75.40% | 59.30% | 69.60% | 66.20% | composite | 0.0172114588 | 0.260 |
| rs844608 | narrow | 0.99421 | 75.40% | 58.90% | 70.20% | 65.20% | composite | 0.0505344333 | 0.260 |
| rs844610 | narrow | 0.99419 | 74.60% | 59.60% | 69.40% | 65.70% | composite | 0.0385055827 | 0.260 |
| rs844612 | narrow | 0.03225 | 74.60% | 60.00% | 68.80% | 66.70% | composite | 0.1289376035 | 0.251 |
| rs844626 | narrow | 0.02163 | 77.60% | 59.30% | 71.10% | 67.20% | composite | 0.0447630201 | 0.262 |
| rs860722 | narrow | 0.19021 | 67.80% | 69.60% | 67.20% | 70.20% | composite | 0.5902077325 | 0.254 |
| rs873216 | narrow | 0.01102 | 62.70% | 71.90% | 65.10% | 69.80% | composite | 0.5672550674 | 0.253 |
| rs884266 | narrow | 0.97903 | 58.90% | 63.20% | 61.10% | 61.10% | composite | 0.0004725485 | 0.269 |
| rs894857 | narrow | 0.82796 | 62.10% | 66.70% | 63.30% | 65.50% | composite | 0.0000000002 | 0.308 |
| rs913882 | narrow | 0.93461 | 66.10% | 64.30% | 64.30% | 66.10% | composite | 0.0000000055 | 0.294 |
| rs9315048 | narrow | 0.00172 | 64.70% | 82.10% | 71.90% | 76.70% | composite | 0.3705256604 | 0.233 |
| rs9332420 | narrow | 0.05980 | 71.20% | 66.10% | 68.50% | 68.90% | composite | 0.0331420821 | 0.255 |
| rs933863 | narrow | 0.26426 | 62.70% | 59.60% | 60.70% | 61.70% | composite | 0.0000047280 | 0.283 |
| rs933864 | narrow | 0.69839 | 62.10% | 64.30% | 62.10% | 64.30% | composite | 0.0956803375 | 0.186 |
| rs9378319 | narrow | 0.05573 | 62.70% | 71.40% | 64.50% | 69.80% | composite | 0.0008169610 | 0.265 |
| rs9378684 | narrow | 0.03293 | 64.40% | 69.60% | 65.00% | 69.10% | composite | 0.0013903659 | 0.262 |
| rs9392358 | narrow | 0.08140 | 62.10% | 72.70% | 64.50% | 70.60% | composite | 0.0006766609 | 0.265 |
| rs9405541 | narrow | 0.04542 | 65.50% | 71.40% | 66.70% | 70.40% | composite | 0.0003778692 | 0.271 |
| rs9405546 | narrow | 0.05023 | 65.50% | 70.90% | 66.10% | 70.40% | composite | 0.0003198511 | 0.272 |
| rs947603 | narrow | 0.00687 | 74.60% | 69.60% | 72.20% | 72.10% | composite | 0.2358314299 | 0.255 |
| rs948029 | narrow | 0.00046 | 64.40% | 77.20% | 67.70% | 74.50% | composite | 0.7136661558 | 0.252 |
| rs948032 | narrow | 0.00046 | 64.40% | 77.20% | 67.70% | 74.50% | composite | 0.7162224264 | 0.254 |
| rs949298 | narrow | 0.01576 | 62.50% | 78.90% | 68.20% | 74.50% | composite | 0.6959498100 | 0.252 |
| rs9508834 | narrow | 0.00833 | 66.10% | 76.80% | 68.30% | 75.00% | composite | 0.0072643808 | 0.280 |
| rs9944913 | narrow | 0.86061 | 69.50% | 60.70% | 65.40% | 65.10% | composite | 0.0000151282 | 0.284 |
| rs9952995 | narrow | 0.77141 | 65.50% | 69.60% | 66.10% | 69.10% | composite | 0.0001815576 | 0.273 |
| rs998051 | narrow | 0.65765 | 65.50% | 61.80% | 63.00% | 64.40% | composite | 0.0000059311 | 0.283 |

Prediction Models Using GWAS Significant SNPs and Tagged SNPs

Additional models were established based on 30 SNPs that were chosen out of the 201 SNPs listed in table 16, based on having low p-values. The 30 SNPs chosen were rs947603, rs1007328, rs1573706, rs2177073, rs2487896, rs2511064, rs2521644, rs3135391, rs4148871, rs4343256, rs4344916, rs4369324, rs4445746, rs6097801, rs9508834, rs9944913, rs10853605, rs10931091, rs10950359, rs10988087, rs11599624, rs11617134, rs12256889, rs12639443, rs13042992, rs13238613, rs17087180, rs17575455, rs17771939 and rs17807327.

A pool of model candidates was generated based on combinatorial optimization heuristics. Selected models were chosen based on low value of Akaike's Information Criterion (AIC) and low number of SNPs. The model chosen in the previous step went through "Leave one out" cross validation—searching for high values of the Area Under the ROC curve.

TABLE 17

| Model | SNPs in model |
|---|---|
| GM1003 | rs11599624 rs12639443 rs13042992 rs13238613 rs17087180 rs17771939 rs17807327 rs2487896 rs3135391 rs4148871 rs4343256 rs4344916 rs9508834 |
| GM1006 | rs12256889 rs12639443 rs13238613 rs1573706 rs17087180 rs17771939 rs17807327 rs2487896 rs4343256 rs4344916 rs4369324 rs4445746 rs9944913 |
| GM1011 | rs10988087 rs12639443 rs13042992 rs13238613 rs1573706 rs17087180 rs17771939 rs17807327 rs4148871 rs4344916 rs6097801 rs9508834 |
| GM1012 | rs10988087 rs12256889 rs12639443 rs17087180 rs17771939 rs2177073 rs2521644 rs4344916 rs4369324 rs6097801 rs9508834 rs9944913 |
| GM2004 | rs10988087 rs11617134 rs12639443 rs13042992 rs17087180 rs17771939 rs17807327 rs2487896 rs4148871 rs4344916 rs4445746 rs6097801 rs9508834 |
| GM2014 | rs10988087 rs11617134 rs12639443 rs13042992 rs17087180 rs17771939 rs17807327 rs2487896 rs2521644 rs4148871 rs4344916 rs4445746 rs6097801 |
| GM2022 | rs10988087 rs12256889 rs12639443 rs17087180 rs17771939 rs17807327 rs2487896 rs4148871 rs4344916 rs6097801 rs9508834 |
| GM2027 | rs1007328 rs11617134 rs12639443 rs13238613 rs1573706 rs17087180 rs17771939 rs17807327 rs4343256 rs4344916 rs9508834 rs9944913 |
| GM2043 | rs12639443 rs17087180 rs17771939 rs17807327 rs2487896 rs4148871 rs4343256 rs4344916 rs4369324 rs4445746 rs6097801 rs9508834 rs9944913 |
| GM2068 | rs11617134 rs12639443 rs17087180 rs17771939 rs17807327 rs2487896 rs3135391 rs4148871 rs4344916 rs4369324 rs6097801 rs9508834 rs9944913 |
| GM2090 | rs10988087 rs12639443 rs13238613 rs17087180 rs17771939 rs2487896 rs4148871 rs4343256 rs4344916 rs9508834 |
| GM2094 | rs11617134 rs12256889 rs12639443 rs13042992 rs17087180 rs17771939 rs17807327 rs2177073 rs2487896 rs4343256 rs4344916 rs6097801 rs9508834 |
| GM2277 | rs10950359 rs11617134 rs12639443 rs17087180 rs17771939 rs2487896 rs2511064 rs3135391 rs4148871 rs4343256 rs4344916 rs9508834 rs9944913 |
| GM2338 | rs12256889 rs12639443 rs13042992 rs17087180 rs17771939 rs17807327 rs2487896 rs2521644 rs4344916 rs6097801 |
| GM3102 | rs10950359 rs10988087 rs11599624 rs12256889 rs12639443 rs13042992 rs17087180 rs17771939 rs17807327 rs2521644 rs3135391 rs4344916 rs9508834 |
| GM3150 | rs1007328 rs10950359 rs12256889 rs12639443 rs13042992 rs1573706 rs17087180 rs17771939 rs17807327 rs4343256 rs4344916 rs947603 rs9508834 |
| GM3332 | rs11599624 rs12256889 rs12639443 rs1573706 rs17087180 rs17771939 rs17807327 rs2177073 rs2487896 rs4344916 rs6097801 rs9508834 rs9944913 |

The response probability of a specific patient was calculated according to each model. Following the genotyping of the patient at the relevant SNPs, the values of the SNPs were recoded to numeric values as described in the following tables (18a-s)

TABLE 18a

| rs1007328 | Recoded value |
|---|---|
| CC | 0 |
| CT | 1 |
| TT | 2 |

TABLE 18b

| rs10950359 | Recoded value |
|---|---|
| AA | 0 |
| AG | 1 |
| GG | 2 |

TABLE 18c

| rs10988087 | Recoded value |
|---|---|
| AA | 0 |
| AG | 1 |
| GG | 1 |

TABLE 18d

| rs11617134 | Recoded value |
|---|---|
| CC | 0 |
| CT | 1 |
| TT | 2 |

TABLE 18e

| rs1225689 | Recoded value |
|---|---|
| AA | 0 |
| AC | 1 |
| CC | 2 |

TABLE 18f

| rs13042992 | Recoded value |
|---|---|
| TT | 0 |
| GG | 1 |
| GT | 1 |

TABLE 18g

| rs13238613 | Recoded value |
|---|---|
| CC | 0 |
| CT | 1 |
| TT | 2 |

TABLE 18h

| rs17087180 | Recoded value |
|---|---|
| AA | 0 |
| AG | 1 |
| GG | 2 |

TABLE 18i

| rs2177073 | Recoded value |
|---|---|
| CC | 0 |
| AA | 1 |
| AC | 1 |

TABLE 18j

| rs2511064 | Recoded value |
|---|---|
| AA | 0 |
| AG | 1 |
| GG | 2 |

TABLE 18k

| rs2521644 | Recoded value |
|---|---|
| CC | 0 |
| CT | 1 |
| TT | 2 |

TABLE 18l

| rs4343256 | Recoded value |
|---|---|
| AA | 0 |
| AG | 1 |
| GG | 2 |

TABLE 18m

| rs4344916 | Recoded value |
|---|---|
| AA | 0 |
| AC | 1 |
| CC | 2 |

TABLE 18n

| rs4369324 | Recoded value |
|---|---|
| GG | 0 |
| GT | 1 |
| TT | 2 |

TABLE 18o

| rs4445746 | Recoded value |
|---|---|
| AA | 0 |
| AG | 1 |
| GG | 2 |

TABLE 18p

| rs6097801 | Recoded value |
|---|---|
| AA | 0 |
| AG | 1 |
| GG | 2 |

TABLE 18q

| rs947603 | Recoded value |
|---|---|
| CC | 0 |
| CT | 1 |
| TT | 2 |

TABLE 18r

| rs9508834 | Recoded value |
|---|---|
| AA | 0 |
| AG | 1 |
| GG | 2 |

TABLE 18s

| rs9944913 | Recoded value |
|---|---|
| CC | 0 |
| CT | 1 |
| TT | 1 |

For each of the following SNPs define two new numeric variables as described in the following tables (19a-h):

TABLE 19a

| rs11599624 | rs11599624_AA | rs11599624_AG |
|---|---|---|
| AA | 1 | 0 |
| AG | 0 | 1 |
| GG | −1 | −1 |

TABLE 19b

| rs12639443 | rs12639443_CC | rs12639443_CT |
|---|---|---|
| CC | 1 | 0 |
| CT | 0 | 1 |
| TT | −1 | −1 |

TABLE 19c

| rs1573706 | rs1573706__CC | rs1573706__CT |
|---|---|---|
| CC | 1 | 0 |
| CT | 0 | 1 |
| TT | −1 | −1 |

TABLE 19d

| rs17771939 | rs17771939__CC | rs17771939__CT |
|---|---|---|
| CC | 1 | 0 |
| CT | 0 | 1 |
| TT | −1 | −1 |

TABLE 19e

| rs17807327 | rs17807327__AA | rs17807327__AC |
|---|---|---|
| AA | 1 | 0 |
| AC | 0 | 1 |
| CC | −1 | −1 |

TABLE 19f

| rs2487896 | rs2487896__AA | rs2487896__AG |
|---|---|---|
| AA | 1 | 0 |
| AG | 0 | 1 |
| GG | −1 | −1 |

TABLE 19g

| rs3135391 | rs3135391__AA | rs3135391__AG |
|---|---|---|
| AA | 1 | 0 |
| AG | 0 | 1 |
| GG | −1 | −1 |

TABLE 19h

| rs4148871 | rs4148871__AA | rs4148871__AG |
|---|---|---|
| AA | 1 | 0 |
| AG | 0 | 1 |
| GG | −1 | −1 |

βX was calculated by multiplying the recoded value of each of the defined numeric variables by the coefficient in the table (each table defines a model):

TABLE 20

GM1003 model parameterization

| Variable | coefficient |
|---|---|
| Intercept | 9.3288 |
| rs11599624__AA | −0.6054 |
| rs11599624__AG | 1.8340 |
| rs12639443__CC | 1.6819 |
| rs12639443__CT | −5.2952 |
| rs13042992 | −2.1062 |
| rs13238613 | −1.6323 |
| rs17087180 | −5.6010 |
| rs17771939__CC | −8.0785 |
| rs17771939__CT | 2.0671 |
| rs17807327__AA | −4.1034 |
| rs17807327__AC | 7.1312 |
| rs2487896__AA | 3.4005 |
| rs2487896__AG | −4.5188 |
| rs3135391__AA | 1.1864 |
| rs3135391__AG | 0.4869 |
| rs4148871__AA | −3.8189 |
| rs4148871__AG | 2.5264 |
| rs4343256 | −6.9897 |
| rs4344916 | −4.3873 |
| rs9508834 | −4.0794 |

TABLE 21

GM1006 model parameterization

| variable | coefficient |
|---|---|
| Intercept | 0.8934 |
| rs12256889 | −0.3642 |
| rs12639443__CC | 0.3262 |
| rs12639443__CT | −2.8743 |
| rs13238613 | −1.2795 |
| rs1573706__CC | 0.2463 |
| rs1573706__CT | −1.3858 |
| rs17087180 | −1.3097 |
| rs17771939__CC | −3.1145 |
| rs17771939__CT | 0.5409 |
| rs17807327__AA | −3.2420 |
| rs17807327__AC | 4.8105 |
| rs2487896__AA | −1.4076 |
| rs2487896__AG | −1.0467 |
| rs4343256 | −4.0890 |
| rs4344916 | −2.4887 |
| rs4369324 | 1.7375 |
| rs4445746 | 2.8535 |
| rs9944913 | −1.8489 |

TABLE 22

GM1011 model parameterization

| variable | coefficient |
|---|---|
| Intercept | 6.2733 |
| rs10988087 | −1.6114 |
| rs12639443__CC | 1.3759 |
| rs12639443__CT | −1.4160 |
| rs13042992 | −1.9210 |
| rs13238613 | −2.9116 |
| rs1573706__CC | 1.2609 |
| rs1573706__CT | −0.7329 |
| rs17087180 | −5.9857 |
| rs17771939__CC | −3.3508 |
| rs17771939__CT | 1.2529 |
| rs17807327__AA | −3.0312 |
| rs17807327__AC | 1.9158 |
| rs4148871__AA | −0.5022 |
| rs4148871__AG | 0.4602 |
| rs4344916 | −2.3358 |
| rs6097801 | 1.3835 |
| rs9508834 | −2.8596 |

TABLE 23

| GM1012 model parameterization | |
| --- | --- |
| variable | coefficient |
| Intercept | 4.8013 |
| rs10988087 | −1.3216 |
| rs12256889 | −1.4875 |
| rs12639443__CC | 0.8026 |
| rs12639443__CT | −2.1054 |
| rs17087180 | −0.9015 |
| rs17771939__CC | −4.1661 |
| rs17771939__CT | 1.2859 |
| rs2177073 | 0.7441 |
| rs2521644 | −1.6096 |
| rs4344916 | −2.1699 |
| rs4369324 | 1.5320 |
| rs6097801 | 0.4036 |
| rs9508834 | −2.7916 |
| rs9944913 | −2.3396 |

TABLE 24

| GM2004 model parameterization | |
| --- | --- |
| variable | coefficient |
| Intercept | −2.4137 |
| rs10988087 | −3.2236 |
| rs11617134 | 3.2842 |
| rs12639443__CC | 2.5129 |
| rs12639443__CT | −5.6785 |
| rs13042992 | −2.2749 |
| rs17087180 | −7.7618 |
| rs17771939__CC | −7.4691 |
| rs17771939__CT | 1.7498 |
| rs17807327__AA | −3.8468 |
| rs17807327__AC | 6.1901 |
| rs2487896__AA | 3.2967 |
| rs2487896__AG | −5.6031 |
| rs4148871__AA | −3.4591 |
| rs4148871__AG | 2.3145 |
| rs4344916 | −4.3650 |
| rs4445746 | −0.7965 |
| rs6097801 | 1.5690 |
| rs9508834 | −5.2894 |

TABLE 25

| GM2014 model parameterization | |
| --- | --- |
| variable | coefficient |
| Intercept | −7.8077 |
| rs10988087 | −2.6273 |
| rs11617134 | 2.8140 |
| rs12639443__CC | 2.6274 |
| rs12639443__CT | −5.5577 |
| rs13042992 | −2.6555 |
| rs17087180 | −8.5303 |
| rs17771939__CC | −7.6788 |
| rs17771939__CT | 2.1630 |
| rs17807327__AA | −3.9942 |
| rs17807327__AC | 5.4647 |
| rs2487896__AA | 2.5228 |
| rs2487896__AG | −5.2338 |
| rs2521644 | −1.0118 |
| rs4148871__AA | −2.9546 |
| rs4148871__AG | 1.6983 |
| rs4344916 | −4.6078 |
| rs4445746 | 3.3039 |
| rs6097801 | 0.9950 |

TABLE 26

| GM2022 model parameterization | |
| --- | --- |
| variable | coefficient |
| Intercept | 0.7315 |
| rs10988087 | −2.7341 |
| rs12256889 | −0.6341 |
| rs12639443__CC | 2.2261 |
| rs12639443__CT | −3.7174 |
| rs17087180 | −3.8342 |
| rs17771939__CC | −4.7874 |
| rs17771939__CT | 0.9707 |
| rs17807327__AA | −2.3173 |
| rs17807327__AC | 4.6672 |
| rs2487896__AA | 1.4718 |
| rs2487896__AG | −3.3924 |
| rs4148871__AA | −2.0086 |
| rs4148871__AG | 0.8390 |
| rs4344916 | −3.3546 |
| rs6097801 | 1.6744 |
| rs9508834 | −3.6073 |

TABLE 27

| GM2027 model parameterization | |
| --- | --- |
| variable | coefficient |
| Intercept | 6.1931 |
| rs1007328 | 1.0823 |
| rs11617134 | 1.0945 |
| rs12639443__CC | 0.5046 |
| rs12639443__CT | −2.5608 |
| rs13238613 | −2.2037 |
| rs1573706__CC | 0.4573 |
| rs1573706__CT | −1.0221 |
| rs17087180 | −6.2114 |
| rs17771939__CC | −2.8678 |
| rs17771939__CT | 1.0193 |
| rs17807327__AA | −3.6846 |
| rs17807327__AC | 1.0093 |
| rs4343256 | −4.1274 |
| rs4344916 | −1.7464 |
| rs9508834 | −3.2225 |
| rs9944913 | −1.0139 |

TABLE 28

| GM2043 model parameterization | |
| --- | --- |
| variable | coefficient |
| Intercept | 0.9415 |
| rs12639443_CC | 0.5518 |
| rs12639443_CT | −4.7541 |
| rs17087180 | −4.2930 |
| rs17771939__CC | −5.9952 |
| rs17771939__CT | 1.4480 |
| rs17807327__AA | −3.7064 |
| rs17807327__AC | 4.9288 |
| rs2487896__AA | 1.3741 |
| rs2487896__AG | −3.4768 |
| rs4148871__AA | −2.5161 |
| rs4148871__AG | 1.7311 |
| rs4343256 | −4.8515 |
| rs4344916 | −3.2447 |
| rs4369324 | 1.6196 |
| rs4445746 | 0.3546 |
| rs6097801 | 1.7405 |
| rs9508834 | −3.8363 |
| rs9944913 | −2.3385 |

TABLE 29

| GM2068 model parameterization | |
|---|---|
| variable | coefficient |
| Intercept | −10.0845 |
| rs11617134 | 4.5538 |
| rs12639443_CC | 2.7799 |
| rs12639443_CT | −5.9539 |
| rs17087180 | −3.3532 |
| rs17771939_CC | −8.8437 |
| rs17771939_CT | 1.4087 |
| rs17807327_AA | −3.3124 |
| rs17807327_AC | 7.3851 |
| rs2487896_AA | 1.8417 |
| rs2487896_AG | −5.5723 |
| rs3135391_AA | 2.6828 |
| rs3135391_AG | −0.4052 |
| rs4148871_AA | −4.3161 |
| rs4148871_AG | 2.2073 |
| rs4344916 | −4.6260 |
| rs4369324 | 2.0398 |
| rs6097801 | 2.3816 |
| rs9508834 | −5.9421 |
| rs9944913 | −2.3240 |

TABLE 30

| GM2090 model parameterization | |
|---|---|
| variable | coefficient |
| Intercept | 4.0746 |
| rs10988087 | −2.0102 |
| rs12639443_CC | 1.6253 |
| rs12639443_CT | −3.1638 |
| rs13238613 | −1.6126 |
| rs17087180 | −2.6288 |
| rs17771939_CC | −4.5000 |
| rs17771939_CT | 0.9317 |
| rs2487896_AA | 1.0289 |
| rs2487896_AG | −2.7833 |
| rs4148871_AA | −1.7042 |
| rs4148871_AG | 0.4143 |
| rs4343256 | −1.5111 |
| rs4344916 | −3.9136 |
| rs9508834 | −3.2171 |

TABLE 31

| GM2094 model parameterization | |
|---|---|
| variable | coefficient |
| Intercept | −0.5847 |
| rs11617134 | 2.6429 |
| rs12256889 | −0.6230 |
| rs12639443_CC | 0.9349 |
| rs12639443_CT | −3.4318 |
| rs13042992 | −1.1986 |
| rs17087180 | −3.1618 |
| rs17771939_CC | −4.0279 |
| rs17771939_CT | 0.7481 |
| rs17807327_AA | −2.9966 |
| rs17807327_AC | 3.5249 |
| rs2177073 | −1.0156 |
| rs2487896_AA | 0.6515 |
| rs2487896_AG | −2.4396 |
| rs4343256 | −3.2118 |
| rs4344916 | −2.6570 |
| rs6097801 | 0.7221 |
| rs9508834 | −3.3025 |

TABLE 32

| GM2277 model parameterization | |
|---|---|
| variable | coefficient |
| Intercept | −8.0820 |
| rs10950359 | 0.6756 |
| rs11617134 | 3.0151 |
| rs12639443_CC | 1.8613 |
| rs12639443_CT | −4.7429 |
| rs17087180 | −3.0913 |
| rs17771939_CC | −5.5319 |
| rs17771939_CT | 1.5306 |
| rs2487896_AA | 1.9046 |
| rs2487896_AG | −4.3657 |
| rs2511064 | 2.0087 |
| rs3135391_AA | 1.3667 |
| rs3135391_AG | 0.1182 |
| rs4148871_AA | −3.7287 |
| rs4148871_AG | 0.7481 |
| rs4343256 | −1.2743 |
| rs4344916 | −4.1012 |
| rs9508834 | −2.9978 |
| rs9944913 | −2.3903 |

TABLE 33

| GM2338 model parameterization | |
|---|---|
| variable | coefficient |
| Intercept | 4.9303 |
| rs12256889 | −1.1920 |
| rs12639443_CC | 1.6753 |
| rs12639443_CT | −2.6864 |
| rs13042992 | −2.9155 |
| rs17087180 | −1.7977 |
| rs17771939_CC | −4.7042 |
| rs17771939_CT | 1.4442 |
| rs17807327_AA | −2.2426 |
| rs17807327_AC | 3.9474 |
| rs2487896_AA | −0.0709 |
| rs2487896_AG | −2.2441 |
| rs2521644 | −1.8304 |
| rs4344916 | −2.8265 |
| rs6097801 | 0.4595 |

TABLE 34

| GM3102 model parameterization | |
|---|---|
| variable | coefficient |
| Intercept | 5.5127 |
| rs10950359 | 1.4764 |
| rs10988087 | −2.9752 |
| rs11599624_AA | −0.6179 |
| rs11599624_AG | 2.8171 |
| rs12256889 | −1.1438 |
| rs12639443_CC | 2.0266 |
| rs12639443_CT | −2.4140 |
| rs13042992 | −1.3091 |
| rs17087180 | −4.0442 |
| rs17771939_CC | −3.7615 |
| rs17771939_CT | 1.0481 |
| rs17807327_AA | −1.3721 |
| rs17807327_AC | 2.5104 |
| rs2521644 | −1.6019 |
| rs3135391_AA | −1.4040 |
| rs3135391_AG | 0.7262 |
| rs4344916 | −2.4904 |
| rs9508834 | −2.7692 |

TABLE 35

GM3150 model parameterization

| variable | coefficient |
|---|---|
| Intercept | 4.7936 |
| rs1007328 | 1.5777 |
| rs10950359 | 1.7864 |
| rs12256889 | −0.4262 |
| rs12639443_CC | 1.5767 |
| rs12639443_CT | −2.3687 |
| rs13042992 | −1.5894 |
| rs1573706_CC | 0.4357 |
| rs1573706_CT | −1.4587 |
| rs17087180 | −3.4853 |
| rs17771939_CC | −2.4489 |
| rs17771939_CT | 0.5208 |
| rs17807327_AA | −3.1700 |
| rs17807327_AC | 2.8718 |
| rs4343256 | −2.7644 |
| rs4344916 | −2.0371 |
| rs947603 | −1.0418 |
| rs9508834 | −3.1861 |

TABLE 36

GM3332 model parameterization

| variable | coefficient |
|---|---|
| Intercept | 3.9516 |
| rs11599624_AA | −1.1461 |
| rs11599624_AG | 2.2491 |
| rs12256889 | −0.7295 |
| rs12639443_CC | 0.6782 |
| rs12639443_CT | −2.7278 |
| rs1573706_CC | 1.1868 |
| rs1573706_CT | −1.4399 |
| rs17087180 | −1.5211 |
| rs17771939_CC | −3.5821 |
| rs17771939_CT | 0.5404 |
| rs17807327_AA | −2.0945 |
| rs17807327_AC | 4.1007 |
| rs2177073 | −1.0741 |
| rs2487896_AA | −0.1642 |
| rs2487896_AG | −1.8886 |
| rs4344916 | −2.5787 |
| rs6097801 | 0.4844 |
| rs9508834 | −3.0143 |
| rs9944913 | −1.5636 |

The response probability was calculated using the formula:

$$P(\text{Response}) = \frac{e^{\beta X}}{1 + e^{\beta X}}$$

We have noticed that the following four SNPs were common to all models: rs4344916, rs12639443, rs17087180 and rs17771939. Two additional SNPs were common to at least 25/30 models containing the four SNPs described above: rs9508834 and rs17807327. Therefore, it would be appreciated by a person skilled in the art that sets of SNPs comprising rs4344916, rs12639443, rs17087180 and rs17771939 are expected to constitute models which are effective in predicting response to GA. The models may include other SNPs in addition to rs4344916, rs12639443, rs17087180 and rs17771939, including rs9508834, rs17807327, both, or other SNPs.

The models were retrospectively applied to the full cohort of 599 FORTE patients using different predictive thresholds. The ratios between the Annualized Relapse Rate (ARR) of genetically predicted responder patients (R) compared to the average ARR in genetically predicted non-responder patients (NR), and the ratios between the average ARR observed in the genetically predicted responder patients (R) compared to average ARR in the whole study population (All), according to each predictive threshold or two predictive thresholds, are presented in table 37. Table 37a shows data for models FM1, FM2, FM1a and GM1003, table 37b shows data for models GM1006, GM1011, GM1012 and GM2004, table 37c shows data for models GM2014, GM2022, GM2027 and 2043, table 37d shows data for models GM2068, GM2090, GM2094 and GM2277, and table 37e shows data for models GM2338, GM3102, GM3150 and GM3332.

Applying the 0.8 threshold for the FM1 model (presented in tables 5-7) in the FORTE cohort as well as two other cohorts (European/Canadian study and CORAL), we found that the average ARR in the GA-treated patients that were genetically predicted as responders in the FORTE and in the European/Canadian study was 76% and 81% lower, respectively, than in patients predicted as NR and 64% and 77% lower, respectively, than in the whole study population. In comparison, the average ARR in either placebo-treated patients or non treated patients (from European/Canadian study and CORAL, respectively) genetically predicted as responders was −7% and 26% lower, respectively, than in patients predicted as Non-Responders and 10% and 11% lower than in the whole study population. The reduction in average ARR by GA over placebo-treated patients in the responders population in the European/Canadian study was 79%.

TABLE 37

The Annualized Relapse Rate (ARR) average in all subjects of the FORTE trial compared to ARR average in genetically predicted responders (R) and non-responders (NR). UD = undefined

| | |
|---|---|
| ARR - | Annual Relapse Rate average as calculated for each genetically defined sub-population |
| Risk Ratio | The ratio between ARR observed in the genetically predicted responders (R) compared to the ARR in genetically predicted non-responders (NR) |
| ARR Vs all | The ratio between ARR observed in the genetically predicted super responders (R) compared to ARR in the whole study population (All) |

TABLE 37a

Models FM1, FM2, FM1a and GM1003

| | | FM1 | | | FM2 | | | FM1a | | | GM1003 | | |
|---|---|---|---|---|---|---|---|---|---|---|---|---|---|
| threshold | response prediction | ARR | Risk Ratio | ARR Vs. all | ARR | Risk Ratio | ARR Vs. all | ARR | Risk Ratio | ARR Vs. all | ARR | Risk Ratio | ARR Vs. all |
| NA | All | 0.241 | | 100% | 0.245 | | 100% | 0.245 | | 100% | 0.26 | | 100% |
| 0-0.1 | NR | 0.482 | 35% | 200% | 0.531 | 41% | 217% | 0.419 | 50% | 171% | 0.502 | 35% | 193% |
| 0.1-1 | R | 0.167 | | 69% | 0.217 | | 89% | 0.211 | | 86% | 1.176 | | 67% |

TABLE 37a-continued

Models FM1, FM2, FM1a and GM1003

| threshold | response prediction | FM1 | | | FM2 | | | FM1a | | | GM1003 | | |
|---|---|---|---|---|---|---|---|---|---|---|---|---|---|
| | | ARR | Risk Ratio | ARR Vs. all | ARR | Risk Ratio | ARR Vs. all | ARR | Risk Ratio | ARR Vs. all | ARR | Risk Ratio | ARR Vs. all |
| 0-0.2 | NR | 0.423 | 37% | 176% | 0.533 | 37% | 218% | 0.433 | 43% | 177% | 0.509 | 31% | 195% |
| 0.2-1 | R | 0.157 | | 65% | 0.195 | | 80% | 0.185 | | 75% | 0.16 | | 61% |
| 0-0.3 | NR | 0.427 | 32% | 177% | 0.485 | 37% | 198% | 0.415 | 44% | 169% | 0.51 | 29% | 196% |
| 0.3-1 | R | 0.135 | | 56% | 0.178 | | 73% | 0.182 | | 74% | 0.146 | | 56% |
| 0-0.4 | NR | 0.424 | 32% | 176% | 0.37 | 48% | 151% | 0.412 | 40% | 168% | 0.504 | 29% | 193% |
| 0.4-1 | R | 0.134 | | 55% | 0.178 | | 73% | 0.164 | | 67% | 0.145 | | 56% |
| 0-0.5 | NR | 0.423 | 32% | 175% | 0.344 | 51% | 141% | 0.343 | 46% | 140% | 0.491 | 29% | 189% |
| 0.5-1 | R | 0.134 | | 56% | 0.174 | | 71% | 0.159 | | 65% | 0.14 | | 54% |
| 0-0.6 | NR | 0.412 | 33% | 171% | 0.349 | 46% | 143% | 0.334 | 46% | 136% | 0.475 | 28% | 182% |
| 0.6-1 | R | 0.136 | | 56% | 0.16 | | 65% | 0.154 | | 63% | 0.132 | | 51% |
| 0-0.7 | NR | 0.383 | 34% | 159% | 0.332 | 37% | 135% | 0.333 | 40% | 136% | 0.468 | 28% | 180% |
| 0.7-1 | R | 0.132 | | 55% | 0.122 | | 50% | 0.138 | | 54% | 0.131 | | 50% |
| 0-0.8 | NR | 0.361 | 24% | 150% | 0.289 | 44% | 118% | 0.322 | 40% | 131% | 0.457 | 27% | 175% |
| 0.8-1 | R | 0.088 | | 36% | 0.126 | | 52% | 0.129 | | 53% | 0.125 | | 48% |
| 0-0.9 | NR | 0.318 | 31% | 132% | 0.259 | 49% | 106% | 0.302 | 36% | 123% | 0.438 | 28% | 168% |
| 0.9-1 | R | 0.098 | | 41% | 0.127 | | 52% | 0.11 | | 45% | 1.123 | | 47% |
| 0-0.1 | NR | 0.481 | 33% | 200% | 0.53 | 37% | 217% | 0.42 | 44% | 171% | 0.5 | 32% | 192% |
| 0.2-1 | R | 0.157 | | 65% | 0.195 | | 80% | 0.185 | | 75% | 0.16 | | 61% |
| 0.1-0.2 | UD | 0.252 | | 105% | 0.538 | | 220% | 0.463 | | 189% | 0.592 | | 227% |
| 0-0.1 | NR | 0.481 | 28% | 200% | 0.533 | 33% | 218% | 0.42 | 43% | 171% | 0.501 | 29% | 193% |
| 0.3-1 | R | 0.135 | | 56% | 0.178 | | 73% | 0.182 | | 74% | 0.146 | | 56% |
| 0.1-0.3 | UD | 0.326 | | 135% | 0.453 | | 185% | 0.408 | | 166% | 0.549 | | 211% |
| 0-0.1 | NR | 0.483 | 28% | 200% | 0.533 | 33% | 218% | 0.421 | 39% | 171% | 0.501 | 29% | 193% |
| 0.4-1 | R | 0.134 | | 56% | 0.178 | | 73% | 0.164 | | 67% | 0.145 | | 56% |
| 0.1-0.4 | UD | 0.322 | | 134% | 0.315 | | 129% | 0.404 | | 165% | 0.513 | | 197% |
| 0-0.1 | NR | 0.482 | 28% | 200% | 0.533 | 33% | 217% | 0.42 | 38% | 171% | 0.501 | 28% | 192% |
| 0.5-1 | R | 0.134 | | 56% | 0.174 | | 71% | 0.16 | | 65% | 0.14 | | 54% |
| 0.1-0.5 | UD | 0.319 | | 132% | 0.293 | | 120% | 0.299 | | 122% | 0.462 | | 177% |
| 0-0.1 | NR | 0.482 | 28% | 200% | 0.533 | 30% | 218% | 0.419 | 37% | 171% | 0.503 | 26% | 193% |
| 0.6-1 | R | 0.136 | | 56% | 0.16 | | 65% | 0.154 | | 63% | 0.132 | | 51% |
| 0.1-0.6 | UD | 0.299 | | 124% | 0.304 | | 124% | 0.291 | | 119% | 0.412 | | 158% |
| 0-0.1 | NR | 0.483 | 27% | 200% | 0.531 | 23% | 217% | 0.418 | 32% | 170% | 0.502 | 26% | 193% |
| 0.7-1 | R | 0.132 | | 55% | 0.122 | | 50% | 0.134 | | 54% | 0.131 | | 50% |
| 0.1-0.7 | UD | 0.265 | | 110% | 0.296 | | 121% | 0.297 | | 121% | 0.395 | | 152% |
| 0-0.1 | NR | 0.483 | 18% | 201% | 0.53 | 24% | 217% | 0.418 | 31% | 170% | 0.505 | 25% | 194% |
| 0.8-1 | R | 0.088 | | 36% | 0.127 | | 52% | 0.129 | | 53% | 0.125 | | 48% |
| 0.1-0.8 | UD | 0.273 | | 113% | 0.256 | | 105% | 0.284 | | 116% | 0.373 | | 143% |
| 0-0.1 | NR | 0.481 | 20% | 200% | 0.531 | 24% | 217% | 0.42 | 26% | 171% | 0.503 | 24% | 193% |
| 0.9-1 | R | 0.098 | | 41% | 0.127 | | 52% | 0.11 | | 45% | 0.123 | | 47% |
| 0.1-0.9 | UD | 0.225 | | 93% | 0.229 | | 94% | 0.265 | | 108% | 0.342 | | 132% |
| 0-0.2 | NR | 0.424 | 32% | 176% | 0.535 | 33% | 218% | 0.433 | 42% | 177% | 0.51 | 29% | 196% |
| 0.3-1 | R | 0.135 | | 56% | 0.178 | | 73% | 0.182 | | 74% | 0.146 | | 56% |
| 0.2-0.3 | UD | 0.445 | | 185% | 0.385 | | 157% | 0.254 | | 104% | 0.508 | | 195% |
| 0-0.2 | NR | 0.425 | 32% | 176% | 0.534 | 33% | 218% | 0.434 | 38% | 177% | 0.509 | 28% | 196% |
| 0.4-1 | R | 0.134 | | 55% | 0.178 | | 73% | 0.164 | | 67% | 0.145 | | 56% |
| 0.2-0.4 | UD | 0.419 | | 174% | 0.252 | | 103% | 0.349 | | 142% | 0.454 | | 174% |
| 0-0.2 | NR | 0.425 | 32% | 176% | 0.534 | 33% | 218% | 0.434 | 37% | 177% | 0.509 | 28% | 195% |
| −10.5 | R | 0.134 | | 56% | 0.174 | | 71% | 0.16 | | 65% | 0.14 | | 54% |
| 0.2-0.5 | UD | 0.409 | | 170% | 0.242 | | 99% | 0.243 | | 99% | 0.398 | | 153% |
| 0-0.2 | NR | 0.424 | 32% | 176% | 0.535 | 30% | 219% | 0.434 | 35% | 177% | 0.51 | 26% | 196% |
| 0.6-1 | R | 0.136 | | 56% | 0.16 | | 65% | 0.154 | | 63% | 0.132 | | 51% |
| 0.2-0.6 | UD | 0.353 | | 146% | 0.26 | | 106% | 0.241 | | 98% | 0.357 | | 137% |
| 0-0.2 | NR | 0.424 | 31% | 176% | 0.534 | 23% | 218% | 0.433 | 31% | 176% | 0.51 | 26% | 196% |
| 0.7-1 | R | 0.132 | | 55% | 0.122 | | 50% | 0.134 | | 55% | 0.131 | | 50% |
| 0.2-0.7 | UD | 0.272 | | 113% | 0.264 | | 108% | 0.255 | | 104% | 0.342 | | 131% |
| 0-0.2 | NR | 0.425 | 21% | 176% | 0.533 | 24% | 218% | 0.432 | 30% | 176% | 0.512 | 24% | 197% |
| 0.8-1 | R | 0.088 | | 36% | 0.127 | | 52% | 0.13 | | 53% | 0.125 | | 48% |
| 0.2-0.8 | UD | 0.279 | | 116% | 0.228 | | 93% | 0.246 | | 100% | 0.326 | | 125% |
| 0-0.2 | NR | 0.423 | 23% | 176% | 0.533 | 24% | 218% | 0.434 | 25% | 177% | 0.51 | 24% | 196% |
| 0.9-1 | R | 0.098 | | 41% | 0.126 | | 52% | 0.11 | | 45% | 0.123 | | 47% |
| 0.2-0.9 | UD | 0.218 | | 91% | 0.206 | | 84% | 0.232 | | 94% | 0.298 | | 115% |
| 0-0.3 | NR | 0.427 | 31% | 177% | 0.485 | 37% | 198% | 0.416 | 39% | 170% | 0.51 | 28% | 196% |
| 0.4-1 | R | 0.134 | | 55% | 0.178 | | 73% | 0.164 | | 67% | 0.145 | | 56% |
| 0.3-0.4 | UD | 0.236 | | 98% | 0.18 | | 73% | 0.394 | | 161% | 0.259 | | 99% |
| 0-0.3 | NR | 0.427 | 31% | 177% | 0.485 | 36% | 198% | 0.415 | 39% | 169% | 0.509 | 28% | 196% |
| 0.5-1 | R | 0.134 | | 55% | 0.175 | | 71% | 0.16 | | 65% | 0.14 | | 54% |
| 0.3-0.5 | UD | 0.201 | | 84% | 0.189 | | 77% | 0.241 | | 98% | 0.29 | | 111% |
| 0-0.3 | NR | 0.427 | 32% | 177% | 0.486 | 33% | 198% | 0.415 | 37% | 169% | 0.51 | 26% | 196% |
| 0.6-1 | R | 0.136 | | 56% | 0.16 | | 65% | 0.154 | | 63% | 0.132 | | 51% |
| 0.3-0.6 | UD | 0.101 | | 42% | 0.221 | | 90% | 0.239 | | 97% | 0.29 | | 111% |
| 0-0.3 | NR | 0.427 | 31% | 177% | 0.485 | 25% | 198% | 0.415 | 32% | 169% | 0.51 | 26% | 196% |

TABLE 37a-continued

Models FM1, FM2, FM1a and GM1003

| | | FM1 | | | FM2 | | | FM1a | | | GM1003 | | |
|---|---|---|---|---|---|---|---|---|---|---|---|---|---|
| threshold | response prediction | ARR | Risk Ratio | ARR Vs. all | ARR | Risk Ratio | ARR Vs. all | ARR | Risk Ratio | ARR Vs. all | ARR | Risk Ratio | ARR Vs. all |
| 0.7-1 | R | 0.132 | | 55% | 0.122 | | 50% | 0.134 | | 55% | 0.131 | | 50% |
| 0.3-0.7 | UD | 0.153 | | 63% | 0.241 | | 98% | 0.255 | | 104% | 0.278 | | 107% |
| 0-0.3 | NR | 0.428 | 21% | 178% | 0.485 | 26% | 198% | 0.414 | 31% | 169% | 0.511 | 24% | 196% |
| 0.8-1 | R | 0.088 | | 36% | 0.127 | | 52% | 0.13 | | 53% | 0.125 | | 48% |
| 0.3-0.8 | UD | 0.238 | | 99% | 0.206 | | 84% | 0.245 | | 100% | 0.276 | | 106% |
| 0-0.3 | NR | 0.427 | 23% | 177% | 0.485 | 26% | 198% | 0.416 | 26% | 169% | 0.51 | 24% | 196% |
| 0.9-1 | R | 0.098 | | 41% | 0.127 | | 52% | 0.11 | | 45% | 0.123 | | 47% |
| 0.3-0.9 | UD | 0.179 | | 74% | 0.187 | | 76% | 0.23 | | 94% | 0.253 | | 97% |
| 0-0.3 | NR | 0.424 | 32% | 176% | 0.37 | 47% | 151% | 0.412 | 39% | 168% | 0.503 | 28% | 193% |
| 0.5-1 | R | 0.134 | | 56% | 0.174 | | 71% | 0.16 | | 65% | 0.14 | | 54% |
| 0.4-0.5 | UD | 0 | | 0% | 0.21 | | 86% | 0.178 | | 72% | 0.302 | | 116% |
| 0-0.4 | NR | 0.425 | 32% | 176% | 0.37 | 43% | 151% | 0.412 | 37% | 168% | 0.504 | 26% | 194% |
| 0.6-1 | R | 0.136 | | 56% | 0.16 | | 65% | 0.154 | | 63% | 0.132 | | 51% |
| 0.4-0.6 | UD | 0 | | 0% | 0.276 | | 113% | 0.189 | | 77% | 0.294 | | 113% |
| 0-0.4 | NR | 0.424 | 31% | 176% | 0.369 | 33% | 151% | 0.412 | 33% | 168% | 0.504 | 26% | 194% |
| 0.7-1 | R | 0.133 | | 55% | 0.122 | | 50% | 0.134 | | 55% | 0.131 | | 50% |
| 0.4-0.7 | UD | 0.143 | | 59% | 0.276 | | 113% | 0.22 | | 90% | 0.28 | | 108% |
| 0-0.4 | NR | 0.425 | | 176% | 0.37 | | 151% | 0.412 | | 168% | 0.505 | | 194% |
| 0-0.7 | NR | 0.384 | 23% | 159% | 0.332 | 38% | 135% | 0.333 | 39% | 136% | 0.469 | 26% | 180% |
| 0.8-1 | R | 0.088 | | 36% | 0.127 | | 52% | 0.129 | | 53% | 0.124 | | 48% |
| 0.7-0.8 | UD | 0.284 | | 118% | 0.112 | | 46% | 0.172 | | 70% | 0.27 | | 104% |
| 0-0.7 | NR | 0.383 | 26% | 159% | 0.332 | 38% | 135% | 0.333 | 33% | 136% | 0.468 | 26% | 180% |
| 0.9-1 | R | 0.098 | | 41% | 0.127 | | 52% | 0.11 | | 45% | 0.123 | | 47% |
| 0.7-0.9 | UD | 0.188 | | 78% | 0.12 | | 49% | 0.18 | | 73% | 0.219 | | 84% |
| 0-0.8 | NR | 0.362 | 27% | 150% | 0.289 | 44% | 118% | 0.322 | 34% | 131% | 0.457 | 27% | 175% |
| 0.9-1 | R | 0.098 | | 41% | 0.127 | | 52% | 0.11 | | 45% | 0.123 | | 47% |
| 0.8-0.9 | UD | 0.043 | | 18% | 0.126 | | 51% | 0.182 | | 74% | 0.16 | | 61% |

TABLE 37b

Models GM1006, GM1011, GM1012 and GM2004.

| | | GM1006 | | | GM1011 | | | GM1012 | | | GM2004 | | |
|---|---|---|---|---|---|---|---|---|---|---|---|---|---|
| threshold | response prediction | ARR | Risk Ratio | ARR Vs. all | ARR | Risk Ratio | ARR Vs. all | ARR | Risk Ratio | ARR Vs. all | ARR | Risk Ratio | ARR Vs. all |
| NA | All | 0.253 | | 100% | 0.256 | | 100% | 0.251 | | 100% | 0.255 | | 100% |
| 0-0.1 | NR | 0.597 | 26% | 235% | 0.621 | 26% | 242% | 0.58 | 29% | 231% | 0.511 | 31% | 200% |
| 0.1-1 | R | 0.157 | | 62% | 0.16 | | 63% | 0.169 | | 67% | 0.157 | | 62% |
| 0-0.2 | NR | 0.55 | 26% | 217% | 0.578 | 25% | 225% | 0.528 | 30% | 210% | 0.513 | 27% | 201% |
| 0.2-1 | R | 0.143 | | 56% | 0.142 | | 55% | 0.157 | | 62% | 0.139 | | 54% |
| 0-0.3 | NR | 0.51 | 27% | 201% | 0.549 | 25% | 214% | 0.514 | 27% | 205% | 0.505 | 27% | 198% |
| 0.3-1 | R | 0.139 | | 55% | 0.135 | | 53% | 0.138 | | 55% | 0.134 | | 52% |
| 0-0.4 | NR | 0.491 | 28% | 194% | 0.495 | 28% | 193% | 0.498 | 28% | 198% | 0.493 | 27% | 194% |
| 0.4-1 | R | 0.137 | | 54% | 0.137 | | 53% | 0.137 | | 54% | 0.131 | | 51% |
| 0-0.5 | NR | 0.463 | 30% | 183% | 0.48 | 27% | 187% | 0.479 | 27% | 191% | 0.488 | 27% | 191% |
| 0.5-1 | R | 0.138 | | 55% | 0.13 | | 51% | 0.129 | | 51% | 0.13 | | 51% |
| 0-0.6 | NR | 0.452 | 29% | 178% | 0.451 | 27% | 176% | 0.442 | 28% | 176% | 0.494 | 24% | 194% |
| 0.6-1 | R | 0.129 | | 51% | 0.12 | | 47% | 0.123 | | 49% | 0.118 | | 46% |
| 0-0.7 | NR | 0.424 | 30% | 167% | 0.422 | 29% | 165% | 0.416 | 30% | 166% | 0.484 | 23% | 190% |
| 0.7-1 | R | 0.126 | | 50% | 0.121 | | 47% | 0.124 | | 49% | 0.11 | | 43% |
| 0-0.8 | NR | 0.397 | 32% | 157% | 0.41 | 29% | 160% | 0.386 | 32% | 154% | 0.447 | 25% | 175% |
| 0.8-1 | R | 0.128 | | 50% | 0.118 | | 46% | 0.125 | | 50% | 0.113 | | 44% |
| 0-0.9 | NR | 0.377 | 33% | 149% | 0.381 | 31% | 149% | 0.358 | 33% | 143% | 0.417 | 27% | 163% |
| 0.9-1 | R | 0.123 | | 48% | 0.119 | | 46% | 0.118 | | 47% | 0.114 | | 45% |
| 0-0.1 | NR | 0.597 | 24% | 236% | 0.622 | 23% | 242% | 0.581 | 27% | 231% | 0.512 | 27% | 201% |
| 0.2-1 | R | 0.143 | | 57% | 0.142 | | 55% | 0.157 | | 62% | 0.139 | | 54% |
| 0.1-0.2 | UD | 0.348 | | 137% | 0.409 | | 160% | 0.332 | | 132% | 0.517 | | 203% |
| 0-0.1 | NR | 0.595 | 23% | 235% | 0.623 | 22% | 243% | 0.584 | 24% | 232% | 0.513 | 26% | 201% |
| 0.3-1 | R | 0.139 | | 55% | 0.135 | | 53% | 0.138 | | 55% | 0.134 | | 52% |
| 0.1-0.3 | UD | 0.296 | | 117% | 0.366 | | 143% | 0.376 | | 150% | 0.463 | | 181% |
| 0-0.1 | NR | 0.595 | 23% | 235% | 0.624 | 22% | 243% | 0.584 | 23% | 233% | 0.512 | 26% | 201% |
| 0.4-1 | R | 0.138 | | 54% | 0.136 | | 53% | 0.136 | | 54% | 0.131 | | 51% |
| 0.1-0.4 | UD | 0.279 | | 110% | 0.282 | | 110% | 0.351 | | 140% | 0.414 | | 162% |
| 0-0.1 | NR | 0.595 | 24% | 235% | 0.624 | 21% | 243% | 0.585 | 22% | 233% | 0.513 | 25% | 201% |

TABLE 37b-continued

Models GM1006, GM1011, GM1012 and GM2004.

| | | Model: | | | | | | | | | | |
|---|---|---|---|---|---|---|---|---|---|---|---|---|
| | | GM1006 | | | GM1011 | | | GM1012 | | | GM2004 | | |
| threshold | response prediction | ARR | Risk Ratio | ARR Vs. all | ARR | Risk Ratio | ARR Vs. all | ARR | Risk Ratio | ARR Vs. all | ARR | Risk Ratio | ARR Vs. all |
|---|---|---|---|---|---|---|---|---|---|---|---|---|---|
| 0.5-1 | R | 0.14 | | 55% | 0.13 | | 51% | 0.128 | | 51% | 0.13 | | 51% |
| 0.1-0.5 | UD | 0.241 | | 95% | 0.284 | | 111% | 0.338 | | 134% | 0.392 | | 154% |
| 0-0.1 | NR | 0.593 | 22% | 234% | 0.622 | 19% | 243% | 0.584 | 21% | 232% | 0.512 | 23% | 201% |
| 0.6-1 | R | 0.131 | | 52% | 0.12 | | 47% | 0.123 | | 49% | 0.118 | | 46% |
| 0.1-0.6 | UD | 0.256 | | 101% | 0.275 | | 107% | 0.301 | | 120% | 0.434 | | 170% |
| 0-0.1 | NR | 0.593 | 22% | 234% | 0.621 | 19% | 242% | 0.583 | 21% | 232% | 0.513 | 21% | 201% |
| 0.7-1 | R | 0.128 | | 51% | 0.121 | | 47% | 0.124 | | 49% | 0.11 | | 43% |
| 0.1-0.7 | UD | 0.24 | | 95% | 0.249 | | 97% | 0.274 | | 109% | 0.413 | | 162% |
| 0-0.1 | NR | 0.594 | 22% | 234% | 0.621 | 19% | 242% | 0.583 | 21% | 232% | 0.512 | 22% | 201% |
| 0.8-1 | R | 0.13 | | 51% | 0.119 | | 46% | 0.125 | | 50% | 0.113 | | 44% |
| 0.1-0.8 | UD | 0.218 | | 86% | 0.242 | | 95% | 0.247 | | 98% | 0.326 | | 128% |
| 0-0.1 | NR | 0.595 | 21% | 235% | 0.621 | 19% | 242% | 0.582 | 20% | 232% | 0.512 | 22% | 201% |
| 0.9-1 | R | 0.125 | | 49% | 0.12 | | 47% | 0.118 | | 47% | 0.114 | | 45% |
| 0.1-0.9 | UD | 0.212 | | 84% | 0.221 | | 86% | 0.231 | | 92% | 0.277 | | 108% |
| 0-0.2 | NR | 0.549 | 25% | 217% | 0.579 | 23% | 226% | 0.531 | 26% | 211% | 0.513 | 26% | 201% |
| 0.3-1 | R | 0.139 | | 55% | 0.135 | | 53% | 0.138 | | 55% | 0.134 | | 52% |
| 0.2-0.3 | UD | 0.218 | | 86% | 0.289 | | 113% | 0.422 | | 168% | 0.34 | | 134% |
| 0-0.2 | NR | 0.549 | 25% | 217% | 0.579 | 23% | 226% | 0.531 | 26% | 211% | 0.513 | 26% | 201% |
| 0.4-1 | R | 0.138 | | 54% | 0.136 | | 53% | 0.137 | | 54% | 0.131 | | 51% |
| 0.2-0.4 | UD | 0.211 | | 83% | 0.191 | | 74% | 0.364 | | 145% | 0.297 | | 116% |
| 0-0.2 | NR | 0.55 | 25% | 217% | 0.58 | 22% | 226% | 0.531 | 24% | 211% | 0.513 | 25% | 201% |
| -10.5 | R | 0.14 | | 55% | 0.13 | | 51% | 0.129 | | 51% | 0.13 | | 51% |
| 0.2-0.5 | UD | 0.168 | | 66% | 0.216 | | 84% | 0.339 | | 135% | 0.28 | | 110% |
| 0-0.2 | NR | 0.548 | 24% | 216% | 0.579 | 21% | 226% | 0.53 | 23% | 211% | 0.513 | 23% | 201% |
| 0.6-1 | R | 0.131 | | 52% | 0.121 | | 47% | 0.123 | | 49% | 0.118 | | 46% |
| 0.2-0.6 | UD | 0.211 | | 83% | 0.225 | | 88% | 0.288 | | 115% | 0.379 | | 149% |
| 0-0.2 | NR | 0.548 | 23% | 216% | 0.578 | 21% | 225% | 0.53 | 23% | 211% | 0.514 | 21% | 201% |
| 0.7-1 | R | 0.128 | | 50% | 0.121 | | 47% | 0.124 | | 49% | 0.11 | | 43% |
| 0.2-0.7 | UD | 0.201 | | 79% | 0.202 | | 79% | 0.256 | | 102% | 0.364 | | 143% |
| 0-0.2 | NR | 0.549 | 24% | 217% | 0.578 | 21% | 225% | 0.53 | 24% | 211% | 0.513 | 22% | 201% |
| 0.8-1 | R | 0.13 | | 51% | 0.119 | | 47% | 0.125 | | 50% | 0.113 | | 44% |
| 0.2-0.8 | UD | 0.18 | | 71% | 0.198 | | 77% | 0.226 | | 90% | 0.266 | | 104% |
| 0-0.2 | NR | 0.549 | 23% | 217% | 0.578 | 21% | 225% | 0.529 | 22% | 211% | 0.513 | 22% | 201% |
| 0.9-1 | R | 0.125 | | 49% | 0.12 | | 47% | 0.118 | | 47% | 0.115 | | 45% |
| 0.2-0.9 | UD | 0.181 | | 72% | 0.182 | | 71% | 0.213 | | 85% | 0.221 | | 86% |
| 0-0.3 | NR | 0.51 | 27% | 201% | 0.549 | 25% | 214% | 0.514 | 27% | 205% | 0.505 | 26% | 198% |
| 0.4-1 | R | 0.137 | | 54% | 0.136 | | 53% | 0.137 | | 54% | 0.131 | | 51% |
| 0.3-0.4 | UD | 0.2 | | 79% | 0.122 | | 47% | 0.207 | | 83% | 0.25 | | 98% |
| 0-0.3 | NR | 0.51 | 27% | 201% | 0.549 | 24% | 214% | 0.515 | 25% | 205% | 0.505 | 26% | 198% |
| 0.5-1 | R | 0.139 | | 55% | 0.13 | | 51% | 0.129 | | 51% | 0.13 | | 51% |
| 0.3-0.5 | UD | 0.13 | | 51% | 0.184 | | 72% | 0.259 | | 103% | 0.238 | | 93% |
| 0-0.3 | NR | 0.509 | 26% | 201% | 0.549 | 22% | 214% | 0.515 | 24% | 205% | 0.505 | 23% | 198% |
| 0.6-1 | R | 0.13 | | 51% | 0.121 | | 47% | 0.124 | | 49% | 0.118 | | 46% |
| 0.3-0.6 | UD | 0.208 | | 82% | 0.208 | | 81% | 0.224 | | 89% | 0.396 | | 155% |
| 0-0.3 | NR | 0.509 | 25% | 201% | 0.549 | 22% | 214% | 0.515 | 24% | 205% | 0.505 | 22% | 198% |
| 0.7-1 | R | 0.127 | | 50% | 0.122 | | 47% | 0.124 | | 49% | 0.11 | | 43% |
| 0.3-0.7 | UD | 0.196 | | 77% | 0.184 | | 72% | 0.196 | | 78% | 0.37 | | 145% |
| 0-0.3 | NR | 0.51 | 25% | 201% | 0.549 | 22% | 214% | 0.515 | 24% | 205% | 0.505 | 22% | 198% |
| 0.8-1 | R | 0.129 | | 51% | 0.12 | | 47% | 0.125 | | 50% | 0.113 | | 44% |
| 0.3-0.8 | UD | 0.172 | | 68% | 0.182 | | 71% | 0.175 | | 70% | 0.253 | | 99% |
| 0-0.3 | NR | 0.51 | 24% | 201% | 0.549 | 22% | 214% | 0.514 | 23% | 205% | 0.505 | 23% | 198% |
| 0.9-1 | R | 0.124 | | 49% | 0.12 | | 47% | 0.118 | | 47% | 0.115 | | 45% |
| 0.3-0.9 | UD | 0.175 | | 69% | 0.166 | | 65% | 0.173 | | 69% | 0.206 | | 81% |
| 0-0.3 | NR | 0.492 | 28% | 194% | 0.495 | 26% | 193% | 0.498 | 26% | 198% | 0.494 | 26% | 194% |
| 0.5-1 | R | 0.139 | | 55% | 0.13 | | 51% | 0.129 | | 51% | 0.13 | | 51% |
| 0.4-0.5 | UD | 0.076 | | 30% | 0.295 | | 115% | 0.288 | | 115% | 0.216 | | 85% |
| 0-0.4 | NR | 0.491 | 26% | 194% | 0.494 | 24% | 192% | 0.498 | 25% | 198% | 0.494 | 24% | 194% |
| 0.6-1 | R | 0.13 | | 51% | 0.121 | | 47% | 0.124 | | 49% | 0.118 | | 46% |
| 0.4-0.6 | UD | 0.211 | | 83% | 0.264 | | 103% | 0.228 | | 91% | 0.492 | | 193% |
| 0-0.4 | NR | 0.491 | 26% | 194% | 0.494 | 25% | 193% | 0.498 | 25% | 198% | 0.494 | 22% | 194% |
| 0.7-1 | R | 0.127 | | 50% | 0.122 | | 47% | 0.124 | | 49% | 0.11 | | 43% |
| 0.4-0.7 | UD | 0.195 | | 77% | 0.211 | | 82% | 0.195 | | 77% | 0.409 | | 160% |
| 0-0.4 | NR | 0.491 | 26% | 194% | 0.494 | 24% | 193% | 0.498 | 25% | 198% | 0.494 | 23% | 194% |
| 0.8-1 | R | 0.129 | | 51% | 0.12 | | 47% | 0.125 | | 50% | 0.113 | | 44% |
| 0.4-0.8 | UD | 0.168 | | 66% | 0.204 | | 80% | 0.171 | | 68% | 0.253 | | 99% |
| 0-0.4 | NR | 0.491 | 25% | 194% | 0.495 | 24% | 193% | 0.498 | 24% | 198% | 0.494 | 23% | 194% |
| 0.9-1 | R | 0.123 | | 49% | 0.121 | | 47% | 0.118 | | 47% | 0.115 | | 45% |
| 0.4-0.9 | UD | 0.172 | | 68% | 0.178 | | 70% | 0.17 | | 68% | 0.201 | | 79% |
| 0-0.5 | NR | 0.462 | 28% | 182% | 0.479 | 25% | 187% | 0.479 | 26% | 191% | 0.486 | 24% | 191% |
| 0.6-1 | R | 0.129 | | 51% | 0.121 | | 47% | 0.124 | | 49% | 0.118 | | 46% |
| 0.5-0.6 | UD | 0.326 | | 129% | 0.246 | | 96% | 0.188 | | 75% | 0.656 | | 257% |

TABLE 37b-continued

Models GM1006, GM1011, GM1012 and GM2004.

| | | GM1006 | | | GM1011 | | | GM1012 | | | GM2004 | | |
|---|---|---|---|---|---|---|---|---|---|---|---|---|---|
| threshold | response prediction | ARR | Risk Ratio | ARR Vs. all | ARR | Risk Ratio | ARR Vs. all | ARR | Risk Ratio | ARR Vs. all | ARR | Risk Ratio | ARR Vs. all |
| 0-0.5 | NR | 0.462 | 27% | 182% | 0.479 | 25% | 187% | 0.479 | 26% | 191% | 0.487 | 23% | 191% |
| 0.7-1 | R | 0.126 | | 50% | 0.122 | | 47% | 0.124 | | 49% | 0.11 | | 43% |
| 0.5-0.7 | UD | 0.236 | | 93% | 0.185 | | 72% | 0.158 | | 63% | 0.452 | | 177% |
| 0-0.5 | NR | 0.462 | 28% | 182% | 0.479 | 25% | 187% | 0.479 | 26% | 191% | 0.487 | 23% | 191% |
| 0.8-1 | R | 0.128 | | 51% | 0.119 | | 47% | 0.125 | | 50% | 0.113 | | 44% |
| 0.5-0.8 | UD | 0.187 | | 74% | 0.182 | | 71% | 0.142 | | 57% | 0.258 | | 101% |
| 0-0.5 | NR | 0.462 | 27% | 182% | 0.48 | 25% | 187% | 0.479 | 25% | 191% | 0.488 | 24% | 191% |
| 0.9-1 | R | 0.123 | | 48% | 0.12 | | 47% | 0.118 | | 47% | 0.115 | | 45% |
| 0.5-0.9 | UD | 0.186 | | 73% | 0.159 | | 62% | 0.151 | | 60% | 0.2 | | 78% |
| 0-0.6 | NR | 0.451 | 28% | 178% | 0.451 | 27% | 176% | 0.442 | 28% | 176% | 0.494 | 22% | 194% |
| 0.7-1 | R | 0.126 | | 50% | 0.121 | | 47% | 0.124 | | 49% | 0.11 | | 43% |
| 0.6-0.7 | UD | 0.175 | | 69% | 0.105 | | 41% | 0.112 | | 45% | 0.325 | | 128% |
| 0-0.6 | NR | 0.452 | 28% | 178% | 0.451 | 26% | 176% | 0.442 | 28% | 176% | 0.494 | 23% | 194% |
| 0.8-1 | R | 0.128 | | 51% | 0.119 | | 46% | 0.125 | | 50% | 0.113 | | 44% |
| 0.6-0.8 | UD | 0.138 | | 54% | 0.13 | | 51% | 0.114 | | 45% | 0.16 | | 83% |
| 0-0.6 | NR | 0.452 | 27% | 178% | 0.451 | 27% | 176% | 0.442 | 27% | 176% | 0.494 | 23% | 194% |
| 0.9-1 | R | 0.123 | | 48% | 0.12 | | 47% | 0.118 | | 47% | 0.115 | | 45% |
| 0.6-0.9 | UD | 0.155 | | 61% | 0.121 | | 47% | 0.138 | | 55% | 0.133 | | 52% |
| 0-0.7 | NR | 0.424 | 30% | 167% | 0.422 | 28% | 165% | 0.416 | 30% | 165% | 0.484 | 23% | 190% |
| 0.8-1 | R | 0.128 | | 50% | 0.118 | | 46% | 0.125 | | 50% | 0.113 | | 44% |
| 0.7-0.8 | UD | 0.097 | | 38% | 0.17 | | 66% | 0.115 | | 46% | 0.053 | | 21% |
| 0-0.7 | NR | 0.424 | 29% | 167% | 0.422 | 28% | 165% | 0.416 | 28% | 166% | 0.484 | 24% | 190% |
| 0.9-1 | R | 0.122 | | 48% | 0.119 | | 46% | 0.118 | | 47% | 0.115 | | 45% |
| 0.7-0.9 | UD | 0.145 | | 57% | 0.129 | | 50% | 0.146 | | 58% | 0.075 | | 29% |
| 0-0.8 | NR | 0.398 | 31% | 157% | 0.41 | 29% | 160% | 0.386 | 31% | 154% | 0.447 | 26% | 175% |
| 0.9-1 | R | 0.122 | | 48% | 0.119 | | 46% | 0.118 | | 47% | 0.115 | | 45% |
| 0.8-0.9 | UD | 0.181 | | 71% | 0.111 | | 43% | 0.168 | | 67% | 0.093 | | 37% |

TABLE 37c

Models GM2014, GM2022, GM2027 and 2043.

| Model: | | GM2014 | | | GM2022 | | | GM2027 | | | GM2043 | | |
|---|---|---|---|---|---|---|---|---|---|---|---|---|---|
| threshold | response prediction | ARR | Risk Ratio | ARR Vs. all | ARR | Risk Ratio | ARR Vs. all | ARR | Risk Ratio | ARR Vs. all | ARR | Risk Ratio | ARR Vs. all |
| NA | All | 0.255 | | 100% | 0.253 | | 100% | 0.253 | | 100% | 0.258 | | 100% |
| 0-0.1 | NR | 0.528 | | 207% | 0.551 | | 218% | 0.558 | | 221% | 0.511 | | 198% |
| 0.1-1 | R | 0.153 | 29% | 60% | 0.162 | 29% | 64% | 0.159 | 28% | 63% | 0.16 | 31% | 62% |
| 0-0.2 | NR | 0.517 | | 203% | 0.535 | | 211% | 0.489 | | 193% | 0.501 | | 194% |
| 0.2-1 | R | 0.143 | 28% | 56% | 0.148 | 28% | 58% | 0.153 | 31% | 60% | 0.153 | 31% | 59% |
| 0-0.3 | NR | 0.503 | | 198% | 0.519 | | 205% | 0.47 | | 186% | 0.483 | | 187% |
| 0.3-1 | R | 0.13 | 26% | 51% | 0.144 | 28% | 57% | 0.145 | 31% | 57% | 0.144 | 30% | 56% |
| 0-0.4 | NR | 0.497 | | 195% | 0.498 | | 197% | 0.446 | | 176% | 0.47 | | 182% |
| 0.4-1 | R | 0.128 | 26% | 50% | 0.138 | 28% | 55% | 0.143 | 32% | 57% | 0.146 | 31% | 56% |
| 0-0.5 | NR | 0.482 | | 189% | 0.504 | | 199% | 0.431 | | 170% | 0.472 | | 183% |
| 0.5-1 | R | 0.122 | 25% | 48% | 0.117 | 23% | 46% | 0.138 | 32% | 54% | 0.128 | 27% | 49% |
| 0-0.6 | NR | 0.465 | | 183% | 0.482 | | 190% | 0.425 | | 168% | 0.466 | | 180% |
| 0.6-1 | R | 0.123 | 26% | 48% | 0.115 | 24% | 45% | 0.121 | 28% | 48% | 0.124 | 27% | 48% |
| 0-0.7 | NR | 0.461 | | 181% | 0.442 | | 175% | 0.403 | | 159% | 0.451 | | 174% |
| 0.7-1 | R | 0.118 | 26% | 46% | 0.121 | 27% | 48% | 0.119 | 30% | 47% | 0.12 | 27% | 46% |
| 0-0.8 | NR | 0.443 | | 174% | 0.419 | | 165% | 0.377 | | 149% | 0.423 | | 163% |
| 0.8-1 | R | 0.112 | 25% | 44% | 0.119 | 28% | 47% | 0.124 | 33% | 49% | 0.12 | 28% | 47% |
| 0-0.9 | NR | 0.416 | | 163% | 0.404 | | 160% | 0.357 | | 141% | 0.396 | | 153% |
| 0.9-1 | R | 0.107 | 26% | 42% | 0.115 | 28% | 45% | 0.111 | 31% | 44% | 0.117 | 30% | 45% |
| 0-0.1 | NR | 0.526 | | 207% | 0.552 | | 218% | 0.558 | | 221% | 0.51 | | 197% |
| 0.2-1 | R | 0.143 | 27% | 56% | 0.148 | 27% | 58% | 0.153 | 27% | 60% | 0.153 | 30% | 59% |
| 0.1-0.2 | UD | 0.425 | | 167% | 0.432 | | 171% | 0.231 | | 91% | 0.383 | | 148% |
| 0-0.1 | NR | 0.526 | | 206% | 0.552 | | 218% | 0.559 | | 221% | 0.509 | | 197% |
| 0.3-1 | R | 0.13 | 25% | 51% | 0.144 | 26% | 57% | 0.145 | 26% | 57% | 0.144 | 28% | 56% |
| 0.1-0.3 | UD | 0.408 | | 160% | 0.384 | | 152% | 0.257 | | 102% | 0.347 | | 134% |
| 0-0.1 | NR | 0.526 | | 207% | 0.551 | | 218% | 0.559 | | 221% | 0.509 | | 197% |
| 0.4-1 | R | 0.129 | 25% | 51% | 0.138 | 25% | 55% | 0.143 | 26% | 56% | 0.146 | 29% | 57% |
| 0.1-0.4 | UD | 0.385 | | 151% | 0.352 | | 139% | 0.24 | | 95% | 0.297 | | 115% |
| 0-0.1 | NR | 0.527 | | 207% | 0.552 | | 218% | 0.559 | | 221% | 0.511 | | 198% |
| 0.5-1 | R | 0.122 | 23% | 48% | 0.117 | 21% | 46% | 0.138 | 25% | 54% | 0.128 | 25% | 49% |
| 0.1-0.5 | UD | 0.356 | | 140% | 0.408 | | 161% | 0.241 | | 95% | 0.361 | | 140% |

TABLE 37c-continued

Models GM2014, GM2022, GM2027 and 2043.

| Model: | | GM2014 | | | GM2022 | | | GM2027 | | | GM2043 | | |
|---|---|---|---|---|---|---|---|---|---|---|---|---|---|
| threshold | response prediction | ARR | Risk Ratio | ARR Vs. all | ARR | Risk Ratio | ARR Vs. all | ARR | Risk Ratio | ARR Vs. all | ARR | Risk Ratio | ARR Vs. all |
| 0-0.1 | NR | 0.529 | | 208% | 0.551 | | 218% | 0.559 | | 221% | 0.511 | | 198% |
| 0.6-1 | R | 0.123 | 23% | 48% | 0.115 | 21% | 45% | 0.121 | 22% | 48% | 0.124 | 24% | 48% |
| 0.1-0.6 | UD | 0.315 | | 124% | 0.368 | | 146% | 0.266 | | 105% | 0.353 | | 137% |
| 0-0.1 | NR | 0.528 | | 208% | 0.551 | | 218% | 0.559 | | 221% | 0.51 | | 197% |
| 0.7-1 | R | 0.119 | 23% | 47% | 0.121 | 22% | 48% | 0.119 | 21% | 47% | 0.12 | 24% | 46% |
| 0.1-0.7 | UD | 0.317 | | 125% | 0.298 | | 118% | 0.248 | | 98% | 0.228 | | 127% |
| 0-0.1 | NR | 0.529 | | 208% | 0.552 | | 218% | 0.558 | | 221% | 0.51 | | 197% |
| 0.8-1 | R | 0.112 | 21% | 44% | 0.12 | 22% | 47% | 0.124 | 22% | 49% | 0.121 | 24% | 47% |
| 0.1-0.8 | UD | 0.298 | | 117% | 0.272 | | 108% | 0.221 | | 87% | 0.282 | | 109% |
| 0-0.1 | NR | 0.529 | | 208% | 0.551 | | 218% | 0.558 | | 220% | 0.51 | | 197% |
| 0.9-1 | R | 0.108 | 20% | 42% | 0.115 | 21% | 46% | 0.112 | 20% | 44% | 0.118 | 23% | 46% |
| 0.1-0.9 | UD | 0.268 | | 105% | 0.263 | | 104% | 0.218 | | 86% | 0.253 | | 98% |
| 0-0.2 | NR | 0.516 | | 203% | 0.535 | | 212% | 0.489 | | 194% | 0.501 | | 194% |
| 0.3-1 | R | 0.13 | 25% | 51% | 0.144 | 27% | 57% | 0.145 | 30% | 57% | 0.144 | 29% | 56% |
| 0.2-0.3 | UD | 0.394 | | 155% | 0.288 | | 114% | 0.303 | | 120% | 0.327 | | 126% |
| 0-0.2 | NR | 0.517 | | 203% | 0.535 | | 211% | 0.49 | | 194% | 0.501 | | 194% |
| 0.4-1 | R | 0.128 | 25% | 50% | 0.139 | 26% | 55% | 0.143 | 29% | 56% | 0.146 | 29% | 57% |
| 0.2-0.4 | UD | 0.36 | | 141% | 0.284 | | 112% | 0.248 | | 98% | 0.258 | | 100% |
| 0-0.2 | NR | 0.517 | | 203% | 0.536 | | 212% | 0.489 | | 194% | 0.502 | | 194% |
| -10.5 | R | 0.122 | 24% | 48% | 0.117 | 22% | 46% | 0.138 | 28% | 54% | 0.128 | 25% | 49% |
| 0.2-0.5 | UD | 0.329 | | 129% | 0.396 | | 156% | 0.248 | | 98% | 0.355 | | 137% |
| 0-0.2 | NR | 0.518 | | 203% | 0.534 | | 211% | 0.49 | | 194% | 0.502 | | 194% |
| 0.6-1 | R | 0.123 | 24% | 48% | 0.115 | 22% | 45% | 0.121 | 25% | 48% | 0.124 | 25% | 48% |
| 0.2-0.6 | UD | 0.28 | | 110% | 0.344 | | 136% | 0.283 | | 112% | 0.347 | | 134% |
| 0-0.2 | NR | 0.518 | | 203% | 0.534 | | 211% | 0.49 | | 194% | 0.502 | | 194% |
| 0.7-1 | R | 0.119 | 23% | 47% | 0.122 | 23% | 48% | 0.119 | 24% | 47% | 0.12 | 24% | 46% |
| 0.2-0.7 | UD | 0.287 | | 113% | 0.261 | | 103% | 0.254 | | 100% | 0.318 | | 123% |
| 0-0.2 | NR | 0.518 | | 204% | 0.535 | | 212% | 0.489 | | 193% | 0.501 | | 194% |
| 0.8-1 | R | 0.112 | 22% | 44% | 0.12 | 22% | 47% | 0.124 | 25% | 49% | 0.121 | 24% | 47% |
| 0.2-0.8 | UD | 0.271 | | 106% | 0.237 | | 94% | 0.218 | | 86% | 0.269 | | 104% |
| 0-0.2 | NR | 0.518 | | 203% | 0.535 | | 211% | 0.489 | | 193% | 0.501 | | 194% |
| 0.9-1 | R | 0.108 | 21% | 42% | 0.116 | 22% | 46% | 0.112 | 23% | 44% | 0.118 | 24% | 46% |
| 0.2-0.9 | UD | 0.244 | | 96% | 0.23 | | 91% | 0.215 | | 85% | 0.24 | | 93% |
| 0-0.3 | NR | 0.503 | | 198% | 0.518 | | 205% | 0.47 | | 186% | 0.483 | | 187% |
| 0.4-1 | R | 0.128 | 25% | 50% | 0.138 | 27% | 55% | 0.143 | 30% | 57% | 0.146 | 30% | 56% |
| 0.3-0.4 | UD | 0.221 | | 87% | 0.281 | | 111% | 0.182 | | 72% | 0 | | 0% |
| 0-0.3 | NR | 0.504 | | 198% | 0.519 | | 205% | 0.47 | | 186% | 0.484 | | 187% |
| 0.5-1 | R | 0.122 | 24% | 48% | 0.117 | 23% | 46% | 0.138 | 29% | 54% | 0.128 | 26% | 49% |
| 0.3-0.5 | UD | 0.265 | | 104% | 0.43 | | 170% | 0.215 | | 85% | 0.376 | | 146% |
| 0-0.3 | NR | 0.504 | | 198% | 0.518 | | 205% | 0.471 | | 186% | 0.484 | | 187% |
| 0.6-1 | R | 0.123 | 24% | 48% | 0.115 | 22% | 45% | 0.121 | 26% | 48% | 0.124 | 26% | 48% |
| 0.3-0.6 | UD | 0.207 | | 81% | 0.357 | | 141% | 0.276 | | 109% | 0.358 | | 139% |
| 0-0.3 | NR | 0.504 | | 198% | 0.518 | | 205% | 0.47 | | 186% | 0.483 | | 187% |
| 0.7-1 | R | 0.118 | 23% | 47% | 0.122 | 24% | 48% | 0.119 | 25% | 47% | 0.12 | 25% | 46% |
| 0.3-0.7 | UD | 0.23 | | 90% | 0.256 | | 101% | 0.241 | | 95% | 0.314 | | 121% |
| 0-0.3 | NR | 0.505 | | 198% | 0.519 | | 205% | 0.47 | | 186% | 0.482 | | 187% |
| 0.8-1 | R | 0.112 | 22% | 44% | 0.12 | 23% | 47% | 0.125 | 27% | 49% | 0.12 | 25% | 47% |
| 0.3-0.8 | UD | 0.228 | | 90% | 0.23 | | 91% | 0.201 | | 80% | 0.252 | | 97% |
| 0-0.3 | NR | 0.504 | | 198% | 0.519 | | 205% | 0.47 | | 186% | 0.483 | | 187% |
| 0.9-1 | R | 0.107 | 21% | 42% | 0.116 | 22% | 46% | 0.112 | 24% | 44% | 0.117 | 24% | 45% |
| 0.3-09 | UD | 0.208 | | 82% | 0.224 | | 89% | 0.202 | | 80% | 0.222 | | 86% |
| 0-0.3 | NR | 0.498 | | 195% | 0.5 | | 197% | 0.446 | | 176% | 0.472 | | 183% |
| 0.5-1 | R | 0.122 | 24% | 48% | 0.117 | 23% | 46% | 0.138 | 31% | 54% | 0.128 | 27% | 49% |
| 0.4-0.5 | UD | 0.279 | | 110% | 0.545 | | 216% | 0.248 | | 98% | 0.475 | | 184% |
| 0-0.4 | NR | 0.498 | | 195% | 0.498 | | 197% | 0.446 | | 177% | 0.471 | | 182% |
| 0.6-1 | R | 0.123 | 25% | 48% | 0.115 | 23% | 45% | 0.121 | 27% | 48% | 0.124 | 26% | 48% |
| 0.4-0.6 | UD | 0.205 | | 81% | 0.392 | | 155% | 0.316 | | 125% | 0.427 | | 165% |
| 0-0.4 | NR | 0.498 | | 196% | 0.498 | | 197% | 0.446 | | 176% | 0.471 | | 182% |
| 0.7-1 | R | 0.118 | 24% | 47% | 0.121 | 24% | 48% | 0.119 | 27% | 47% | 0.12 | 25% | 46% |
| 0.4-0.7 | UD | 0.232 | | 91% | 0.248 | | 98% | 0.258 | | 102% | 0.353 | | 136% |
| 0-0.4 | NR | 0.498 | | 196% | 0.498 | | 197% | 0.446 | | 176% | 0.47 | | 182% |
| 0.8-1 | R | 0.112 | 22% | 44% | 0.119 | 24% | 47% | 0.125 | 28% | 49% | 0.12 | 26% | 47% |
| 0.4-0.8 | UD | 0.229 | | 90% | 0.219 | | 87% | 0.204 | | 81% | 0.272 | | 105% |
| 0-0.4 | NR | 0.498 | | 196% | 0.498 | | 197% | 0.446 | | 176% | 0.47 | | 182% |
| 0.9-1 | R | 0.107 | 21% | 42% | 0.115 | 23% | 46% | 0.112 | 25% | 44% | 0.117 | 25% | 45% |
| 0.4-0.9 | UD | 0.207 | | 81% | 0.214 | | 85% | 0.204 | | 81% | 0.234 | | 91% |
| 0-0.5 | NR | 0.482 | | 189% | 0.504 | | 199% | 0.432 | | 171% | 0.472 | | 183% |
| 0.6-1 | R | 0.122 | 25% | 48% | 0.115 | 23% | 46% | 0.121 | 28% | 48% | 0.124 | 26% | 48% |
| 0.5-0.6 | UD | 0.1 | | 39% | 0.165 | | 65% | 0.365 | | 144% | 0.297 | | 115% |
| 0-0.5 | NR | 0.482 | | 190% | 0.504 | | 199% | 0.431 | | 170% | 0.472 | | 183% |
| 0.7-1 | R | 0.118 | 24% | 46% | 0.122 | 24% | 48% | 0.119 | 28% | 47% | 0.12 | 25% | 46% |
| 0.5-0.7 | UD | 0.19 | | 74% | 0.067 | | 27% | 0.261 | | 103% | 0.244 | | 94% |
| 0-0.5 | NR | 0.483 | | 190% | 0.504 | | 199% | 0.431 | | 170% | 0.472 | | 183% |

TABLE 37c-continued

Models GM2014, GM2022, GM2027 and 2043.

| Model: | | GM2014 | | | GM2022 | | | GM2027 | | | GM2043 | | |
|---|---|---|---|---|---|---|---|---|---|---|---|---|---|
| threshold | response prediction | ARR | Risk Ratio | ARR Vs. all | ARR | Risk Ratio | ARR Vs. all | ARR | Risk Ratio | ARR Vs. all | ARR | Risk Ratio | ARR Vs. all |
| 0.8-1 | R | 0.112 | 23% | 44% | 0.12 | 24% | 47% | 0.124 | 29% | 49% | 0.121 | 26% | 47% |
| 0.5-0.8 | UD | 0.208 | | 82% | 0.101 | | 40% | 0.193 | | 76% | 0.178 | | 69% |
| 0-0.5 | NR | 0.483 | | 190% | 0.504 | | 199% | 0.431 | | 170% | 0.472 | | 183% |
| 0.9-1 | R | 0.107 | 22% | 42% | 0.116 | 23% | 46% | 0.112 | 26% | 44% | 0.118 | 25% | 46% |
| 0.5-0.9 | UD | 0.19 | | 74% | 0.122 | | 48% | 0.198 | | 78% | 0.167 | | 65% |
| 0-0.6 | NR | 0.465 | | 183% | 0.482 | | 191% | 0.425 | | 168% | 0.466 | | 180% |
| 0.7-1 | R | 0.118 | 25% | 46% | 0.121 | 25% | 48% | 0.119 | 28% | 47% | 0.12 | 26% | 46% |
| 0.6-0.7 | UD | 0.341 | | 134% | 0 | | 0% | 0.15 | | 59% | 0.217 | | 84% |
| 0-0.6 | NR | 0.465 | | 183% | 0.482 | | 190% | 0.425 | | 168% | 0.466 | | 180% |
| 0.8-1 | R | 0.112 | 24% | 44% | 0.119 | 25% | 47% | 0.125 | 29% | 49% | 0.121 | 26% | 47% |
| 0.6-0.8 | UD | 0.253 | | 99% | 0.079 | | 31% | 0.101 | | 40% | 0.153 | | 59% |
| 0-0.6 | NR | 0.465 | | 183% | 0.482 | | 190% | 0.425 | | 168% | 0.466 | | 180% |
| 0.9-1 | R | 0.107 | 23% | 42% | 0.115 | 24% | 46% | 0.112 | 26% | 44% | 0.118 | 25% | 46% |
| 0.6-0.9 | UD | 0.208 | | 82% | 0.112 | | 44% | 0.149 | | 59% | 0.152 | | 59% |
| 0-0.7 | NR | 0.462 | | 181% | 0.442 | | 175% | 0.403 | | 159% | 0.451 | | 174% |
| 0.8-1 | R | 0.112 | 24% | 44% | 0.119 | 27% | 47% | 0.124 | 31% | 49% | 0.121 | 27% | 47% |
| 0.7-0.8 | UD | 0.223 | | 88% | 0.148 | | 59% | 0.051 | | 20% | 0.106 | | 41% |
| 0-0.7 | NR | 0.461 | | 181% | 0.442 | | 175% | 0.403 | | 159% | 0.451 | | 174% |
| 0.9-1 | R | 0.107 | 23% | 42% | 0.115 | 26% | 45% | 0.112 | 28% | 44% | 0.118 | 26% | 46% |
| 0.7-0.9 | UD | 0.19 | | 74% | 0.167 | | 66% | 0.149 | | 59% | 0.132 | | 51% |
| 0-0.8 | NR | 0.443 | | 174% | 0.418 | | 165% | 0.377 | | 149% | 0.423 | | 163% |
| 0.9-1 | R | 0.107 | 24% | 42% | 0.115 | 28% | 45% | 0.112 | 30% | 44% | 0.117 | 28% | 45% |
| 0.8-0.9 | UD | 0.165 | | 65% | 0.192 | | 76% | 0.205 | | 81% | 0.15 | | 58% |

TABLE 37d

Models GM2068, GM2090, GM2094 and GM2277.

| | | Model: | | | | | | | | | | | |
|---|---|---|---|---|---|---|---|---|---|---|---|---|---|
| | | GM2068 | | | GM2090 | | | GM2094 | | | GM2277 | | |
| threshold | response prediction | ARR | Risk Ratio | ARR Vs. all | ARR | Risk Ratio | ARR Vs. all | ARR | Risk Ratio | ARR Vs. all | ARR | Risk Ratio | ARR Vs. all |
| NA | All | 0.256 | | 100% | 0.254 | | 100% | 0.251 | | 100% | 0.258 | | 100% |
| 0-0.1 | NR | 0.486 | 34% | 190% | 0.514 | 33% | 203% | 0.537 | 32% | 214% | 0.487 | 34% | 189% |
| 0.1-1 | R | 0.165 | | 64% | 0.172 | | 68% | 0.17 | | 68% | 0.164 | | 64% |
| 0-0.2 | NR | 0.489 | 32% | 191% | 0.516 | 29% | 204% | 0.496 | 32% | 197% | 0.485 | 30% | 188% |
| 0.2-1 | R | 0.155 | | 60% | 0.15 | | 59% | 0.157 | | 63% | 0.147 | | 57% |
| 0-0.3 | NR | 0.474 | 31% | 185% | 0.516 | 25% | 203% | 0.479 | 30% | 191% | 0.465 | 31% | 180% |
| 0.3-1 | R | 0.148 | | 58% | 0.13 | | 51% | 0.144 | | 57% | 0.144 | | 56% |
| 0-0.4 | NR | 0.461 | 31% | 180% | 0.482 | 27% | 190% | 0.469 | 30% | 187% | 0.443 | 33% | 172% |
| 0.4-1 | R | 0.144 | | 56% | 0.13 | | 51% | 0.139 | | 56% | 0.145 | | 56% |
| 0-0.5 | NR | 0.447 | 32% | 174% | 0.461 | 29% | 182% | 0.45 | 31% | 179% | 0.437 | 32% | 169% |
| 0.5-1 | R | 0.143 | | 56% | 0.132 | | 52% | 0.14 | | 56% | 0.138 | | 53% |
| 0-0.6 | NR | 0.454 | 29% | 177% | 0.441 | 29% | 174% | 0.439 | 28% | 175% | 0.427 | 31% | 166% |
| 0.6-1 | R | 0.133 | | 52% | 0.126 | | 50% | 0.125 | | 50% | 0.132 | | 51% |
| 0-0.7 | NR | 0.447 | 29% | 174% | 0.422 | 30% | 166% | 0.421 | 30% | 168% | 0.419 | 31% | 162% |
| 0.7-1 | R | 0.128 | | 50% | 0.127 | | 50% | 0.127 | | 50% | 0.129 | | 50% |
| 0-0.8 | NR | 0.433 | 29% | 169% | 0.398 | 31% | 157% | 0.397 | 33% | 158% | 0.401 | 33% | 155% |
| 0.8-1 | R | 0.124 | | 48% | 0.122 | | 48% | 0.13 | | 52% | 0.131 | | 51% |
| 0-0.9 | NR | 0.415 | 30% | 162% | 0.381 | 28% | 150% | 0.361 | 38% | 144% | 0.381 | 32% | 148% |
| 0.9-1 | R | 0.126 | | 49% | 0.106 | | 42% | 0.136 | | 54% | 0.122 | | 47% |
| 0-0.1 | NR | 0.484 | 32% | 189% | 0.516 | 29% | 204% | 0.534 | 30% | 213% | 0.485 | 30% | 188% |
| 0.2-1 | R | 0.155 | | 60% | 0.15 | | 59% | 0.158 | | 63% | 0.147 | | 57% |
| 0.1-0.2 | UD | 0.563 | | 219% | 0.515 | | 203% | 0.335 | | 133% | 0.483 | | 187% |
| 0-0.1 | NR | 0.486 | 30% | 190% | 0.519 | 25% | 205% | 0.532 | 27% | 212% | 0.485 | 30% | 188% |
| 0.3-1 | R | 0.148 | | 58% | 0.13 | | 51% | 0.145 | | 58% | 0.144 | | 56% |
| 0.1-0.3 | UD | 0.402 | | 157% | 0.506 | | 200% | 0.353 | | 140% | 0.375 | | 145% |
| 0-0.1 | NR | 0.487 | 30% | 190% | 0.518 | 25% | 204% | 0.532 | 26% | 212% | 0.486 | 30% | 188% |
| 0.4-1 | R | 0.144 | | 56% | 0.13 | | 51% | 0.14 | | 56% | 0.146 | | 56% |
| 0.1-0.4 | UD | 0.355 | | 138% | 0.407 | | 161% | 0.342 | | 136% | 0.3 | | 116% |
| 0-0.1 | NR | 0.487 | 29% | 190% | 0.519 | 25% | 205% | 0.532 | 27% | 212% | 0.485 | 28% | 188% |
| 0.5-1 | R | 0.143 | | 56% | 0.132 | | 52% | 0.141 | | 56% | 0.138 | | 54% |
| 0.1-0.5 | UD | 0.318 | | 124% | 0.359 | | 142% | 0.309 | | 123% | 0.307 | | 119% |
| 0-0.1 | NR | 0.487 | 27% | 190% | 0.518 | 24% | 204% | 0.533 | 24% | 212% | 0.487 | 27% | 189% |
| 0.6-1 | R | 0.133 | | 52% | 0.126 | | 50% | 0.126 | | 50% | 0.132 | | 51% |
| 0.1-0.6 | UD | 0.361 | | 141% | 0.332 | | 131% | 0.319 | | 127% | 0.301 | | 117% |
| 0-0.1 | NR | 0.488 | 26% | 190% | 0.517 | 25% | 204% | 0.534 | 24% | 213% | 0.486 | 27% | 188% |

TABLE 37d-continued

Models GM2068, GM2090, GM2094 and GM2277.

| | | Model: | | | | | | | | | | |
|---|---|---|---|---|---|---|---|---|---|---|---|---|
| | | GM2068 | | | GM2090 | | | GM2094 | | | GM2277 | | |
| threshold | response prediction | ARR | Risk Ratio | ARR Vs. all | ARR | Risk Ratio | ARR Vs. all | ARR | Risk Ratio | ARR Vs. all | ARR | Risk Ratio | ARR Vs. all |
| 0.7-1 | R | 0.128 | | 50% | 0.128 | | 50% | 0.128 | | 51% | 0.129 | | 50% |
| 0.1-0.7 | UD | 0.348 | | 136% | 0.303 | | 120% | 0.293 | | 117% | 0.291 | | 113% |
| 0-0.1 | NR | 0.487 | 25% | 190% | 0.517 | 24% | 204% | 0.535 | 25% | 213% | 0.486 | 27% | 188% |
| 0.8-1 | R | 0.124 | | 48% | 0.122 | | 48% | 0.132 | | 52% | 0.131 | | 51% |
| 0.1-0.8 | UD | 0.324 | | 126% | 0.279 | | 110% | 0.262 | | 104% | 0.263 | | 102% |
| 0-0.1 | NR | 0.488 | 26% | 190% | 0.517 | 21% | 204% | 0.535 | 26% | 213% | 0.486 | 25% | 188% |
| 0.9-1 | R | 0.126 | | 49% | 0.106 | | 42% | 0.138 | | 55% | 0.122 | | 47% |
| 0.1-0.9 | UD | 0.289 | | 113% | 0.274 | | 108% | 0.224 | | 89% | 0.25 | | 97% |
| 0-0.2 | NR | 0.489 | 30% | 191% | 0.519 | 25% | 205% | 0.495 | 29% | 197% | 0.484 | 30% | 188% |
| 0.3-1 | R | 0.148 | | 58% | 0.13 | | 51% | 0.144 | | 57% | 0.144 | | 56% |
| 0.2-0.3 | UD | 0.311 | | 121% | 0.492 | | 194% | 0.374 | | 149% | 0.226 | | 88% |
| 0-0.2 | NR | 0.49 | 29% | 191% | 0.518 | 25% | 204% | 0.495 | 28% | 197% | 0.484 | 30% | 188% |
| 0.4-1 | R | 0.144 | | 56% | 0.13 | | 51% | 0.14 | | 56% | 0.146 | | 57% |
| 0.2-0.4 | UD | 0.287 | | 112% | 0.336 | | 132% | 0.348 | | 139% | 0.163 | | 63% |
| 0-0.2 | NR | 0.49 | 29% | 191% | 0.519 | 25% | 205% | 0.495 | 28% | 197% | 0.484 | 29% | 188% |
| -1 0.5 | R | 0.143 | | 56% | 0.132 | | 52% | 0.14 | | 56% | 0.139 | | 54% |
| 0.2-0.5 | UD | 0.26 | | 102% | 0.279 | | 110% | 0.292 | | 116% | 0.219 | | 85% |
| 0-0.2 | NR | 0.49 | 27% | 191% | 0.518 | 24% | 205% | 0.495 | 25% | 197% | 0.485 | 27% | 188% |
| 0.6-1 | R | 0.133 | | 52% | 0.126 | | 50% | 0.126 | | 50% | 0.132 | | 51% |
| 0.2-0.6 | UD | 0.319 | | 124% | 0.264 | | 104% | 0.311 | | 124% | 0.236 | | 91% |
| 0-0.2 | NR | 0.49 | 26% | 191% | 0.518 | 25% | 204% | 0.495 | 26% | 197% | 0.484 | 27% | 188% |
| 0.7-1 | R | 0.128 | | 50% | 0.128 | | 50% | 0.127 | | 51% | 0.129 | | 50% |
| 0.2-0.7 | UD | 0.312 | | 122% | 0.237 | | 94% | 0.278 | | 111% | 0.233 | | 90% |
| 0-0.2 | NR | 0.49 | 25% | 191% | 0.518 | 24% | 204% | 0.495 | 26% | 197% | 0.484 | 27% | 188% |
| 0.8-1 | R | 0.124 | | 48% | 0.122 | | 48% | 0.131 | | 52% | 0.131 | | 51% |
| 0.2-0.8 | UD | 0.292 | | 114% | 0.224 | | 88% | 0.239 | | 95% | 0.207 | | 80% |
| 0-0.2 | NR | 0.49 | 26% | 191% | 0.518 | 20% | 204% | 0.495 | 28% | 197% | 0.484 | 25% | 188% |
| 0.9-1 | R | 0.126 | | 49% | 0.106 | | 42% | 0.138 | | 55% | 0.122 | | 47% |
| 0.2-0.9 | UD | 0.259 | | 101% | 0.231 | | 91% | 0.199 | | 79% | 0.208 | | 81% |
| 0-0.3 | NR | 0.474 | 30% | 185% | 0.516 | 25% | 203% | 0.479 | 29% | 191% | 0.465 | 31% | 180% |
| 0.4-1 | R | 0.144 | | 56% | 0.13 | | 51% | 0.139 | | 56% | 0.146 | | 56% |
| 0.3-0.4 | UD | 0.254 | | 99% | 0.123 | | 49% | 0.293 | | 117% | 0.088 | | 34% |
| 0-0.3 | NR | 0.474 | 30% | 185% | 0.515 | 26% | 203% | 0.479 | 29% | 191% | 0.465 | 30% | 180% |
| 0.5-1 | R | 0.143 | | 56% | 0.132 | | 52% | 0.14 | | 56% | 0.138 | | 54% |
| 0.3-0.5 | UD | 0.224 | | 87% | 0.108 | | 43% | 0.203 | | 81% | 0.215 | | 83% |
| 0-0.3 | NR | 0.475 | 28% | 185% | 0.516 | 25% | 203% | 0.479 | 26% | 191% | 0.465 | 28% | 180% |
| 0.6-1 | R | 0.133 | | 52% | 0.127 | | 50% | 0.126 | | 50% | 0.132 | | 51% |
| 0.3-0.6 | UD | 0.323 | | 126% | 0.154 | | 61% | 0.279 | | 111% | 0.238 | | 92% |
| 0-0.3 | NR | 0.475 | 27% | 185% | 0.516 | 25% | 203% | 0.479 | 27% | 191% | 0.465 | 28% | 180% |
| 0.7-1 | R | 0.128 | | 50% | 0.128 | | 51% | 0.127 | | 51% | 0.129 | | 50% |
| 0.3-0.7 | UD | 0.312 | | 121% | 0.139 | | 55% | 0.239 | | 95% | 0.234 | | 91% |
| 0-0.3 | NR | 0.475 | 26% | 185% | 0.516 | 24% | 204% | 0.479 | 27% | 191% | 0.465 | 28% | 180% |
| 0.8-1 | R | 0.124 | | 48% | 0.123 | | 48% | 0.131 | | 52% | 0.131 | | 51% |
| 0.3-0.8 | UD | 0.286 | | 112% | 0.154 | | 61% | 0.198 | | 79% | 0.202 | | 78% |
| 0-0.3 | NR | 0.475 | 27% | 185% | 0.516 | 21% | 204% | 0.479 | 29% | 191% | 0.465 | 26% | 180% |
| 0.9-1 | R | 0.126 | | 49% | 0.106 | | 42% | 0.137 | | 55% | 0.122 | | 47% |
| 0.3-0.9 | UD | 0.246 | | 96% | 0.182 | | 72% | 0.161 | | 64% | 0.205 | | 79% |
| 0-0.3 | NR | 0.461 | 31% | 180% | 0.482 | 27% | 190% | 0.469 | 30% | 187% | 0.443 | 31% | 172% |
| 0.5-1 | R | 0.143 | | 56% | 0.132 | | 52% | 0.14 | | 56% | 0.138 | | 53% |
| 0.4-0.5 | UD | 0.191 | | 74% | 0.086 | | 34% | 0.106 | | 42% | 0.332 | | 129% |
| 0-0.4 | NR | 0.461 | 29% | 180% | 0.483 | 26% | 190% | 0.469 | 27% | 187% | 0.444 | 30% | 172% |
| 0.6-1 | R | 0.133 | | 52% | 0.126 | | 50% | 0.126 | | 50% | 0.131 | | 51% |
| 0.4-0.6 | UD | 0.373 | | 146% | 0.17 | | 67% | 0.275 | | 109% | 0.301 | | 117% |
| 0-0.4 | NR | 0.462 | 28% | 180% | 0.482 | 27% | 190% | 0.469 | 27% | 187% | 0.444 | 29% | 172% |
| 0.7-1 | R | 0.128 | | 50% | 0.128 | | 51% | 0.127 | | 51% | 0.129 | | 50% |
| 0.4-0.7 | UD | 0.337 | | 131% | 0.145 | | 57% | 0.227 | | 90% | 0.279 | | 108% |
| 0-0.4 | NR | 0.462 | 27% | 180% | 0.483 | 25% | 190% | 0.469 | 28% | 187% | 0.443 | 30% | 172% |
| 0.8-1 | R | 0.124 | | 48% | 0.123 | | 48% | 0.131 | | 52% | 0.131 | | 51% |
| 0.4-0.8 | UD | 0.296 | | 115% | 0.161 | | 64% | 0.182 | | 72% | 0.228 | | 88% |
| 0-0.4 | NR | 0.462 | 27% | 180% | 0.483 | 22% | 190% | 0.469 | 29% | 187% | 0.443 | 28% | 172% |
| 0.9-1 | R | 0.126 | | 49% | 0.106 | | 42% | 0.137 | | 55% | 0.122 | | 47% |
| 0.4-0.9 | UD | 0.244 | | 95% | 0.191 | | 75% | 0.146 | | 58% | 0.221 | | 86% |
| 0-0.5 | NR | 0.447 | 30% | 174% | 0.461 | 28% | 182% | 0.45 | 28% | 179% | 0.437 | 30% | 169% |
| 0.6-1 | R | 0.133 | | 52% | 0.127 | | 50% | 0.125 | | 50% | 0.131 | | 51% |
| 0.5-0.6 | UD | 0.71 | | 277% | 0.224 | | 88% | 0.343 | | 137% | 0.275 | | 106% |
| 0-0.5 | NR | 0.448 | 29% | 175% | 0.461 | 28% | 182% | 0.45 | 28% | 179% | 0.437 | 30% | 169% |
| 0.7-1 | R | 0.128 | | 50% | 0.128 | | 51% | 0.127 | | 50% | 0.129 | | 50% |
| 0.5-0.7 | UD | 0.431 | | 168% | 0.168 | | 66% | 0.259 | | 103% | 0.252 | | 98% |
| 0-0.5 | NR | 0.448 | 28% | 175% | 0.462 | 27% | 182% | 0.45 | 29% | 179% | 0.437 | 30% | 169% |
| 0.8-1 | R | 0.124 | | 48% | 0.123 | | 48% | 0.13 | | 52% | 0.131 | | 51% |
| 0.5-0.8 | UD | 0.332 | | 129% | 0.177 | | 70% | 0.195 | | 78% | 0.194 | | 75% |

TABLE 37d-continued

Models GM2068, GM2090, GM2094 and GM2277.

| | | Model: | | | | | | | | | | |
|---|---|---|---|---|---|---|---|---|---|---|---|---|
| | | GM2068 | | | GM2090 | | | GM2094 | | | GM2277 | | |
| threshold | response prediction | ARR | Risk Ratio | ARR Vs. all | ARR | Risk Ratio | ARR Vs. all | ARR | Risk Ratio | ARR Vs. all | ARR | Risk Ratio | ARR Vs. all |
| 0-0.5 | NR | 0.448 | 28% | 175% | 0.462 | 23% | 182% | 0.45 | 30% | 179% | 0.436 | 28% | 169% |
| 0.9-1 | R | 0.126 | | 49% | 0.106 | | 42% | 0.137 | | 55% | 0.122 | | 47% |
| 0.5-0.9 | UD | 0.257 | | 100% | 0.204 | | 81% | 0.15 | | 60% | 0.2 | | 78% |
| 0-0.6 | NR | 0.455 | 28% | 177% | 0.441 | 29% | 174% | 0.439 | 29% | 175% | 0.427 | 30% | 166% |
| 0.7-1 | R | 0.128 | | 50% | 0.128 | | 50% | 0.127 | | 51% | 0.129 | | 50% |
| 0.6-0.7 | UD | 0.28 | | 109% | 0.085 | | 33% | 0.088 | | 35% | 0.216 | | 84% |
| 0-0.6 | NR | 0.455 | 27% | 177% | 0.441 | 28% | 174% | 0.439 | 30% | 175% | 0.427 | 31% | 166% |
| 0.8-1 | R | 0.124 | | 48% | 0.122 | | 48% | 0.131 | | 52% | 0.131 | | 51% |
| 0.6-0.8 | UD | 0.244 | | 95% | 0.154 | | 61% | 0.072 | | 29% | 0.139 | | 54% |
| 0-0.6 | NR | 0.455 | 28% | 177% | 0.441 | 24% | 174% | 0.439 | 31% | 175% | 0.427 | 29% | 166% |
| 0.9-1 | R | 0.126 | | 49% | 0.106 | | 42% | 0.137 | | 55% | 0.122 | | 47% |
| 0.6-0.9 | UD | 0.188 | | 73% | 0.199 | | 78% | 0.071 | | 28% | 0.179 | | 69% |
| 0-0.7 | NR | 0.447 | 28% | 174% | 0.422 | 29% | 166% | 0.421 | 31% | 168% | 0.419 | 31% | 162% |
| 0.8-1 | R | 0.124 | | 48% | 0.122 | | 48% | 0.13 | | 52% | 0.131 | | 51% |
| 0.7-0.8 | UD | 0.217 | | 84% | 0.184 | | 72% | 0.061 | | 24% | 0.082 | | 32% |
| 0-0.7 | NR | 0.447 | 28% | 174% | 0.422 | 25% | 167% | 0.422 | 32% | 168% | 0.419 | 29% | 162% |
| 0.9-1 | R | 0.126 | | 49% | 0.105 | | 42% | 0.137 | | 55% | 0.122 | | 47% |
| 0.7-0.9 | UD | 0.151 | | 59% | 0.221 | | 87% | 0.067 | | 26% | 0.171 | | 66% |
| 0-0.8 | NR | 0.433 | 29% | 169% | 0.398 | 27% | 157% | 0.397 | 35% | 158% | 0.401 | 30% | 155% |
| 0.9-1 | R | 0.126 | | 49% | 0.106 | | 42% | 0.137 | | 55% | 0.122 | | 47% |
| 0.8-0.9 | UD | 0.079 | | 31% | 0.253 | | 100% | 0.069 | | 28% | 0.208 | | 81% |

TABLE 37e

Models GM2338, GM3102, GM3150 and GM3332.

| Model: | | GM2338 | | | GM3102 | | | GM3150 | | | GM3332 | | |
|---|---|---|---|---|---|---|---|---|---|---|---|---|---|
| threshold | response prediction | ARR | Risk Ratio | ARR Vs. all | ARR | Risk Ratio | ARR Vs. all | ARR | Risk Ratio | ARR Vs. all | ARR | Risk Ratio | ARR Vs. all |
| NA | All | 0.251 | | 100% | 0.263 | | 100% | 0.26 | | 100% | 0.262 | | 100% |
| 0-0.1 | NR | 0.662 | | 264% | 0.605 | | 230% | 0.584 | | 225% | 0.612 | | 234% |
| 0.1-1 | R | 0.163 | 25% | 65% | 0.167 | 28% | 63% | 0.163 | 28% | 63% | 0.183 | 30% | 70% |
| 0-0.2 | NR | 0.616 | | 246% | 0.588 | | 224% | 0.512 | | 197% | 0.523 | | 200% |
| 0.2-1 | R | 0.155 | 25% | 62% | 0.146 | 25% | 55% | 0.162 | 32% | 62% | 0.168 | 32% | 64% |
| 0-0.3 | NR | 0.537 | | 214% | 0.564 | | 215% | 0.503 | | 194% | 0.535 | | 204% |
| 0.3-1 | R | 0.156 | 29% | 62% | 0.136 | 24% | 52% | 0.152 | 30% | 59% | 0.14 | 26% | 54% |
| 0-0.4 | NR | 0.488 | | 195% | 0.531 | | 202% | 0.474 | | 182% | 0.51 | | 195% |
| 0.4-1 | R | 0.154 | 32% | 61% | 0.136 | 26% | 52% | 0.149 | 31% | 57% | 0.141 | 28% | 54% |
| 0-0.5 | NR | 0.467 | | 186% | 0.506 | | 193% | 0.45 | | 173% | 0.502 | | 192% |
| 0.5-1 | R | 0.152 | 33% | 61% | 0.131 | 26% | 50% | 0.146 | 32% | 56% | 0.13 | 26% | 50% |
| 0-0.6 | NR | 0.436 | | 174% | 0.483 | | 184% | 0.426 | | 164% | 0.486 | | 186% |
| 0.6-1 | R | 0.15 | 34% | 60% | 0.135 | 28% | 51% | 0.143 | 34% | 55% | 0.123 | 25% | 47% |
| 0-0.7 | NR | 0.439 | | 175% | 0.457 | | 174% | 0.432 | | 166% | 0.461 | | 176% |
| 0.7-1 | R | 0.136 | 31% | 54% | 0.128 | 28% | 49% | 0.122 | 28% | 47% | 0.122 | 26% | 47% |
| 0-0.8 | NR | 0.417 | | 166% | 0.432 | | 164% | 0.4 | | 154% | 0.446 | | 170% |
| 0.8-1 | R | 0.134 | 32% | 53% | 0.124 | 29% | 47% | 0.119 | 30% | 46% | 0.117 | 26% | 45% |
| 0-0.9 | NR | 0.402 | | 160% | 0.384 | | 146% | 0.362 | | 139% | 0.41 | | 156% |
| 0.9-1 | R | 0.117 | 29% | 47% | 0.13 | 34% | 49% | 0.127 | 35% | 49% | 0.115 | 28% | 44% |
| 0-0.1 | NR | 0.661 | | 264% | 0.611 | | 233% | 0.584 | | 225% | 0.587 | | 224% |
| 0.2-1 | R | 0.156 | 24% | 62% | 0.145 | 24% | 55% | 0.162 | 28% | 63% | 0.169 | 29% | 64% |
| 0.1-0.2 | UD | 0.355 | | 142% | 0.479 | | 182% | 0.166 | | 64% | 0.281 | | 107% |
| 0-0.1 | NR | 0.662 | | 264% | 0.609 | | 232% | 0.583 | | 225% | 0.583 | | 223% |
| 0.3-1 | R | 0.157 | 24% | 63% | 0.136 | 22% | 52% | 0.153 | 26% | 59% | 0.141 | 24% | 54% |
| 0.1-0.3 | UD | 0.229 | | 91% | 0.436 | | 166% | 0.252 | | 97% | 0.431 | | 165% |
| 0-0.1 | NR | 0.663 | | 264% | 0.609 | | 232% | 0.584 | | 225% | 0.581 | | 222% |
| 0.4-1 | R | 0.154 | 23% | 62% | 0.136 | 22% | 52% | 0.15 | 26% | 58% | 0.141 | 24% | 54% |
| 0.1-0.4 | UD | 0.219 | | 87% | 0.362 | | 138% | 0.239 | | 92% | 0.383 | | 146% |
| 0-0.1 | NR | 0.663 | | 265% | 0.609 | | 231% | 0.584 | | 225% | 0.578 | | 221% |
| 0.5-1 | R | 0.152 | 23% | 61% | 0.132 | 22% | 50% | 0.148 | 25% | 57% | 0.131 | 23% | 50% |
| 0.1-0.5 | UD | 0.217 | | 87% | 0.338 | | 129% | 0.23 | | 89% | 0.39 | | 149% |
| 0-0.1 | NR | 0.664 | | 265% | 0.607 | | 231% | 0.584 | | 225% | 0.577 | | 220% |
| 0.6-1 | R | 0.15 | 23% | 60% | 0.135 | 22% | 51% | 0.144 | 25% | 55% | 0.124 | 21% | 47% |
| 0.1-0.6 | UD | 0.21 | | 84% | 0.299 | | 114% | 0.223 | | 86% | 0.373 | | 142% |
| 0-0.1 | NR | 0.665 | | 265% | 0.609 | | 232% | 0.584 | | 225% | 0.578 | | 221% |
| 0.7-1 | R | 0.136 | 20% | 54% | 0.128 | 21% | 49% | 0.123 | 21% | 47% | 0.123 | 21% | 47% |
| 0.1-0.7 | UD | 0.245 | | 98% | 0.283 | | 108% | 0.267 | | 103% | 0.337 | | 129% |

TABLE 37e-continued

Models GM2338, GM3102, GM3150 and GM3332.

| Model: | | GM2338 | | | GM3102 | | | GM3150 | | | GM3332 | | |
|---|---|---|---|---|---|---|---|---|---|---|---|---|---|
| threshold | response prediction | ARR | Risk Ratio | ARR Vs. all | ARR | Risk Ratio | ARR Vs. all | ARR | Risk Ratio | ARR Vs. all | ARR | Risk Ratio | ARR Vs. all |
| 0-0.1 | NR | 0.664 | | 265% | 0.607 | | 231% | 0.583 | | 225% | 0.579 | | 221% |
| 0.8-1 | R | 0.134 | 20% | 54% | 0.125 | 21% | 48% | 0.12 | 21% | 46% | 0.119 | 21% | 45% |
| 0.1-0.8 | UD | 0.234 | | 93% | 0.264 | | 101% | 0.242 | | 93% | 0.323 | | 123% |
| 0-0.1 | NR | 0.665 | | 265% | 0.606 | | 231% | 0.583 | | 225% | 0.581 | | 222% |
| 0.9-1 | R | 0.117 | 18% | 47% | 0.131 | 22% | 50% | 0.129 | 22% | 50% | 0.117 | 20% | 45% |
| 0.1-0.9 | UD | 0.246 | | 98% | 0.222 | | 85% | 0.208 | | 80% | 0.284 | | 108% |
| 0-0.2 | NR | 0.616 | | 246% | 0.587 | | 223% | 0.51 | | 196% | 0.516 | | 197% |
| 0.3-1 | R | 0.156 | 25% | 62% | 0.137 | 23% | 52% | 0.152 | 30% | 59% | 0.14 | 27% | 54% |
| 0.2-0.3 | UD | 0.134 | | 54% | 0.363 | | 138% | 0.43 | | 166% | 0.65 | | 248% |
| 0-0.2 | NR | 0.616 | | 246% | 0.588 | | 224% | 0.512 | | 197% | 0.515 | | 197% |
| 0.4-1 | R | 0.154 | 25% | 61% | 0.136 | 23% | 52% | 0.149 | 29% | 58%. | 0.141 | 27% | 54% |
| 0.2-0.4 | UD | 0.169 | | 68% | 0.258 | | 98% | 0.296 | | 114% | 0.487 | | 186% |
| 0-0.2 | NR | 0.616 | | 246% | 0.586 | | 223% | 0.511 | | 197% | 0.512 | | 196% |
| -10.5 | R | 0.152 | 25% | 60% | 0.132 | 23% | 50% | 0.147 | 29% | 57% | 0.13 | 25% | 50% |
| 0.2-0.5 | UD | 0.178 | | 71% | 0.253 | | 96% | 0.263 | | 101% | 0.471 | | 180% |
| 0-0.2 | NR | 0.617 | | 246% | 0.587 | | 224% | 0.512 | | 197% | 0.512 | | 196% |
| 0.6-1 | R | 0.15 | 24% | 60% | 0.136 | 23% | 52% | 0.144 | 28% | 55% | 0.123 | 24% | 47% |
| 0.2-0.6 | UD | 0.179 | | 71% | 0.208 | | 79% | 0.243 | | 94% | 0.424 | | 162% |
| 0-0.2 | NR | 0.618 | | 247% | 0.588 | | 224% | 0.512 | | 197% | 0.514 | | 196% |
| 0.7-1 | R | 0.136 | 22% | 54% | 0.129 | 22% | 49% | 0.122 | 24% | 47% | 0.123 | 24% | 47% |
| 0.2-0.7 | UD | 0.224 | | 89% | 0.215 | | 82% | 0.295 | | 114% | 0.362 | | 138% |
| 0-0.2 | NR | 0.618 | | 246% | 0.588 | | 224% | 0.511 | | 197% | 0.516 | | 197% |
| 0.8-1 | R | 0.134 | 22% | 53% | 0.126 | 21% | 48% | 0.12 | 23% | 46% | 0.118 | 23% | 45% |
| 0.2-0.8 | UD | 0.215 | | 86% | 0.205 | | 78% | 0.258 | | 99% | 0.338 | | 129% |
| 0-0.2 | NR | 0.619 | | 247% | 0.588 | | 224% | 0.511 | | 197% | 0.518 | | 198% |
| 0.9-1 | R | 0.117 | 19% | 47% | 0.132 | 22% | 50% | 0.128 | 25% | 49% | 0.117 | 23% | 45% |
| 0.2-0.9 | UD | 0.232 | | 92% | 0.171 | | 65% | 0.214 | | 83% | 0.285 | | 109% |
| 0-0.3 | N | 0.537 | | 214% | 0.564 | | 215% | 0.504 | | 194% | 0.535 | | 204% |
| 0.4-1 | R | 0.153 | 28% | 61% | 0.136 | 24% | 52% | 0.149 | 30% | 57% | 0.141 | 26% | 54% |
| 0.3-0.4 | UD | 0.199 | | 80% | 0.148 | | 56% | 0.212 | | 82% | 0.114 | | 44% |
| 0-0.3 | NR | 0.538 | | 215% | 0.564 | | 215% | 0.503 | | 194% | 0.532 | | 203% |
| 0.5-1 | R | 0.151 | 28% | 60% | 0.132 | 23% | 50% | 0.147 | 29% | 56% | 0.131 | 25% | 50% |
| 0.3-0.5 | UD | 0.201 | | 80% | 0.194 | | 74% | 0.205 | | 79% | 0.293 | | 112% |
| 0-0.3 | NR | 0.538 | | 215% | 0.564 | | 215% | 0.504 | | 194% | 0.531 | | 203% |
| 0.6-1 | R | 0.15 | 28% | 60% | 0.135 | 24% | 52% | 0.143 | 28% | 55% | 0.124 | 23% | 47% |
| 0.3-0.6 | UD | 0.194 | | 77% | 0.145 | | 55% | 0.202 | | 78% | 0.291 | | 111% |
| 0-0.3 | NR | 0.539 | | 215% | 0.565 | | 215% | 0.504 | | 194% | 0.532 | | 203% |
| 0.7-1 | R | 0.135 | 25% | 54% | 0.128 | 23% | 49% | 0.122 | 24% | 47% | 0.123 | 23% | 47% |
| 0.3-0.7 | UD | 0.25 | | 100% | 0.178 | | 68% | 0.272 | | 105% | 0.244 | | 93% |
| 0-0.3 | NR | 0.539 | | 215% | 0.564 | | 215% | 0.503 | | 194% | 0.532 | | 203% |
| 0.8-1 | R | 0.134 | 25% | 53% | 0.125 | 22% | 48% | 0.12 | 24% | 46% | 0.119 | 22% | 45% |
| 0.3-0.8 | UD | 0.233 | | 93% | 0.175 | | 67% | 0.237 | | 91% | 0.239 | | 91% |
| 0-0.3 | NR | 0.54 | | 215% | 0.564 | | 215% | 0.503 | | 194% | 0.533 | | 204% |
| 0.9-1 | R | 0.117 | 22% | 46% | 0.131 | 23% | 50% | 0.128 | 25% | 49% | 0.117 | 22% | 45% |
| 0.3-0.9 | UD | 0.248 | | 99% | 0.147 | | 56% | 0.194 | | 75% | 0.206 | | 79% |
| 0-0.3 | NR | 0.489 | | 195% | 0.529 | | 202% | 0.474 | | 182% | 0.508 | | 194% |
| 0.5-1 | R | 0.152 | 31% | 61% | 0.131 | 25% | 50% | 0.147 | 31% | 57% | 0.13 | 26% | 50% |
| 0.4-0.5 | UD | 0.204 | | 81% | 0.243 | | 93% | 0.198 | | 76% | 0.426 | | 163% |
| 0-0.4 | NR | 0.489 | | 195% | 0.531 | | 202% | 0.474 | | 182% | 0.507 | | 194% |
| 0.6-1 | R | 0.15 | 31% | 60% | 0.135 | 25% | 51% | 0.143 | 30% | 55% | 0.123 | 24% | 47% |
| 0.4-0.6 | UD | 0.191 | | 76% | 0.142 | | 54% | 0.197 | | 76% | 0.351 | | 134% |
| 0-0.4 | NR | 0.49 | | 196% | 0.531 | | 202% | 0.473 | | 182% | 0.508 | | 194% |
| 0.7-1 | R | 0.136 | 28% | 54% | 0.128 | 24% | 49% | 0.122 | 26% | 47% | 0.123 | 24% | 47% |
| 0.4-0.7 | UD | 0.274 | | 109% | 0.186 | | 71% | 0.295 | | 113% | 0.272 | | 104% |
| 0-0.4 | NR | 0.49 | | 195% | 0.53 | | 202% | 0.473 | | 182% | 0.509 | | 194% |
| 0.8-1 | R | 0.134 | 27% | 53% | 0.125 | 24% | 48% | 0.12 | 25% | 46% | 0.118 | 23% | 45% |
| 0.4-0.8 | UD | 0.245 | | 98% | 0.18 | | 69% | 0.243 | | 94% | 0.258 | | 99% |
| 0-0.4 | NR | 0.49 | | 196% | 0.53 | | 202% | 0.473 | | 182% | 0.509 | | 194% |
| 0.9-1 | R | 0.117 | 24% | 47% | 0.131 | 25% | 50% | 0.128 | 27% | 49% | 0.116 | 23% | 44% |
| 0.4-0.9 | UD | 0.26 | | 104% | 0.146 | | 56% | 0.192 | | 74% | 0.215 | | 82% |
| 0-0.5 | NR | 0.467 | | 186% | 0.504 | | 192% | 0.45 | | 173% | 0.501 | | 192% |
| 0.6-1 | R | 0.15 | 32% | 60% | 0.134 | 27% | 51% | 0.143 | 32% | 55% | 0.123 | 25% | 47% |
| 0.5-0.6 | UD | 0.184 | | 73% | 0 | | 0% | 0.195 | | 75% | 0.287 | | 110% |
| 0-0.5 | NR | 0.468 | | 187% | 0.506 | | 193% | 0.45 | | 173% | 0.502 | | 192% |
| 0.7-1 | R | 0.136 | 29% | 54% | 0.127 | 25% | 49% | 0.122 | 27% | 47% | 0.122 | 24% | 47% |
| 0.5-0.7 | UD | 0.302 | | 120% | 0.161 | | 61% | 0.336 | | 129% | 0.209 | | 80% |
| 0-0.5 | NR | 0.467 | | 186% | 0.506 | | 193% | 0.45 | | 173% | 0.502 | | 192% |
| 0.8-1 | R | 0.134 | 29% | 54% | 0.125 | 25% | 47% | 0.119 | 26% | 46% | 0.118 | 24% | 45% |
| 0.5-0.8 | UD | 0.256 | | 102% | 0.164 | | 62% | 0.254 | | 98% | 0.212 | | 81% |
| 0-0.5 | NR | 0.468 | | 187% | 0.506 | | 193% | 0.45 | | 173% | 0.502 | | 192% |
| 0.9-1 | R | 0.117 | 25% | 47% | 0.131 | 26% | 50% | 0.128 | 28% | 49% | 0.116 | 23% | 44% |
| 0.5-0.9 | UD | 0.27 | | 108% | 0.131 | | 50% | 0.19 | | 73% | 0.18 | | 69% |
| 0-0.6 | NR | 0.436 | | 174% | 0.484 | | 184% | 0.426 | | 164% | 0.485 | | 185% |

TABLE 37e-continued

Models GM2338, GM3102, GM3150 and GM3332.

| Model: | | GM2338 | | | GM3102 | | | GM3150 | | | GM3332 | | |
|---|---|---|---|---|---|---|---|---|---|---|---|---|---|
| threshold | response prediction | ARR | Risk Ratio | ARR Vs. all | ARR | Risk Ratio | ARR Vs. all | ARR | Risk Ratio | ARR Vs. all | ARR | Risk Ratio | ARR Vs. all |
| 0.7-1 | R | 0.136 | 31% | 54% | 0.128 | 26% | 49% | 0.122 | 29% | 47% | 0.122 | 25% | 47% |
| 0.6-0.7 | UD | 0.474 | | 189% | 0.227 | | 86% | 0.519 | | 200% | 0.135 | | 52% |
| 0-0.6 | NR | 0.436 | | 174% | 0.483 | | 184% | 0.425 | | 164% | 0.485 | | 185% |
| 0.8-1 | R | 0.134 | 31% | 54% | 0.125 | 26% | 48% | 0.119 | 28% | 46% | 0.117 | 24% | 45% |
| 0.6-0.8 | UD | 0.303 | | 121% | 0.2 | | 76% | 0.282 | | 108% | 0.174 | | 67% |
| 0-0.6 | NR | 0.437 | | 174% | 0.483 | | 184% | 0.426 | | 164% | 0.505 | | 193% |
| 0.9-1 | R | 0.117 | 27% | 47% | 0.131 | 27% | 50% | 0.127 | 30% | 49% | 0.119 | 24% | 45% |
| 0.6-0.9 | UD | 0.299 | | 119% | 0.146 | | 56% | 0.189 | | 73% | 0.172 | | 66% |
| 0-0.7 | NR | 0.439 | | 175% | 0.457 | | 174% | 0.432 | | 166% | 0.461 | | 176% |
| 0.8-1 | R | 0.134 | 31% | 54% | 0.125 | 27% | 48% | 0.119 | 28% | 46% | 0.117 | 25% | 45% |
| 0.7-0.8 | UD | 0.164 | | 65% | 0.168 | | 64% | 0.147 | | 57% | 0.215 | | 82% |
| 0-0.7 | NR | 0.44 | | 175% | 0.457 | | 174% | 0.432 | | 166% | 0.461 | | 176% |
| 0.9-1 | R | 0.117 | 27% | 47% | 0.131 | 29% | 50% | 0.127 | 29% | 49% | 0.115 | 25% | 44% |
| 0.7-0.9 | UD | 0.246 | | 98% | 0.114 | | 43% | 0.102 | | 39% | 0.16 | | 61% |
| 0-0.8 | NR | 0.417 | | 166% | 0.431 | | 164% | 0.401 | | 154% | 0.446 | | 170% |
| 0.9-1 | R | 0.117 | 28% | 47% | 0.13 | 30% | 50% | 0.127 | 32% | 49% | 0.115 | 26% | 44% |
| 0.8-0.9 | UD | 0.294 | | 117% | 0.085 | | 33% | 0.063 | | 24% | 0.134 | | 51% |

DISCUSSION

Using GWAS, we have found SNPs having a predictive ability of GA response, which are presented in tables 1-3 or table 16. We have also created predictive models which predict with high accuracy the response to GA based on a certain set of SNPs from tables 1-3 or table 16. Other models can be created which use one or more SNPs from tables 1-3 or table 16 or combinations of one or more SNPs indicated in tables 1-3 or table 16 with clinical variables described in the application or others which can be contemplated by the person skilled in the art, in order to predict the response to GA. In addition, kits based on SNPs or models of the invention may be used in order to predict whether a patient is a responder or a non-responder to GA. Predicting whether a subject afflicted with multiple sclerosis or a single clinical attack consistent with multiple sclerosis is a responder to GA based on the determination of the patient's genotype at one or more SNP from table 1-3 or table 16 or a combination of SNPs indicated in tables 1-3 with clinical variables should assist in planning an effective treatment for patients afflicted with multiple sclerosis or a single clinical attack consistent with multiple sclerosis.

REFERENCES

1. Noseworthy J H, Lucchinetti C, Rodriguez M, Weinshenker B G. Multiple sclerosis. N Engl J Med 2000; 343:938-52.
2. Guideline on clinical investigation of medicinal products for the treatment of multiple sclerosis EMEA, London 16 Sep. 2006.
3, Bjartmar C, Fox R J. Pathological mechanisms and disease progression of multiple sclerosis: therapeutic implications. Drugs of Today 2002; 38:17-29.
4. Fleming J O. Diagnosis and management of multiple sclerosis. 1st ed. New York: Professional communications, Inc., 2002.
5. Anderson D W, Ellenberg J H, Leventhal C M et al. Revised estimate of the prevalence of multiple sclerosis in the United States, Ann Neurol 1992; 31:333-36.
6. Compston A, Lassmann H, McDonald I. The story of multiple sclerosis. In: Compston A. Confavreux C, Lassman H, Mcdonald I, Miller D, Noseworthy J H, Smith K, Wekerle H, editors. McAlpine's Multiple Sclerosis. London: Churchill Livingstone; 2006. p. 3-68.
7. Revel M., Pharmacol. Ther., 100(1):49-62 (2003).
8. Martinelli B F, Rovaris M, Johnson K P, Miller A, Wolinsky J S, Ladkani D, Shifroni G, Comi G, Filippi M. Effects of glatiramer acetate on relapse rate and accumulated disability in multiple sclerosis: meta-analysis of three double-blind, randomized, placebo-controlled clinical trials. Mult Scler. 2003 August; 9(4):349-55.
9. Mikol D D, Barkhof F, Chang P, Coyle P K, Jeffery D R, Schwid S R, Stubinski B, Uitdehaag B M; REGARD study group. Lancet Neurol. 2008 October; 7(10):903-14. Epub 2008 Sep. 11.
10. BECOME TRIAL, Presented at the 23rd Congress of the European Committee for Treatment and Research in Multiple Sclerosis (ECTRIMS) in Prague, Czech Republic.
11. Comi G, Filippi M and Wolinsky J S. European/Canadian multi-center, double-blind randomized, placebo controlled study of the effects of glatiramer acetate on magnetic resonance imaging-measured disease activity and burden in patients with relapsing-remitting multiple sclerosis. Ann Neurol 2001; (49):290-297.
12. Fridkis H M, Aharoni R, Teitelbaum D, Arnon R, Sela M, Strominger J L. Binding of random copolymers of three amino acids to class II MHC molecules. Int. Immunol. 1999 May; 11(5):635-41.
13, Dhib-Jalbut S S, Zhan M, Johnson K P, Martin R. Glatiramer acetate reactive blood mononuclear cells respond to myelin antigens with a Th-2 biased phenotype. J Neuroimmunology 2003; 140:163-171.
14. Chen M, Gran B, Costello K, Johnson K P, Martin R, Dhib-Jalbut S. Glatiramer acetate induces a Th-2 biased response and cross-reactivity with myelin basic protein in patients with MS. Multiple Sclerosis 2001; 7:209-219.
15. Weber M S, Prod'homme T, Youssef S, Dunn S E, Rundle C D, Lee L, Patarroyo J C, Stüve O, Sobel R A, Steinman L, Zamvil S S. Type II monocytes modulate T cell-mediated central nervous sytem autoimmune disease. Nat Med (2007) 13:935-943.
16. Aharoni R, Kayhan B, Eilam R, Sela M, and Amnon R. Glatiramer acetate-specific T cells in the brain express T helper 2/3 cytokines and brain-derived neurotrophic factor in situ. PNAS August 2003; 100(24):14157-62.
17. Sarchielli P. Zaffaroni M, Floridi A, Greco L, Candeliere A, Mattioni A, Tenaglia S, Di Filippo M, Calabresi P. Production of brain-derived neurotrophic factor by mononuclear cells of patients with multiple sclerosis treated with glatiramer acetate, interferon-beta 1a, and high doses of immunoglobulins. Mult Scler 2007 April; 13(3):313-31. Epub 2007 Jan. 29.
18. Bornstein, M B, Miller, A, Slagle, S, et al. A pilot trial of Cop 1 in exacerbating remitting multiple sclerosis. *New Eng J Med* 1987; 317: 408-14.
19, Comi, G, Fillippi, M, Wolinsky, J S, et al. European/Canadian multicenter, double-blind, randomized, placebo-controlled study of the effects of glatiramer acetate on magnetic resonance imagine-measured disease activity and burden in patients with relapsing multiple sclerosis. *Ann Neurol* 2001; 49: 290-7,
20. Johnson, K P, Brooks, B R, Cohen, J A, et al. Extended use of glatiramer acetate (Copaxone) is well tolerated and maintains its clinical effect on multiple sclerosis relapse rate and degree of disability. *Neurology* 1998; 50:701-8,
21. Bornstein, M B, Miller, A, Slagle, S. et al. A placebo-controlled, double-blind, randomized, two-center, pilot trial of Cop-1 in chronic progressive multiple sclerosis. *Neurology* 1991; 41: 533-39.
22. Wolinsky, J S, Narayana, P A, O'Conner, P. et al. Glatiramer acetate in primary progressive multiple sclerosis: Results of a multinational, multicenter, double-blind, placebo-controlled trial. *Ann Neurol* 2007; 61:14-24.
23. Comi G, Filippi M, Treatment with glatiramer acetate delays conversion to clinically definite multiple sclerosis (CDMS) in patients with clinically isolated syndromes (CIS). *Neurology* 2008; 71 (2): 153.
24, Tselis, A, Khan, O, Lisak, R P, Glatiramer acetate in the treatment of multiple sclerosis. *Neuropsychiatric Dis Treat* 2007; 3(2):259-67.
25. Wolinsky, J S, The use of glatiramer acetate in the treatment of multiple sclerosis. *Adv Neurol* 2006; 273-92.
26. Comi G, Cohen J A, Filippi M, Results from a phase III, one-year, randomized, double-blind, parallel-group, dose-comparison study with glatiramer acetate in relapsing-remitting multiple sclerosis. *Mult Scler* 2008; 14(suppl 1):S299.
27. Comi G, Filippi M. Presented at: 60th Annual Meeting of the American Academy of Neurology: April 12-19; Chicago, Ill. Abstract LBS.003.
28. Johnson D, Hafler D A, Fallis R J, Lees M B, Brady R O, Quarles R H, Weiner H L., "Cell-mediated immunity to myelin-associated glycoprotein, proteolipid protein, and myelin basic protein in multiple sclerosis.", *J Neuroimmunol.* 1986 November; 13 (1):99-108.
29. Brex P A et al., "A longitudinal study of abnormalities on MRI and disability from multiple sclerosis", *N Engl J Med* 2002 Jan. 17, 346(31:158-64.
30. Frohman E M et al., "The utility of MRI in suspected MS: report of the Therapeutics and Technology Assessment Subcommittee of the American Academy of Neurology", *Neurology,* 2003, September 9, 61(5):602-11.
31. Poser C M. et al. New diagnostic criteria for multiple sclerosis: Guidelines for research protocols. Ann. Neurol., 13(3): 227-31, 1983
32. Neurostatus, slightly modified from J. F. Kurtzke Neurology 1983:33, 1444-52; L. Kappos, Dept. of Neurology, University Hospital, CH-4031/Basel, Switzerland.
33. Farina C, Then Bergh F, Albrecht H, Meinl E, Yassouridis A, Neuhaus O, Hohlfeld R. Treatment of multiple sclerosis with Copaxone (COP): Elispot assay detects COP-induced interleukin-4 and interferon-gamma response in blood cells. Brain. 2001 April; 124(Pt 4):705-19.
34. U.S. Pat. No. 7,855,176, issued Dec. 21, 2010 (Altman et al.).
35. U.S. Patent Application Publication No. US 2011-0046065 A1, published Feb. 24, 2011 (Klinger).
36. Byun et al. "Genome-wide pharmacogenomic analysis of the response to interferon beta therapy in multiple sclerosis," Arch Neurol. 2008 March; 65(3):337-44. Epub 2008 Jan. 14.
37. Fusco, C. et al. "HLA-DRB1*1501 and response to copolymer-1 therapy in relapsing-remitting multiple sclerosis," Neurology. 2001 Dec. 11; 57(11)1976-9.
38. Grossman et al. "Pharmacogenetics of glatiramer acetate therapy for multiple sclerosis reveals drug-response markers," Pharmacogenet Genomics, 2007 August; 17(8):657-66,
39. PCT International Application Publication No. WO2006/116602, published Nov. 2, 2006 (Lancet et al).

What is claimed is:

1. A method for treating a human subject afflicted with multiple sclerosis or a single clinical attack consistent with multiple sclerosis with a pharmaceutical composition comprising glatiramer acetate and a pharmaceutically acceptable carrier, comprising the steps of:
   i. determining a genotype of the subject at the single nucleotide polymorphism (SNP) rs17771939,
   ii. identifying the subject as a predicted responder to glatiramer acetate if the genotype is
      TT at rs17771939; and
   iii. administering the pharmaceutical composition comprising glatiramer acetate and a pharmaceutically acceptable carrier to the subject only if the subject is identified as a predicted responder to glatiramer acetate.

2. The method of claim 1, wherein administering the pharmaceutical composition comprising glatiramer acetate and a pharmaceutically acceptable carrier comprises administering to the human subject three subcutaneous injections of the pharmaceutical composition over a period of seven days with at least one day between every subcutaneous injection.

3. The method of claim 2, wherein the pharmaceutical composition is a unit dose of a 1 ml aqueous solution comprising 40 mg of glatiramer acetate.

4. The method of claim 1, wherein the pharmaceutical composition is a unit dose of a 1 ml aqueous solution comprising 20 mg of glatiramer acetate.

5. The method of claim 1, wherein the pharmaceutical composition is a unit dose of a 0.5 ml aqueous solution comprising 20 mg of glatiramer acetate.

6. The method of claim 1, wherein the pharmaceutical composition comprising glatiramer acetate and a pharmaceutically acceptable carrier is administered as monotherapy.

7. The method of claim 1, wherein the pharmaceutical composition comprising glatiramer acetate and a pharmaceutically acceptable carrier is administered in combination with at least one other multiple sclerosis drug.

8. The method of claim 1, wherein the human subject is a naive patient.

9. The method of claim 1, wherein the human subject has been previously administered glatiramer acetate.

10. The method of claim 1, wherein the human subject has been previously administered a multiple sclerosis drug other than glatiramer acetate.

11. The method of claim 1, wherein the genotype of the subject at said one or more SNPs is obtained indirectly by determining the genotype of the subject at a SNP that is in linkage disequilibrium with said one or more SNPs.

12. The method of claim 1, wherein step i. further comprises determining a genotype of the subject at one or more single nucleotide polymorphisms (SNPs) selected from the group consisting of: rs1007328, rs10083547, rs10136012, rs10214633, rs10277267, rs1040194, rs1041897, rs10853605, rs10931091, rs10935015, rs10935016, rs10935019, rs10950359, rs10950371, rs10988087, rs11009827, rs11009835, rs11081859, rs11599624, rs11617134, rs11618546, rs11694344, rs11709339, rs11719825, rs11761457, rs11907046, rs12055694, rs12256889, rs1229542, rs1229553, rs1229555, rs1229558, rs1229562, rs1229563, rs1229564, rs1229568, rs12340584, rs1234567, rs1234947, rs1237625, rs12488259, rs12494606, rs12496278, rs12524041, rs12529764, rs12532459, rs12540494, rs12593600, rs12633010, rs12637073, rs12639443, rs1264423, rs1282540, rs1282546, rs12968586, rs1299325, rs13021482, rs13042992, rs1320648, rs13238613, rs13245980, rs1415557, rs1538123, rs1573706, rs1591661, rs1611185, rs1683691, rs16999008, rs17007730, rs17087180, rs17104665, rs17104742, rs17134651, rs17575455, rs17588454, rs17666347, rs17807327, rs17807445, rs1886308, rs1892974, rs1941973, rs2033471, rs2088713, rs214526, rs2155262, rs2177073, rs2187495, rs2277431, rs2305623, rs2374730, rs2461319, rs2487889, rs2487896, rs2508806, rs2511064, rs2521643, rs2521644, rs2530121, rs2530123, rs2685484, rs2722396, rs2722398, rs28861531, rs2895215, rs2937395, rs3135391, rs35831078, rs3742228, rs401618, rs4148871, rs4255033, rs4281882, rs4289164, rs4306478, rs4343256, rs4344916, rs4369324, rs4435429, rs4445746, rs4466940, rs4468448, rs4483642, rs4565951, rs4578835, rs4634524, rs4799760, rs4809955, rs4811492, rs496486, rs552994, rs6015147, rs6025923, rs6025927, rs6091820, rs6097782, rs6097790, rs6097793, rs6097797, rs6097801, rs6123749, rs6543934, rs6558102, rs656975, rs657302, rs6584894, rs660075, rs6713772, rs6909321, rs6971202, rs702355, rs7080507, rs7086707, rs7093143, rs7178587, rs7180867, rs7232734, rs7238006, rs7244801, rs7317000, rs751370, rs752979, rs7619350, rs7633210, rs7714122, rs7789703, rs7803164, rs7806265, rs7916897, rs7955917, rs7963693, rs8099595, rs8118441, rs844602, rs844608, rs844610, rs844612, rs844626, rs860722, rs873216, rs884266, rs894857, rs913882, rs9315048, rs9332420, rs933863, rs933864, rs9378319, rs9378684, rs9392358, rs9405541, rs9405546, rs947603, rs948029, rs948032, rs949298, rs9508834, rs9944913, rs9952995, and rs998051, and wherein step ii. further comprises identifying the subject as a predicted responder to glatiramer acetate if the genotype is AA at rs10214633, rs10277267, rs10935015, rs10935019, rs10988087, rs11081859, rs11694344, rs12256889, rs12340584, rs12494606, rs1415557, rs17007730, rs17087180, rs17104665, rs17104742, rs17588454, rs17807327, rs1892974, rs2088713, rs214526, rs2374730, rs4255033, rs4306478, rs4343256, rs4344916, rs4435429, rs4578835, rs4809955, rs496486, rs6015147, rs6097790, rs6584894, rs6713772, rs6909321, rs702355, rs7086707, rs7180867, rs7317000, rs844608, rs844610, rs933863, rs9392358, rs948029, or rs9508834, AT at rs12524041 or rs7806265, AG at rs10277267, rs10950359, rs11599624, rs13245980, rs1415557, rs2521643, rs4255033, rs6584894, rs6909321, rs702355, or rs844626, AC at rs12256889, rs1229542, rs214526, rs6097793, rs7086707, rs7180867, rs844608, or rs844610, TT at rs1007328, rs10931091, rs11617134, rs11709339, rs11719825, rs1229553, rs1234567, rs1234947, rs12532459, rs12593600, rs1264423, rs13042992, rs1320648, rs1538123, rs1591661, rs17134651, rs17666347, rs2461319, rs2508806, rs2722396, rs2722398, rs2895215, rs401618, rs4369324, rs4483642, rs4565951, rs4811492, rs552994, rs6025923, rs6025927, rs6097797, rs657302, rs7232734, rs751370, rs7633210, rs7714122, rs7803164, rs7806265, rs7916897, rs8118441, rs844612, rs9378319, or rs9952995, GT at rs12532459, rs2722398, rs4369324, or rs7093143, CT at rs10950371, rs11761457, rs1229562, rs12529764, rs13021482, rs13238613, rs1538123, rs1591661, rs1611185, rs17807445, rs1941973, rs2461319, rs2685484, rs2895215, rs4634524, rs4799760, rs6097797, rs7080507, rs7238006, rs7789703, rs7803164, rs844612, or rs947603, GG at rs10083547, rs10136012, rs10950359, rs11599624, rs12055694, rs1229558, rs1237625, rs12496278, rs12540494, rs12633010, rs12637073, rs1282540, rs1282546, rs12968586, rs1299325, rs13245980, rs16999008, rs17104665, rs17104742, rs2033471, rs2155262, rs2487889, rs2487896, rs2511064, rs2521643, rs2530121, rs2530123, rs28861531, rs3135391, rs4148871, rs4289164, rs4445746, rs6097801, rs6543934, rs6558102, rs656975, rs6971202, rs7093143, rs7244801, rs752979, rs7619350, rs7955917, rs844626, rs873216, rs894857, rs9315048, rs9332420, rs933864, rs948032, rs949298, or rs998051, CG at rs11618546 or rs860722, or CC at rs1041897, rs10853605, rs10935016, rs10950371, rs11009827, rs11009835, rs11618546, rs11907046, rs1229542, rs1229555, rs1229562, rs1229563, rs1229564, rs1229568, rs12488259, rs12639443, rs13021482, rs13238613, rs1573706, rs1683691, rs17575455, rs17807445, rs2177073, rs2187495, rs2277431, rs2521644, rs2685484, rs2937395, rs4281882, rs4466940, rs4468448, rs4634524, rs4799760, rs6091820, rs6097782, rs6097793, rs6123749, rs660075, rs7080507, rs7789703, rs7963693, rs8099595, rs844602, rs860722, rs884266, rs913882, rs9378684, rs9405541, rs9405546, rs947603, or rs9944913.

13. The method of claim 12, comprising determining the genotype at one or more single nucleotide polymorphisms (SNPs) selected from the group consisting of:
rs947603, rs1007328, rs1573706, rs2177073, rs2487896, rs2511064, rs2521644, rs3135391, rs4148871, rs4343256, rs4344916, rs4369324, rs4445746, rs6097801, rs9508834, rs9944913, rs10853605, rs10931091, rs10950359, rs10988087, rs11599624, rs11617134, rs12256889, rs12639443, rs13042992, rs13238613, rs17087180, rs17575455 and rs17807327.

14. The method of claim 12, wherein the genotype is determined at SNPs:
a) rs2521644, rs12256889, rs214526, rs17771939, rs496486, and rs949298, and a score is assigned to each genotype of each SNP, for the purpose of determining if the human subject is a predicted responder to glatiramer acetate, wherein the scores are as shown in tables 7a-f;
b) rs2521644, rs12256889, rs214526, rs17771939, rs496486, and rs2511064, and a score is assigned to each genotype of each SNP, for the purpose of determining if the human subject is a predicted responder to glatiramer acetate, wherein the scores are as shown in tables 9a-f, a relative weight is assigned to each SNP, for the purpose of determining if the human subject is a predicted responder to glatiramer acetate, wherein the relative weight is as shown in table 10;

c) rs12256889, rs17771939, rs2511064, and rs2521644, and a score is assigned to each genotype of each SNP, for the purpose of determining if the human subject is a predicted responder to glatiramer acetate, wherein the scores are as shown in tables 9a-f, and a relative weight is assigned to each SNP, for the purpose of determining if the human subject is a predicted responder to glatiramer acetate, wherein the relative weight is as shown in table 11;

d) rs11599624, rs12639443, rs13042992, rs13238613, rs17087180, rs17771939, rs17807327, rs2487896, rs3135391, rs4148871, rs4343256, rs4344916, and rs9508834;

e) rs12256889, rs12639443, rs13238613, rs1573706, rs17087180, rs17771939, rs17807327, rs2487896, rs4343256, rs4344916, rs4369324, rs4445746, and rs9944913;

f) rs10988087, rs12639443, rs13042992, rs13238613, rs1573706, rs17087180, rs17771939, rs17807327, rs4148871, rs4344916, rs6097801, and rs9508834;

g) rs10988087, rs12256889, rs12639443, rs17087180, rs17771939, rs2177073, rs2521644, rs4344916, rs4369324, rs6097801, rs9508834, and rs9944913;

h) rs10988087, rs11617134, rs12639443, rs13042992, rs17087180, rs17771939, rs17807327, rs2487896, rs4148871, rs4344916, rs4445746, rs6097801, and rs9508834;

i) rs10988087, rs11617134, rs12639443, rs13042992, rs17087180, rs17771939, rs17807327, rs2487896, rs2521644, rs4148871, rs4344916, rs4445746, and rs6097801;

j) rs10988087, rs12256889, rs12639443, rs17087180, rs17771939, rs17807327, rs2487896, rs4148871, rs4344916, rs6097801, and rs9508834;

k) rs1007328, rs11617134, rs12639443, rs13238613, rs1573706, rs17087180, rs17771939, rs17807327, rs4343256, rs4344916, rs9508834, and rs9944913;

l) rs12639443, rs17087180, rs17771939, rs17807327, rs2487896, rs4148871, rs4343256, rs4344916, rs4369324, rs4445746, rs6097801, rs9508834, and rs9944913;

m) rs11617134, rs12639443, rs17087180, rs17771939, rs17807327, rs2487896, rs3135391, rs4148871, rs4344916, rs4369324, rs6097801, rs9508834, and rs9944913;

n) rs10988087, rs12639443, rs13238613, rs17087180, rs17771939, rs2487896, rs4148871, rs4343256, rs4344916, and rs9508834;

o) rs11617134, rs12256889, rs12639443, rs13042992, rs17087180, rs17771939, rs17807327, rs2177073, rs2487896, rs4343256, rs4344916, rs6097801, and rs9508834;

p) rs10950359, rs11617134, rs12639443, rs17087180, rs17771939, rs2487896, rs2511064, rs3135391, rs4148871, rs4343256, rs4344916, rs9508834, and rs9944913;

q) rs12256889, rs12639443, rs13042992, rs17087180, rs17771939, rs17807327, rs2487896, rs2521644, rs4344916, and rs6097801;

r) rs10950359, rs10988087, rs11599624, rs12256889, rs12639443, rs13042992, rs17087180, rs17771939, rs17807327, rs2521644, rs3135391, rs4344916, and rs9508834;

s) rs1007328, rs10950359, rs12256889, rs12639443, rs13042992, rs1573706, rs17087180, rs17771939, rs17807327, rs4343256, rs4344916, rs947603, and rs9508834; or t) rs11599624, rs12256889, rs12639443, rs1573706, rs17087180, rs17771939, rs17807327, rs2177073, rs2487896, rs4344916, rs6097801, rs9508834, and rs9944913.

15. The method of claim 14, wherein a score is assigned to each genotype of each SNP, for the purpose of determining if the human subject is a predicted responder to glatiramer acetate, wherein the scores are as shown in tables 18a-s and 19a-h.

16. The method of claim 14, wherein a relative weight is assigned to each SNP, for the purpose of determining if the human subject is a predicted responder to glatiramer acetate, wherein the relative weight is as shown in one of tables 20-36, wherein the table selected corresponds to the SNPs at which a genotype was determined.

17. The method of claim 12, comprising determining the genotype at one or more single nucleotide polymorphisms (SNPs) selected from the group consisting of: rs9508834, rs17807327, rs4344916, rs12639443 and rs17087180.

18. The method of claim 17, comprising determining the genotype at one or more single nucleotide polymorphisms (SNPs) selected from the group consisting of: rs4344916, rs12639443, and rs17087180.

19. The method of claim 12, comprising determining the genotype at each of the single nucleotide polymorphisms (SNPs): rs4344916, rs12639443, rs17087180 and rs17771939.

20. The method of claim 19, comprising determining the genotype at each of the single nucleotide polymorphisms (SNPs): rs4344916, rs12639443, rs17087180, rs17771939 and rs9508834.

21. The method of claim 19, comprising determining the genotype at each of the single nucleotide polymorphisms (SNPs): rs4344916, rs12639443, rs17087180, rs17771939 and rs17807327.

22. The method of claim 19, wherein the genotype at each of the single nucleotide polymorphisms (SNPs): rs4344916, rs12639443, rs17087180, rs17771939, rs9508834 and rs17807327.

23. A method of identifying a subject as a predicted responder to glatiramer acetate, comprising the steps of:
(i) determining using a probe or primer a genotype of the subject at the single nucleotide polymorphism (SNP) rs17771939 and at one or more single nucleotide polymorphisms (SNP) selected from the group consisting of: rs1007328, rs10083547, rs10136012, rs10214633, rs10277267, rs1040194, rs1041897, rs10853605, rs10931091, rs10935015, rs10935016, rs10935019, rs10950359, rs10950371, rs10988087, rs11009827, rs11009835, rs11081859, rs11599624, rs11617134, rs11618546, rs11694344, rs11709339, rs11719825, rs11761457, rs11907046, rs12055694, rs12256889, rs1229542, rs1229553, rs1229555, rs1229558, rs1229562, rs1229563, rs1229564, rs1229568, rs12340584, rs1234567, rs1234947, rs1237625, rs12488259, rs12494606, rs12496278, rs12524041, rs12529764, rs12532459, rs12540494, rs12593600, rs12633010, rs12637073, rs12639443, rs1264423, rs1282540, rs1282546, rs12968586, rs1299325, rs13021482, rs13042992, rs1320648, rs13238613, rs13245980, rs1415557, rs1538123, rs1573706, rs1591661, rs1611185, rs1683691, rs16999008, rs17007730, rs17087180, rs17104665, rs17104742, rs17134651, rs17575455, rs17588454, rs17666347, rs17807327, rs17807445, rs1886308, rs1892974, rs1941973, rs2033471, rs2088713, rs214526, rs2155262, rs2177073, rs2187495, rs2277431, rs2305623, rs2374730, rs2461319, rs2487889, rs2487896, rs2508806, rs2511064, rs2521643, rs2521644, rs2530121, rs2530123, rs2685484, rs2722396, rs2722398, rs28861531, rs2895215, rs2937395, rs3135391, rs35831078, rs3742228, rs401618, rs4148871, rs4255033, rs4281882, rs4289164, rs4306478, rs4343256, rs4344916, rs4369324, rs4435429, rs4445746, rs4466940, rs4468448, rs4483642, rs4565951, rs4578835, rs4634524, rs4799760, rs4809955, rs4811492, rs496486, rs552994, rs6015147, rs6025923, rs6025927, rs6091820, rs6097782, rs6097790, rs6097793, rs6097797, rs6097801, rs6123749, rs6543934, rs6558102, rs656975, rs657302, rs6584894, rs660075, rs6713772, rs6909321, rs6971202, rs702355, rs7080507, rs7086707, rs7093143, rs7178587, rs7180867, rs7232734, rs7238006, rs7244801, rs7317000, rs751370, rs752979, rs7619350, rs7633210, rs7714122, rs7789703, rs7803164, rs7806265, rs7916897, rs7955917, rs7963693, rs8099595, rs8118441, rs844602, rs844608, rs844610, rs844612, rs844626, rs860722, rs873216, rs884266, rs894857, rs913882, rs9315048, rs9332420, rs933863, rs933864, rs9378319, rs9378684, rs9392358, rs9405541, rs9405546, rs947603, rs948029, rs948032, rs949298, rs9508834, rs9944913, rs9952995, and rs998051; and (ii) identifying the subject as a predicted responder to glatiramer acetate if the genotype is AA at rs10214633, rs10277267, rs10935015, rs10935019, rs10988087, rs11081859, rs11694344, rs12256889, rs12340584, rs12494606, rs1415557, rs17007730, rs17087180, rs17104665, rs17104742, rs17588454, rs17807327, rs1892974, rs2088713, rs214526, rs2374730, rs4255033, rs4306478, rs4343256, rs4344916, rs4435429, rs4578835, rs4809955, rs496486, rs6015147, rs6097790, rs6584894, rs6713772, rs6909321, rs702355, rs7086707, rs7180867, rs7317000, rs844608, rs844610, rs933863, rs9392358, rs948029, or rs9508834, AT at rs12524041 or rs7806265, AG at rs10277267, rs10950359, rs11599624, rs13245980, rs1415557, rs2521643, rs4255033, rs6584894, rs6909321, rs702355, or rs844626, AC at rs12256889, rs1229542, rs214526, rs6097793, rs7086707, rs7180867, rs844608, or rs844610, TT at rs1007328, rs10931091, rs11617134, rs11709339, rs11719825, rs11761457, rs1229553, rs1234567, rs1234947, rs12532459, rs12593600, rs1264423, rs13042992, rs1320648, rs1538123, rs1591661, rs17134651, rs17666347, rs17771939, rs2461319, rs2508806, rs2722396, rs2722398, rs2895215, rs401618, rs4369324, rs4483642, rs4565951, rs4811492, rs552994, rs6025923, rs6025927, rs6097797, rs657302, rs7232734, rs751370, rs7633210, rs7714122, rs7803164, rs7806265, rs7916897, rs8118441, rs844612, rs9378319, or rs9952995, GT at rs12532459, rs2722398, rs4369324, or rs7093143, CT at rs10950371, rs11761457, rs1229562, rs12529764, rs13021482, rs13238613, rs1538123, rs1591661, rs1611185, rs17807445, rs1941973, rs2461319, rs2685484, rs2895215, rs4634524, rs4799760, rs6097797, rs7080507, rs7238006, rs7789703, rs7803164, rs844612, or rs947603, GG at rs10083547, rs10136012, rs10950359, rs11599624, rs12055694, rs1229558, rs1237625, rs12496278, rs12540494, rs12633010, rs12637073, rs1282540, rs1282546, rs12968586, rs1299325, rs13245980, rs16999008, rs17104665, rs17104742, rs2033471, rs2155262, rs2487889, rs2487896, rs2511064, rs2521643, rs2530121, rs2530123, rs28861531, rs3135391, rs4148871, rs4289164, rs4445746, rs6097801, rs6543934, rs6558102, rs656975, rs6971202, rs7093143, rs7244801, rs752979, rs7619350, rs7955917, rs844626, rs873216, rs894857, rs9315048, rs9332420, rs933864, rs948032, rs949298, or rs998051, CG at rs11618546 or rs860722, or CC at rs1041897, rs10853605, rs10935016, rs10950371, rs11009827, rs11009835, rs11618546, rs11907046, rs1229542, rs1229555, rs1229562, rs1229563, rs1229564, rs1229568, rs12488259, rs12639443, rs13021482, rs13238613, rs1573706, rs1683691, rs17575455, rs17807445, rs2177073, rs2187495, rs2277431, rs2521644, rs2685484, rs2937395, rs4281882, rs4466940, rs4468448, rs4634524, rs4799760, rs6091820, rs6097782, rs6097793, rs6123749, rs660075, rs7080507, rs7789703, rs7963693, rs8099595, rs844602, rs860722, rs884266, rs913882, rs9378684, rs9405541, rs9405546, rs947603, or rs9944913, thereby identifying the subject as a predicted responder to glatiramer acetate.

* * * * *